US008748423B2

(12) United States Patent
Hangauer, Jr. et al.

(10) Patent No.: US 8,748,423 B2
(45) Date of Patent: Jun. 10, 2014

(54) COMPOSITIONS AND METHODS FOR THE PREVENTION AND TREATMENT OF CANCER

(75) Inventors: David G. Hangauer, Jr., Lancaster, NY (US); Michael J. Ciesielski, Orchard Park, NY (US); Robert Alan Fenstermaker, Amherst, NY (US)

(73) Assignee: Kinex Pharmaceuticals, LLC, Buffalo, NY (US)

( * ) Notice: Subject to any disclaimer, the term of this patent is extended or adjusted under 35 U.S.C. 154(b) by 305 days.

(21) Appl. No.: 13/046,533

(22) Filed: Mar. 11, 2011

(65) Prior Publication Data

US 2011/0281872 A1 Nov. 17, 2011

Related U.S. Application Data

(60) Provisional application No. 61/324,866, filed on Apr. 16, 2010.

(51) Int. Cl.
A61K 31/535 (2006.01)

(52) U.S. Cl.
USPC ........ 514/235.8; 514/617; 514/357; 544/131; 544/360; 546/337

(58) Field of Classification Search
USPC ............... 514/235.8, 617, 357; 544/131, 360; 546/268.4, 337
See application file for complete search history.

(56) References Cited

U.S. PATENT DOCUMENTS

| | | | |
|---|---|---|---|
| 3,761,477 A | 9/1973 | Schwartz et al. | |
| 3,868,380 A | 2/1975 | Molteni et al. | |
| 4,010,279 A | 3/1977 | Griss et al. | |
| 5,827,887 A | 10/1998 | Gourvest et al. | |
| 5,849,912 A | 12/1998 | Akasaka et al. | |
| 6,624,180 B2 | 9/2003 | South et al. | |
| 6,844,367 B1 | 1/2005 | Zhu et al. | |
| 6,969,726 B2 | 11/2005 | Lou et al. | |
| 7,300,931 B2* | 11/2007 | Hangauer, Jr. | 514/235.5 |
| 7,851,470 B2 | 12/2010 | Hangauer, Jr. et al. | |
| 7,935,697 B2 | 5/2011 | Hangauer, Jr. et al. | |
| 7,939,529 B2 | 5/2011 | Hangauer, Jr. et al. | |
| 7,968,574 B2* | 6/2011 | Hangauer, Jr. | 514/357 |
| 8,003,641 B2* | 8/2011 | Hangauer, Jr. | 514/235.5 |
| 8,236,799 B2* | 8/2012 | Hangauer, Jr. | 514/235.5 |
| 2004/0242572 A1 | 12/2004 | Stenkamp et al. | |
| 2005/0059713 A1 | 3/2005 | Mjalli et al. | |
| 2006/0160800 A1 | 7/2006 | Hangauer, Jr. | |
| 2007/0015752 A1 | 1/2007 | Hangauer, Jr. | |
| 2007/0197783 A1 | 8/2007 | Hangauer, Jr. | |
| 2010/0210649 A1* | 8/2010 | Djaballah et al. | 514/236.5 |
| 2010/0249130 A1 | 9/2010 | Hangauer, Jr. | |

FOREIGN PATENT DOCUMENTS

| | | |
|---|---|---|
| EP | 0463638 A1 | 1/1992 |
| JP | 62252755 A | 11/1987 |
| JP | 2002020362 A | 1/2002 |
| JP | 2003231633 A | 8/2003 |
| JP | 2006510737 A | 3/2006 |
| WO | WO-9204315 A1 | 3/1992 |
| WO | WO-9219208 A1 | 11/1992 |
| WO | WO-9220645 A1 | 11/1992 |
| WO | WO-9427949 A1 | 12/1994 |
| WO | WO-9612473 A1 | 5/1996 |
| WO | WO-9901127 A1 | 1/1999 |
| WO | WO-0119788 A2 | 3/2001 |
| WO | WO-0156974 A2 | 8/2001 |
| WO | WO-0185726 A1 | 11/2001 |
| WO | WO-0196307 A2 | 12/2001 |
| WO | WO-0198245 A2 | 12/2001 |
| WO | WO-02079197 A1 | 10/2002 |
| WO | WO-03059903 A2 | 7/2003 |
| WO | WO-03066579 A2 | 8/2003 |
| WO | WO-03076406 A1 | 9/2003 |
| WO | WO-03078404 A1 | 9/2003 |
| WO | WO-03087057 A1 | 10/2003 |
| WO | WO-03093248 A1 | 11/2003 |
| WO | WO-03093297 A2 | 11/2003 |
| WO | WO-03099771 A2 | 12/2003 |
| WO | WO-2004000295 A1 | 12/2003 |
| WO | WO-2004011427 A2 | 2/2004 |
| WO | WO-2004011456 A1 | 2/2004 |
| WO | WO-2004014279 A2 | 2/2004 |
| WO | WO-2004024702 A1 | 3/2004 |
| WO | WO-2004041789 A1 | 5/2004 |
| WO | WO-2004043925 A2 | 5/2004 |
| WO | WO-2004056774 A2 | 7/2004 |
| WO | WO-2004078747 A1 | 9/2004 |
| WO | WO-2005013914 A2 | 2/2005 |
| WO | WO-2005032493 A2 | 4/2005 |
| WO | WO-2005097750 A1 | 10/2005 |
| WO | WO-2006071960 A2 | 7/2006 |
| WO | WO-2007026920 A2 | 3/2007 |
| WO | WO-2007095383 A2 | 8/2007 |
| WO | WO-2007136790 A2 | 11/2007 |
| WO | WO-2008002676 A2 | 1/2008 |
| WO | WO-2008127727 A1 | 10/2008 |

OTHER PUBLICATIONS

Smith et al. CAS: 146: 229329, 2007.*
Revarello et al. CAS: 141: 81703, 2004.*
Maeda et al. CAS: 141: 199479, 2004.*
Backes et al. "Carbon-Carbon Bond-Forming Methods on Solid Support." *J. Am. Chem. Soc.* 116.24(1994):11171-11172.
Blessington et al. "Chromatographic Approaches to the Quality Control of Chiral Propionate Anti-Inflammatory Drugs and Herbicides." *J. Chromatography*. 469(1989):183-190.
Satoh et al. "An Efficient Synthesis of 4-aryl-2,6-di-tert-butylphenols by a Palladium-Catalyzed Cross-Coupling Reaction." *Synthesis*. 11(1994):1146-1148.
Satoh et al. "Comparison of the Inhibitory Action of Synthetic Capsaicin Analogs With Various NADH-Ubiquinone Oxidoreductases." *Biochem. Biophys. Acta*. 1273.1(1996):21-30.

(Continued)

Primary Examiner — Rei-tsang Shiao
(74) Attorney, Agent, or Firm — Cooley LLP; Ivor R. Elrifi; Heidi A. Erlacher

(57) ABSTRACT

The invention relates to compositions and methods for the treatment and prevention of cancer and other cell proliferative disorders.

19 Claims, 14 Drawing Sheets

(56) References Cited

OTHER PUBLICATIONS

Van Overbeke et al. "Comparative Study on the Enantiomeric Separation of Several Non-Steroidal Anti-Inflammatory Drugs on Two Cellulose-Based Chiral Stationary Phases." *J. Liquod Chromatography*. 18.12(1995):2427-2443.
An et al. "Oxidation of N-Benzylaldimines to N-Benzylamides by MCPBA and BF3OEt2." *Synlett*. (2003):876-878.
Byrn et al. "Solid-State Chemistry of Drugs." Second Edition. (1999):233-247.
Cain et al. "Potential Antitumor Agents." *J. Med. Chem.* 11.5(1968):963-966.
Croteau et al. "Adults with Newly Diagnosed High-Grade Gliomas." *Current Treatment Options in Oncology*. 2(2001):507-515.
Davidson et al. "Discovery and Characterization of a Substrate Selective p38α Inhibitor." *Biochemistry*. 43(2004):11658-11671.
Duong et al. "Inhibition of Osteoclast Function by Adenovirus Expressing Antisense Protein-Tyrosine Kinase 2." *J. Biol. Chem.* 276.10(2001):7484-7492.
Frame. "Src in Cancer: Deregulation and Consequences for Cell Behaviour." *Biochem. Biophys. Acta*. 1602(2002):114-130.
Garrido et al. "Synthesis of N,N'-Diacyl-1,2-di-(4-pyridyl)ethylenediamines." *J. Het. Chem.* 18(1981):1305-1308.
Golub et al. "Molecular Classification of Cancer: Class Discovery and Class Prediction by Gene Expression Monitoring." *Science*. 286(1999):531-537.
Guo et al. "Tyrosine Phosphorylation of the NR2B Subunit of the NMDA Receptor in the Spinal Cord During the Development and Maintenance of Inflammatory Hyperalgesia." *J. Neurosci.* 22.14(2002):6208-6217.
Hadjeri et al. "Antimitotic Activity of 5-hydroxy-7-methoxy-2-phenyl-4-quinolones." *J. Med. Chem.* 47(2004):4964-4970.
Han. "Advances in Characterization of Pharmaceutical Hydrates." *Trends in Bio/Pharmaceutical Industry*. 3(2006):25-29.
Honma et al. "Antiallergic Agents." *J. Med. Chem.* 26(1983):1499-1504.
Huff. "HIV Protease: A Novel Chemotherapeutic Target for AIDS." *J. Med. Chem.* 34.8(1991):2305-2314.
Lala et al. "Role of Nitric Oxide in Tumor Progression: Lessons from Experimental Tumors." *Cancer Metastasis Rev*. 17.1(1998):91-106.
Liechti et al. "Salicylanilides as Inhibitors of the Protein Tyrosine Kinase Epidermal Growth Factor Receptor." *Eur. J. Med. Chem.* 39.1(2004):11-26.
Million et al. "Inhibition of the EGF-Stimulated Cellular Proliferation of ER 22 Cells by Hydroxybiphenyl Derivatives." *J. Med. Chem.* 38.23(1995):4693-4703.
Miyazaki et al. "Src Kinase Activity is Essential for Osteoclast Function." *J. Biol. Chem.* 279.17(2004):17660-17666.
Parang et al. "Recent Advances in the Discovery of Src Kinase Inhibitors." *Expert Opin. Ther. Patents*. 15.9(2005):1183-1207.
Paul et al. A "Src Deficiency or Blockade of Src Activity in Mice Provides Cerebral Protection Following Stroke." *Nat. Med.* 7.2(2001):222-227.
Planas-Silva et al. "Targeting c-Src Kinase Enhances Tamoxifen's Inhibitory Effect on Cell Growth by Modulating Expression of Cell Cycle and Survival Proteins." *Cancer Chemotherapy Pharmacol*. 60.4(2006):535-543.
Rouhi. "The Right Stuff: From Research and Development to the Clinic, Getting Drug Crystals right is Full of Pitfalls." *Chem. Eng. News*. (2003):32-35.
Stella et al. "Prodrugs: Challenges and Rewards, Part 1." *Biotechnology: Pharmaceutical Aspects*. (2007):24 (2007).
U.S. Pharmacopia #23, National Formulary #18. (1995):1843-1844.
Vippagunt et al. "Cyrstalline Solids." *Advanced Drug Delivery Reviews*. 48(2001):3-26.
Yu et al. "Src, a Molecular Switch Governing Gain Control of Synaptic Transmission Mediated by N-methyl-D-Aspartate Receptors." *Proc. Natl. Acad. Sci. USA*. 96(1999):7697-7704.
Zhang et al. "Design, Synthesis, and SAR of Anthranilamide-Based Factor Xa Inhibitors Incorporating Substituted Biphenyl P4 Motifs." *Bioorg. Med. Chem. Lett.* 14.4(2004):983-987.
Boschelli et al. "Optimization of 4-Phenylamino-3-quinolinecarbonitriles as Potent Inhibitors of Src Kinase Activity." *J. Med. Chem.* 44.23(2001):3965-3977.
Lesslie et al. "Combined Activity of Dasatinib (BMS-354825) and Oxaliplatin in an Orthotopic Model of Metastatic Colorectal Carcinoma." *Proc. Am. Assoc. Cancer Res.* 47(2006). Abstract #4745.
Masood et al. "A Convenient Synthesis of Sendaverine." *Synth. Commun.* 10.7(1980):541-544.
Reagen-Shaw et al. "Dose Translation from Animal to Human Studies Revisited." *FASEB J*. 22(2007):659-661.
Wilkinson et al. "Pharmacokinetics: The Dynamics of Drug Absorption, Distribution, and Elimination." *Goodman and Gilman's The Pharmacological Basis of Therapeutics*. New York: McGraw Hill. Chapter 1(2001):3-29.
Yezhelyev et al. "Inhibition of Src Tyrosine Kinase as Treatment for Human Pancreatic Cancer Growing Orthotopically in Nude Mice." *Clin. Cancer Res.* 10(2004):8028-8036.

\* cited by examiner

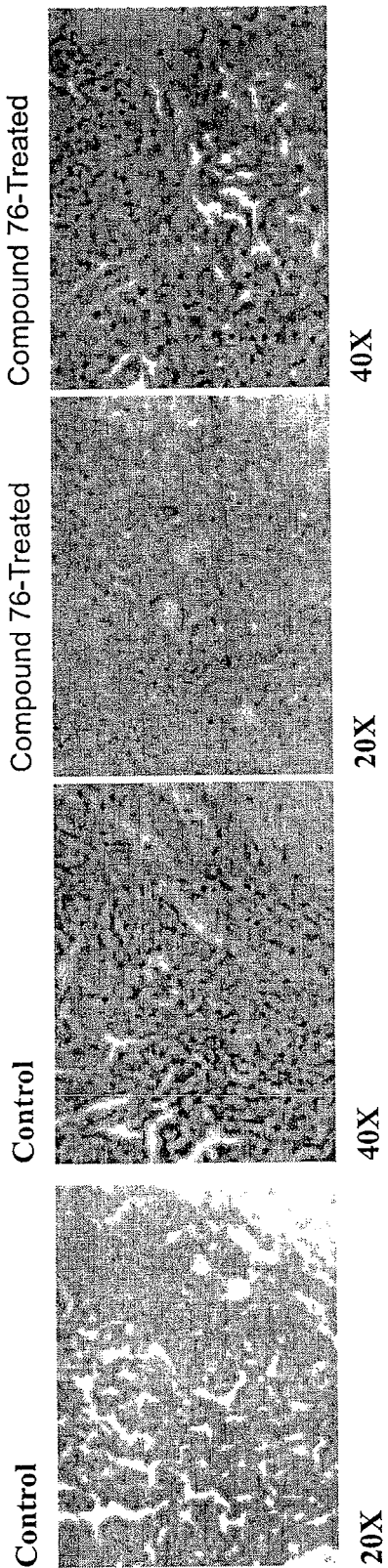

COMPOSITIONS AND METHODS FOR THE PREVENTION AND TREATMENT OF CANCER

RELATED APPLICATIONS

This application claims priority to, and the benefit of, U.S. Provisional Application Ser. No. 61/324,866, filed Apr. 16, 2010. The entire content of which is incorporated by reference herein.

BACKGROUND OF THE INVENTION

Cancer is the second leading cause of death in the United States, exceeded only by heart disease. (*Cancer Facts and Figures* 2004, American Cancer Society, Inc.). Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational "mechanisms" may lead to the development of cancer. As such, heterogeneity frequently exists between cancer cells taken from tumors of the same tissue and same type that have originated in different individuals. Frequently observed mutational "mechanisms" associated with some cancers may differ between one tissue type and another (e.g., frequently observed mutational "mechanisms" leading to colon cancer may differ from frequently observed "mechanisms" leading to leukemias). It is therefore often difficult to predict whether a particular cancer will respond to a particular chemotherapeutic agent (*Cancer Medicine*, 5$^{th}$ edition, Bast et al., B. C. Decker Inc., Hamilton, Ontario).

Maglignant gliomas cause over 15,000 cancer deaths in the United States each year. These brain tumors are among the most difficult human cancers to treat, even with extensive surgery, radiation therapy and chemotherapy, survival remains poor. The most widely used chemotherapy drug for treating glioma patients is Temodar (Temozolamide). Even with the best current therapy available the probability that a glioblastoma patient will survive at least two years is 9%. Brain edema is also a serious problem for these brain cancer patients and they often require treatment with corticosteroids to reduce the edema, but are then subjected to the common steroidal side effects of immunosuppression, hypertension and steroidal dependence. A major challenge in developing new therapies for treating gliomas and brain metastases is that very few small molecule anti-tumor drugs are capable of penetrating the brain well enough to provide therapeutically effective drug levels. Consequently, the development of more effective drugs for treating brain cancer and brain metastases is a large unmet medical need. The present invention addresses these needs.

Accordingly, new compositions and methods for treating and preventing reoccurrence of proliferation disorders, including cancer, are needed. The present invention addresses these needs.

SUMMARY OF THE INVENTION

The invention provides a pharmaceutical composition including a compound according to Formula IB:

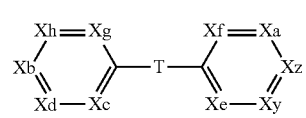

(Formula IB)

or a pharmaceutically acceptable salt, solvate, hydrate, or prodrug thereof, where the compound is present in an amount from 50 mg to 500 mg in the composition and wherein:

T is a bond;
$X_y$ is CY, N, or N—O;
$X_z$ is CZ;
Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;
$X_a$ is $CR_a$, N, or N—O;
$X_b$ is $CR_b$, N, or N—O;
$X_c$ is $CR_c$, N, or N—O;
$X_d$ is $CR_d$, N, or N—O;
$X_e$ is $CR_e$, N, or N—O;
$X_f$ is $CR_4$, N, or N—O;
$X_g$ is $CR_5$, N, or N—O;
$X_h$ is $CR_6$, N, or N—O;
$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

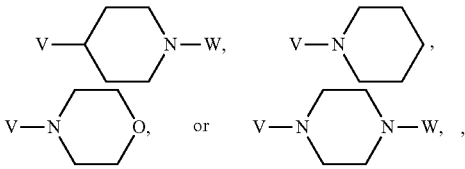

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

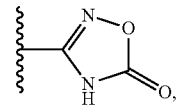

P is $SO_3H$, $OSO_3H$, $PO_3H_2$, $OPO_3H_2$, $NH_2$, $NHR_{19}$, $NR_{20}R_{21}$, tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower alkyl is linear or branched alkyl;

K is aryl, heteroaryl, C(O)$NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

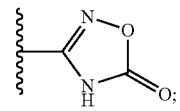 [SMILES: *c1noc(=O)[nH]1]

L is aryl, heteroaryl, OH, C(O)$NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

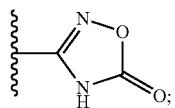 [SMILES: *c1noc(=O)[nH]1]

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

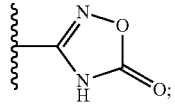 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

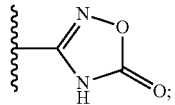 [SMILES: *c1noc(=O)[nH]1]

R$_{19}$, R$_{20}$ and R$_{21}$ are C$_1$, C$_2$, C$_3$, C$_4$, C$_5$, or C$_6$ alkyl or R$_{19}$ and R$_{20}$ taken together with the attached nitrogen atom form a five membered ring;

V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

Z is (CHR$_1$)$_n$—C(O)—NR$_2$(CHR$_3$)$_m$—Ar, where Ar is a substituted or unsubstituted aryl or nitrogen-containing heteroaryl group, R$_1$, R$_2$, and R$_3$ are independently H or C$_1$, C$_2$, C$_3$, C$_4$, C$_5$, or C$_6$ alkyl; and n and m are independently 0, 1, or 2.

Preferably, Z is

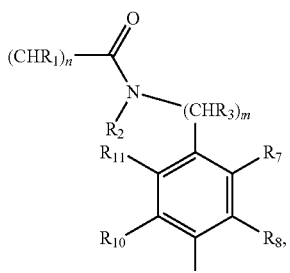

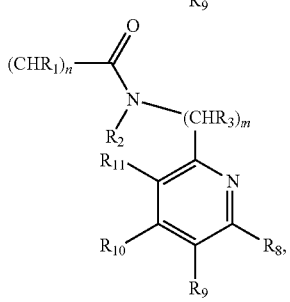

-continued

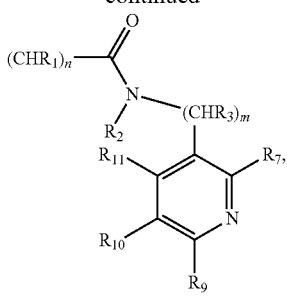

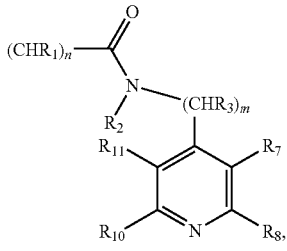

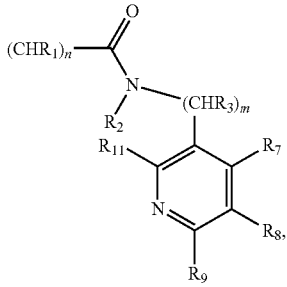

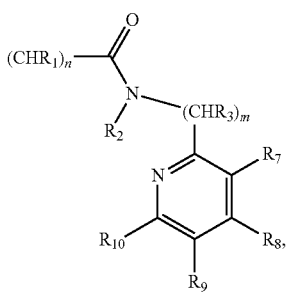

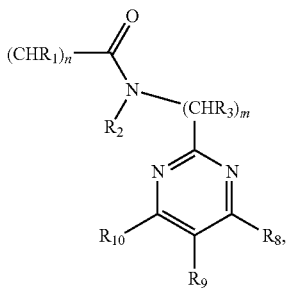

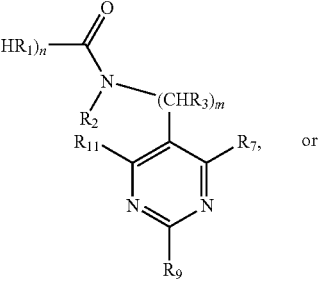 or

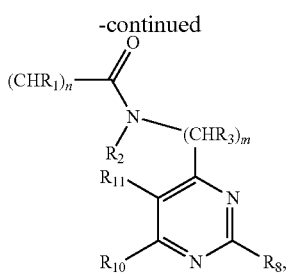

wherein $R_7$, $R_8$, $R_9$, $R_{10}$, and $R_{11}$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

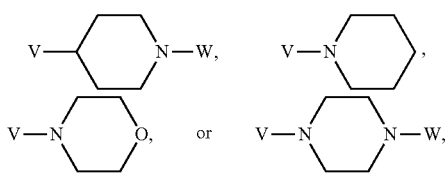

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

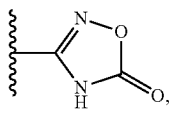

P is $SO_3H$, $OSO_3H$, $PO_3H_2$, $OPO_3H_2$, $NH_2$, $NHR_{19}$, $NR_{20}R_{21}$, tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is aryl, heteroaryl, C(O)NH$_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

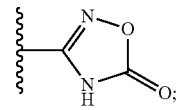 [SMILES: *c1noc(=O)[nH]1]

L is aryl, heteroaryl, OH, C(O)NH$_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

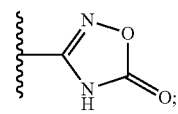

M is aryl, heteroaryl, OH, C(O)NH$_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

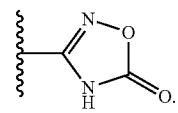 [SMILES: *c1noc(=O)[nH]1]

Q is aryl, heteroaryl, OH, C(O)NH$_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

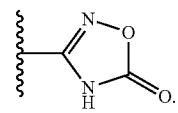 [SMILES: *c1noc(=O)[nH]1]

More preferably, Z is

as defined above. Preferably, $X_f$ is $CR_4$, $X_g$ is $CR_5$, and $X_h$ is $CR_6$. Preferably, $R_4$, $R_5$ and $R_6$ are each H. Preferably, m and n are each 1 and $R_2$ and $R_3$ are each H.

Preferably, the compound is selected from

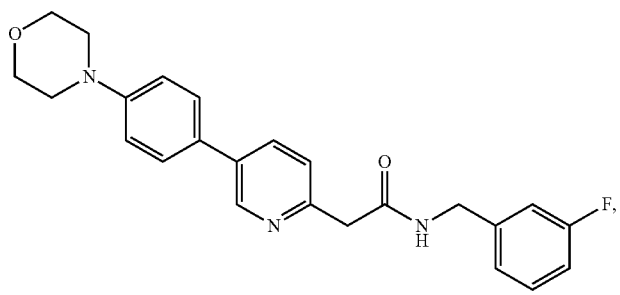

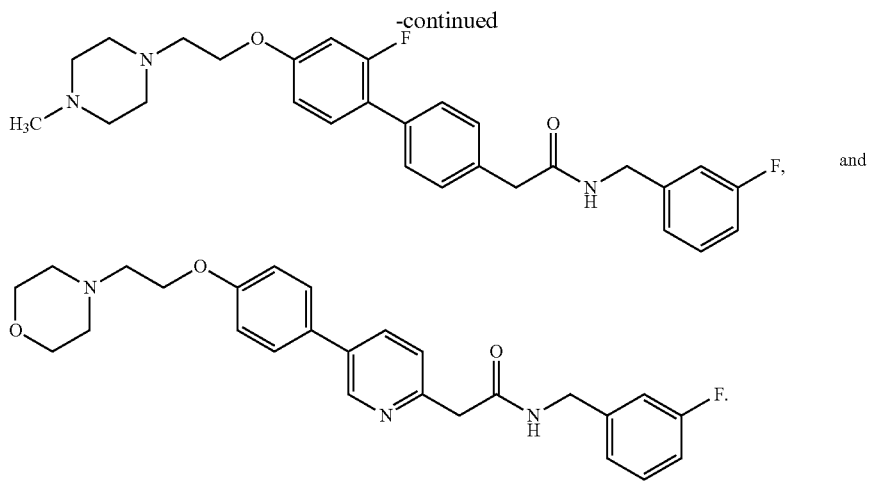

Most preferably, the compound is

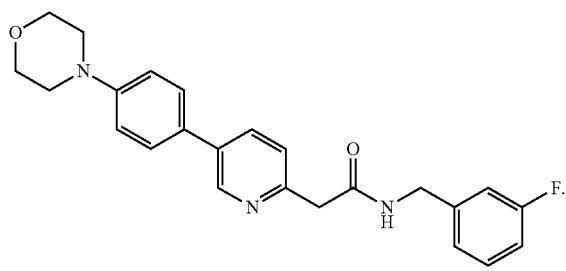 [SMILES: O=C(Cc1ccc(-c2ccc(N3CCOCC3)cc2)cn1)NCc1cccc(F)c1]

The pharmaceutical composition can be formulated for oral, intravenous, intramuscular, or subcutaneous administration. Preferably, the pharmaceutical composition is formulated for oral administration.

The compound can be present in the pharmaceutical composition an amount from about 100 mg to about 400 mg. More preferably, the compound is present in an amount from about 200 mg to about 300 mg. Most preferably, the compound is present in an amount about 250 mg or at 250 mg.

The pharmaceutical composition can include a pharmaceutically acceptable excipient or carrier.

The present invention also provides a method of treating a cell proliferative disorder including administering to a subject in need thereof, a therapeutically effective amount of a compound according to formula IB:

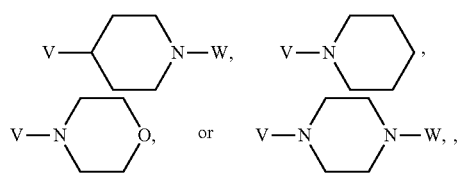

or a pharmaceutically acceptable salt, solvate, hydrate, or prodrug thereof, wherein:

T is a bond;

$X_y$ is CY, N, or N—O;

$X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$X_f$ is $CR_4$, N, or N—O;

$X_g$ is $CR_5$, N, or N—O;

$X_h$ is $CR_6$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

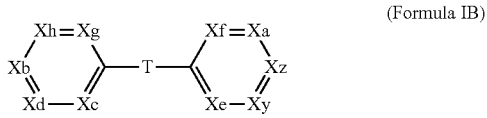

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $PO_3H_2$, $OPO_3H_2$, $NH_2$, $NHR_{19}$, $NR_{20}R_{21}$, tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower alkyl is linear or branched alkyl;

K is aryl, heteroaryl, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

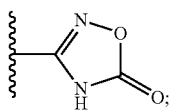 [SMILES: *c1noc(=O)[nH]1]

L is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

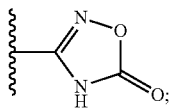

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

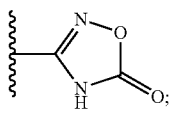

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

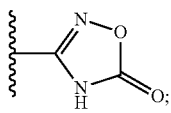 [SMILES: *c1noc(=O)[nH]1]

R$_{19}$, R$_{20}$ and R$_{21}$ are C$_1$, C$_2$, C$_3$, C$_4$, C$_5$, or C$_6$ alkyl or R$_{19}$ and R$_{20}$ taken together with the attached nitrogen atom form a five membered ring;

V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

Z is (CHR$_1$)$_n$—C(O)—NR$_2$(CHR$_3$)$_m$—Ar, where Ar is a substituted or unsubstituted aryl or nitrogen-containing heteroaryl group, R$_1$, R$_2$, and R$_3$ are independently H or C$_1$, C$_2$, C$_3$, C$_4$, C$_5$, or C$_6$ alkyl; and n and m are independently 0, 1, or 2, wherein the therapeutically effective amount is between about 50 mg to about 500 mg and wherein the compound is administered once per 24 hour period.

The present invention also provides a method of preventing reoccurrence of a cell proliferative disorder in a subject previously diagnosed with a cell proliferative disorder including administering to the subject a therapeutically effective amount of a compound according to formula IB:

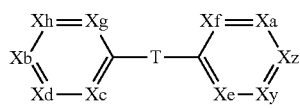

(Formula IB)

or a pharmaceutically acceptable salt, solvate, hydrate, or prodrug thereof, wherein:

T is a bond;
X$_y$ is CY, N, or N—O;
X$_z$ is CZ;
Y is selected from hydrogen, hydroxyl, halogen, lower (C$_1$, C$_2$, C$_3$, C$_4$, C$_5$, or C$_6$) alkyl, C$_1$, C$_2$, C$_3$, C$_4$, C$_5$, or C$_6$ alkoxy, O-lower (C$_1$, C$_2$, C$_3$, C$_4$, C$_5$, or C$_6$) alkyl-aryl, and O-benzyl;
X$_a$ is CR$_a$, N, or N—O;
X$_b$ is CR$_b$, N, or N—O;
X$_c$ is CR$_c$, N, or N—O;
X$_d$ is CR$_d$, N, or N—O;
X$_e$ is CR$_e$, N, or N—O;
X$_f$ is CR$_4$, N, or N—O;
X$_g$ is CR$_5$, N, or N—O;
X$_h$ is CR$_6$, N, or N—O;
R$_a$, R$_b$, R$_c$, R$_d$, R$_e$, R$_4$, R$_5$, and R$_6$ are, independently, hydrogen, hydroxyl, halogen, P, C$_1$, C$_2$, C$_3$, C$_4$, C$_5$, or C$_6$ alkyl, C$_1$, C$_2$, C$_3$, C$_4$, C$_5$, or C$_6$ alkoxy, O-lower (C$_1$, C$_2$, C$_3$, C$_4$, C$_5$, or C$_6$) alkyl-aryl, O-benzyl, C$_1$, C$_2$, C$_3$, C$_4$, C$_5$, or C$_6$ alkyl-OH, COOH, COO-lower (C$_1$, C$_2$, C$_3$, C$_4$, C$_5$, or C$_6$) alkyl, SO$_2$H, SO$_2$-lower (C$_1$, C$_2$, C$_3$, C$_4$, C$_5$, or C$_6$) alkyl,

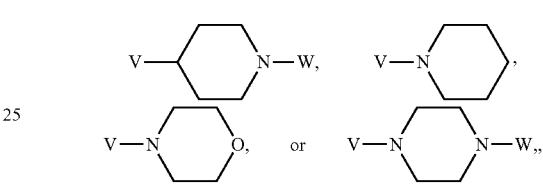

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl;

P is SO$_3$H, OSO$_3$H, PO$_3$H$_2$, OPO$_3$H$_2$, NH$_2$, NHR$_{19}$, NR$_{20}$R$_{21}$,

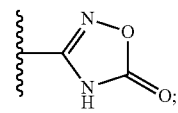 [SMILES: *c1noc(=O)[nH]1]

tetrazole, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q, further wherein lower alkyl is linear or branched alkyl;

K is aryl, heteroaryl, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

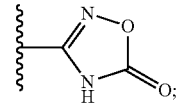 [SMILES: *c1noc(=O)[nH]1]

L is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

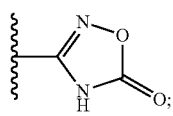 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

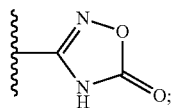 [SMILES: *c1noc(=O)[nH]1]

R$_{19}$, R$_{20}$ and R$_{21}$ are C$_1$, C$_2$, C$_3$, C$_4$, C$_5$, or C$_6$ alkyl or R$_{19}$ and R$_{20}$ taken together with the attached nitrogen atom form a five membered ring;

V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

Z is (CHR$_1$)$_n$—C(O)—NR$_2$(CHR$_3$)$_m$—Ar, where Ar is a substituted or unsubstituted aryl or nitrogen-containing heteroaryl group, R$_1$, R$_2$, and R$_3$ are independently H or C$_1$, C$_2$, C$_3$, C$_4$, C$_5$, or C$_6$ alkyl; and n and m are independently 0, 1, or 2.

The therapeutically effective amount can be between about 50 mg to about 500 mg. Preferably, the therapeutically effective amount can be between about 100 mg to about 400 mg. More preferably, the therapeutically effective amount is between about 200 mg to about 300 mg. Most preferably, the therapeutically effective amount is about 250 mg or 250 mg.

Preferably, the compound is

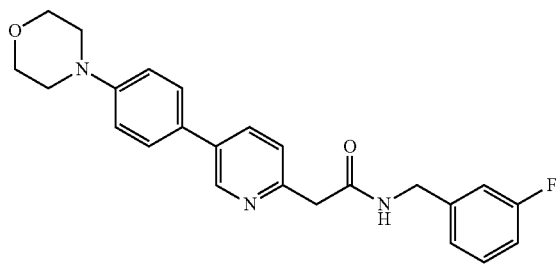

or a pharmaceutically acceptable salt, solvate, hydrate, or prodrug thereof.

The treatment, or the previous treatment, can produce immunological memory or produce memory B-cells and/or memory T-cells in the subject. The treatment can include a reduction in tumor size or a reduction in metastatic cancer cell invasion.

The subject may have been previously treated for the proliferation disorder. The subject may have been in complete or partial remission following treatment for the proliferation disorder. Preferably, the subject was previously treated with a compound of formula IB.

The subject can be a mammal. Preferably, the subject is a human.

The cell proliferative disorder can be a cancer, hematologic tumor or malignancy or a solid tumor (or tumors). Preferably, the cancer is brain cancer. Preferably, the solid tumor (or tumors) is a glioblastoma, oligodendroglioma, astrocytoma or medulloblastoma. More preferably, the solid tumor (or tumors) is a glioblastoma.

The treatment can further include administering a second anti-proliferative agent and/or radiation therapy.

The compound can be administered four times, two times or once daily (per 24 hour period).

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIGS. 7A-D are a series of images showing the histopathology of residual GL261 glioma from Compound 76 treated mice showing large areas of necrosis and lymphocytic infiltration. Panel (A) shows control at 20×. Panel (B) shows control at 40×. Panel (C) shows Compound 76 treated at 20×. (D) Panel showing Compound 76 treated at 40×.

DETAILED DESCRIPTION OF THE INVENTION

Figure 1:
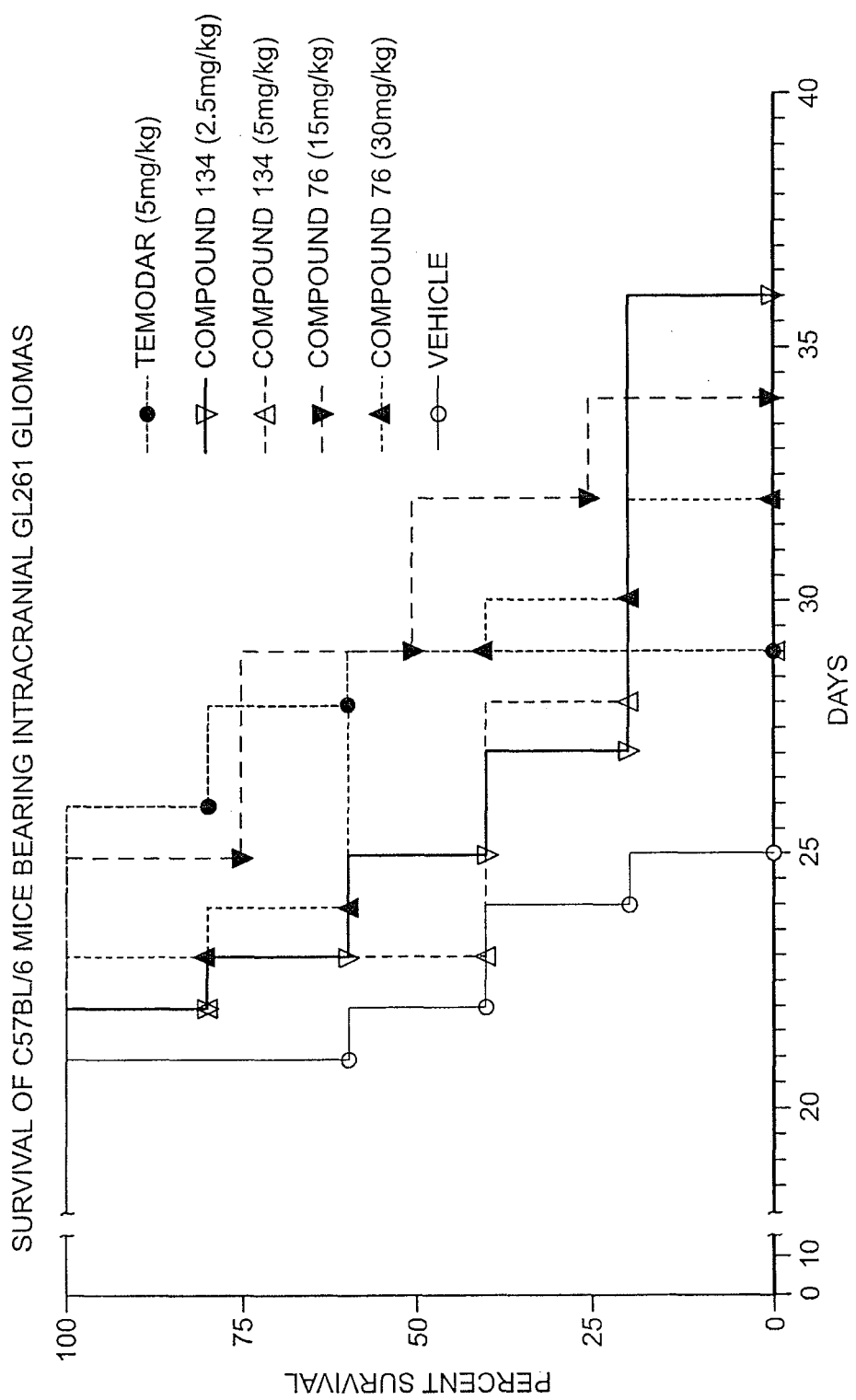
FIG. 1 is a graph showing the survival of C57BL/6 mice bearing intracranial GL261 gliomas over a 40 day period.
Figure 2A:
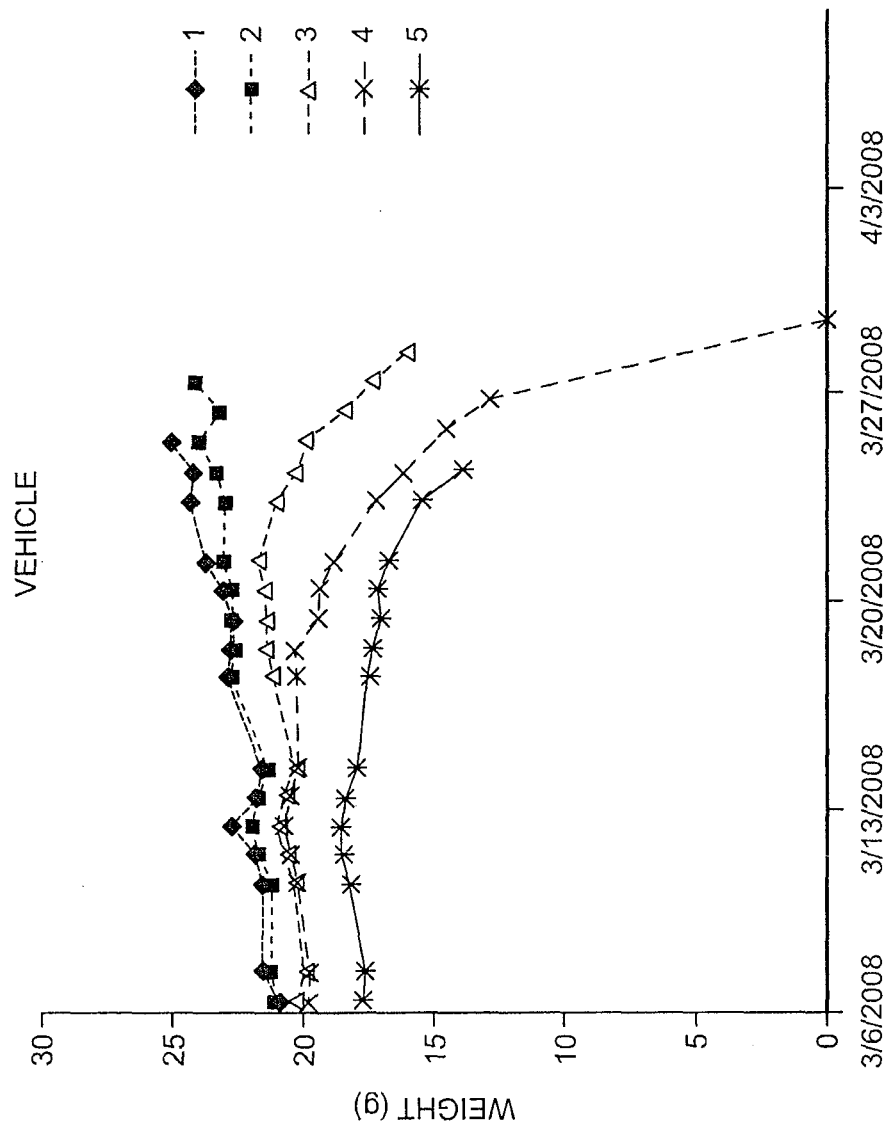
FIGS. 2A-F are a series of graphs showing the weight gain in each of the C57BL/6 mice in the different treatment groups of the intracranial GL261 glioma survival study. Panel (A) shows the weight in vehicle. Panel (B) shows the Temodar treated group. Panel (C) shows the Compound 134 (2.5 mg/kg) treated group. Panel (D) shows the Compound 76 (15 mg/kg) treated group. Panel (E) shows the Compound 134 (5 mg/kg) treated group. Panel (F) shows the Compound 76 (30 mg/kg) treated group.
Figure 2B:
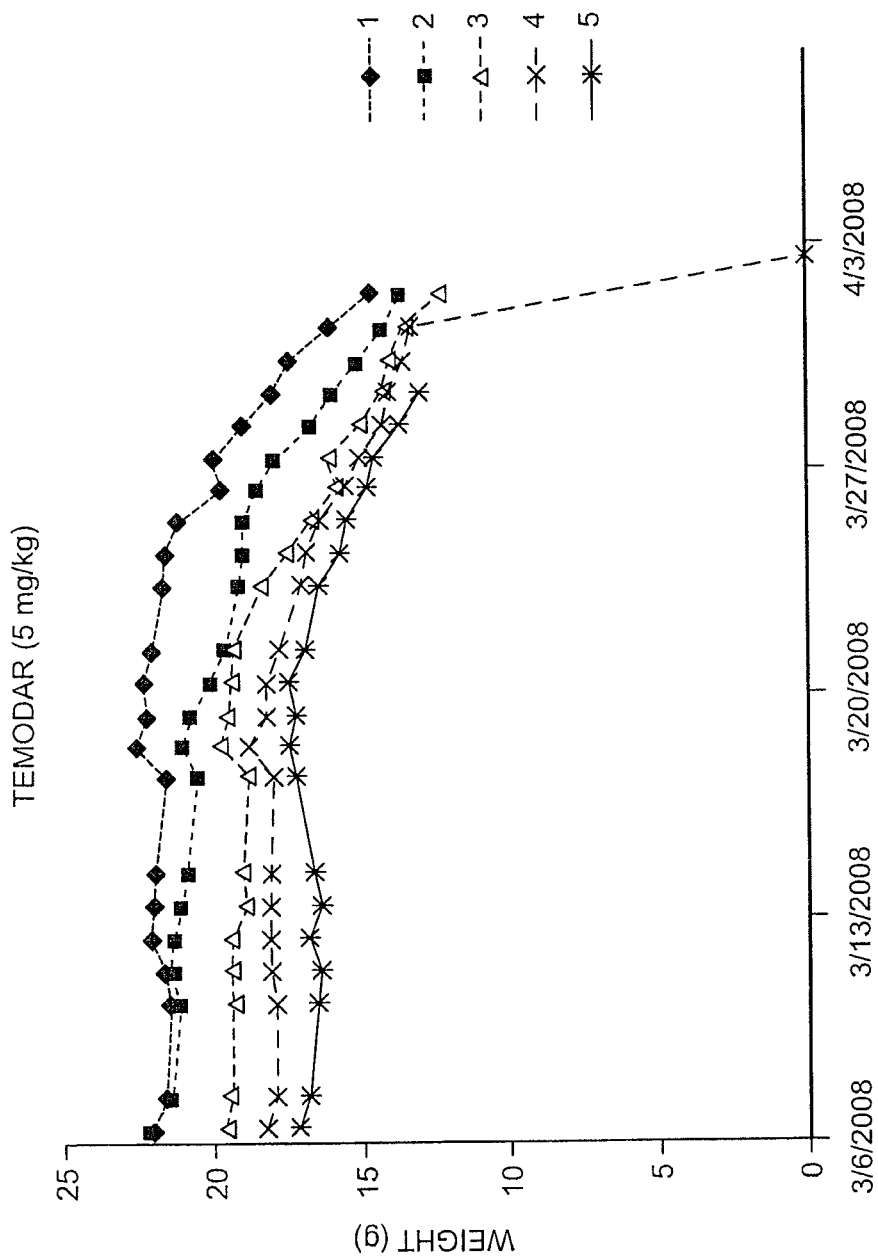
Figure 2C:
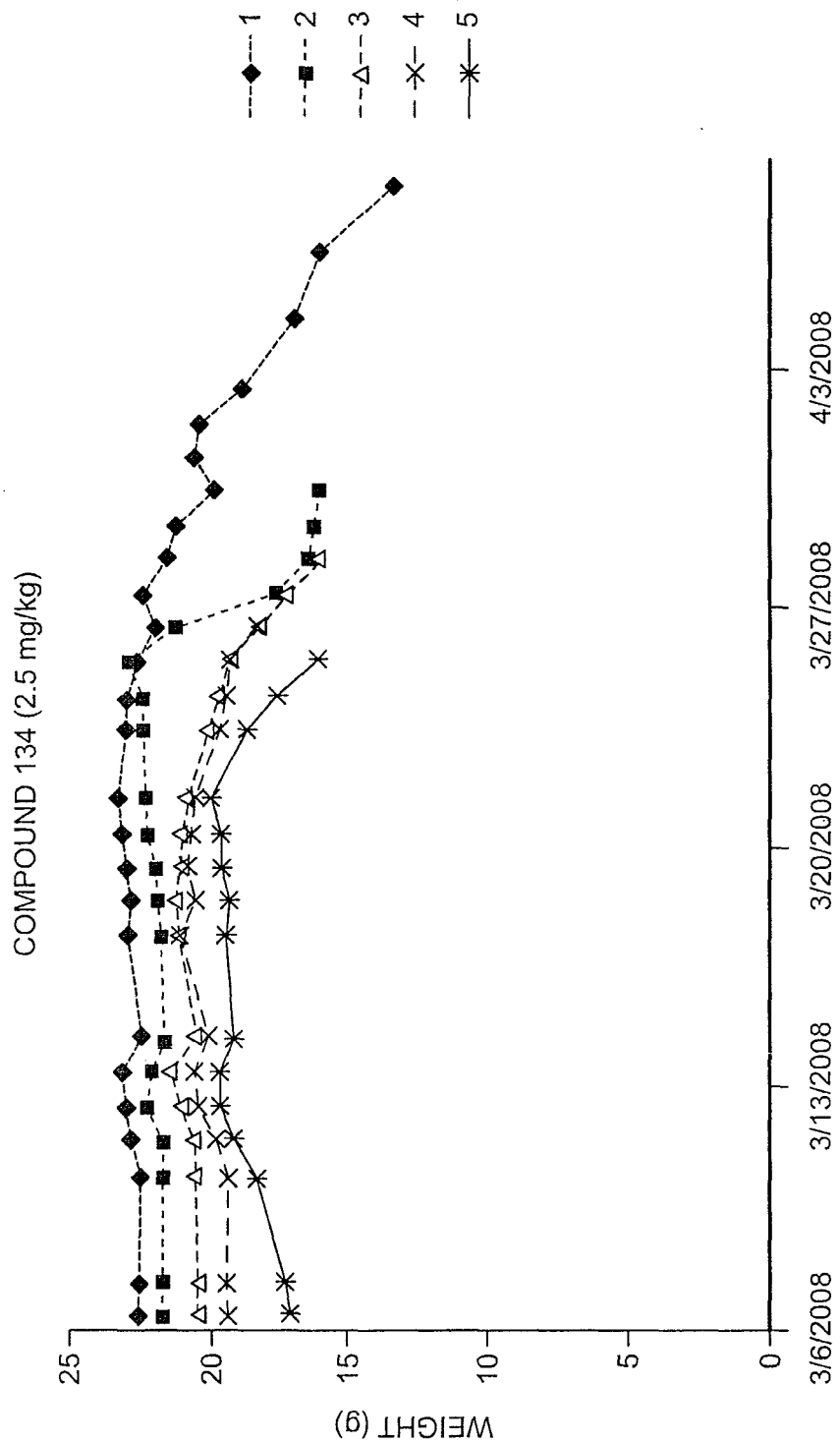
Figure 2D:
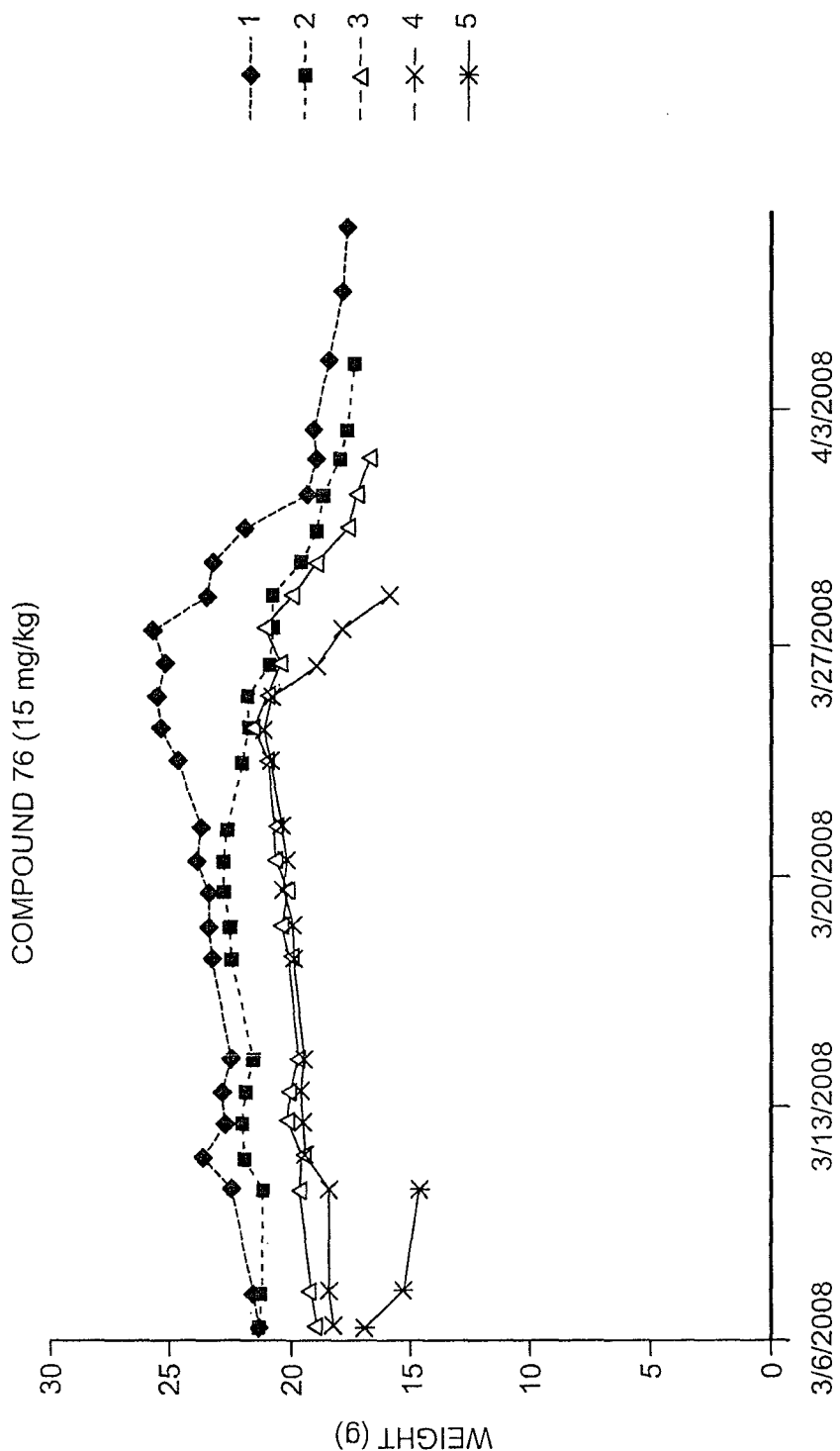
Figure 2E:
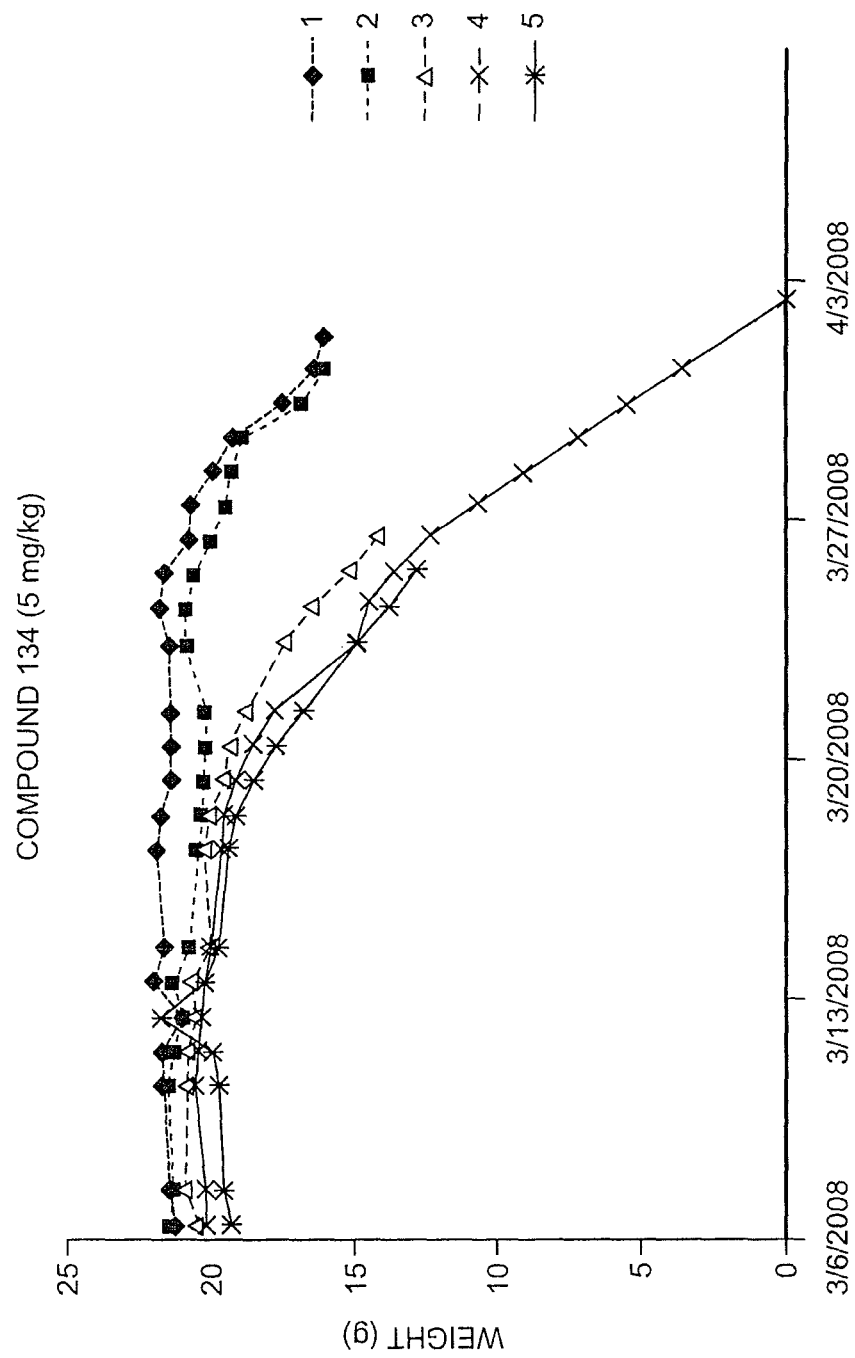
Figure 2F:
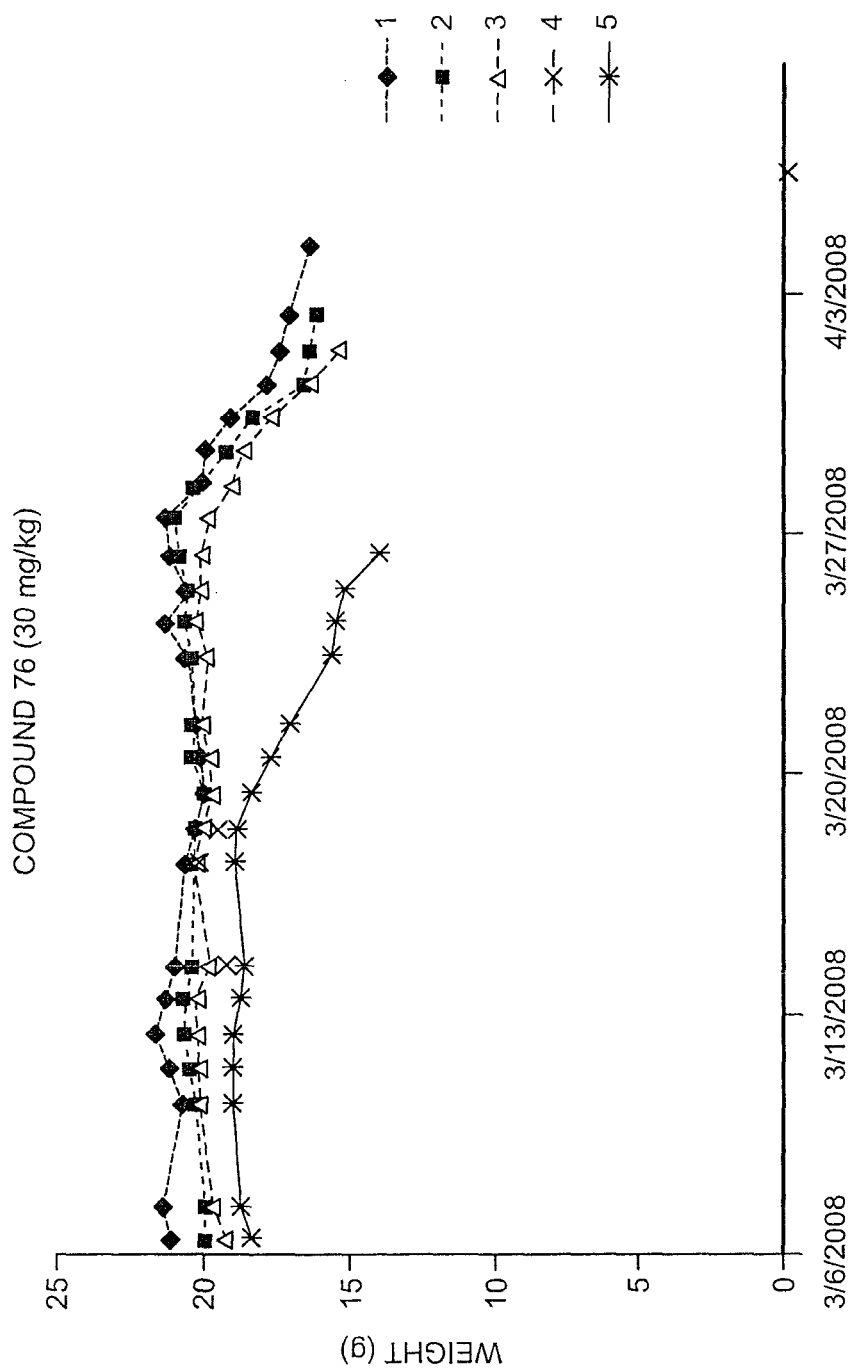

The present invention provides pharmaceutical compositions containing compounds of the invention and various uses of the disclosed compounds.

1. Pharmaceutical Compositions

The invention provides for a pharmaceutical composition comprising a compound according to Formula IB, I, IA, II, III, IV, V, VI, VII, VIII, IX, X, XI, XII, or XIII.

The invention provides a pharmaceutical composition comprising a compound according to Formula IB:

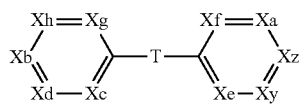

(Formula IB)

or a pharmaceutically acceptable salt, solvate, hydrate, or prodrug thereof, where the compound is present in an amount from 50 mg to 500 mg in the composition and wherein:

T is a bond;
$X_y$ is CY, N, or N—O;
$X_z$ is CZ;
Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;
$X_a$ is $CR_a$, N, or N—O;
$X_b$ is $CR_b$, N, or N—O;
$X_c$ is $CR_c$, N, or N—O;
$X_d$ is $CR_d$, N, or N—O;
$X_e$ is $CR_e$, N, or N—O;
$X_f$ is $CR_4$, N, or N—O;
$X_g$ is $CR_5$, N, or N—O;
$X_h$ is $CR_6$, N, or N—O;
$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

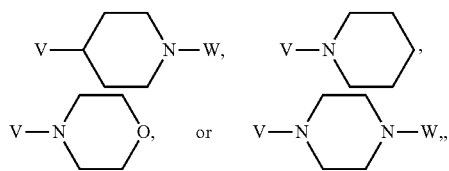

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;
P is $SO_3H$, $OSO_3H$, $PO_3H_2$, $OPO_3H_2$, $NH_2$, $NHR_{19}$, $NR_{20}R_{21}$,

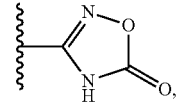 [SMILES: *c1noc(=O)[nH]1]

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower alkyl is linear or branched alkyl;
K is aryl, heteroaryl, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

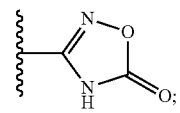 [SMILES: *c1noc(=O)[nH]1]

L is aryl, heteroaryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

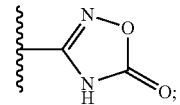 [SMILES: *c1noc(=O)[nH]1]

M is aryl, heteroaryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

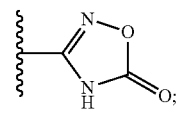 [SMILES: *c1noc(=O)[nH]1]

Q is aryl, heteroaryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

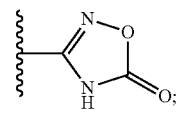 [SMILES: *c1noc(=O)[nH]1]

$R_{19}$, $R_{20}$ and $R_{21}$ are $C_1$, $C_2$, $C_3$, $C_4$, $C_5$, or $C_6$ alkyl or $R_{19}$ and $R_{20}$ taken together with the attached nitrogen atom form a five membered ring;
V is a bond, —$CH_2$—, —$CH_2CH_2$—, —$CH_2CH_2CH_2$—, —O—$CH_2$—, —$OCH_2CH_2$— or —$OCH_2CH_2CH_2$—;
Z is $(CHR_1)_n$—C(O)—$NR_2(CHR_3)_m$—Ar, where Ar is a substituted or unsubstituted aryl or nitrogen-containing heteroaryl group, $R_1$, $R_2$, and $R_3$ are independently H or $C_1$, $C_2$, $C_3$, $C_4$, $C_5$, or $C_6$ alkyl; and
n and m are independently 0, 1, or 2.

In one embodiment, the invention provides the pharmaceutical composition comprising a compound according to formula IB, wherein Z is

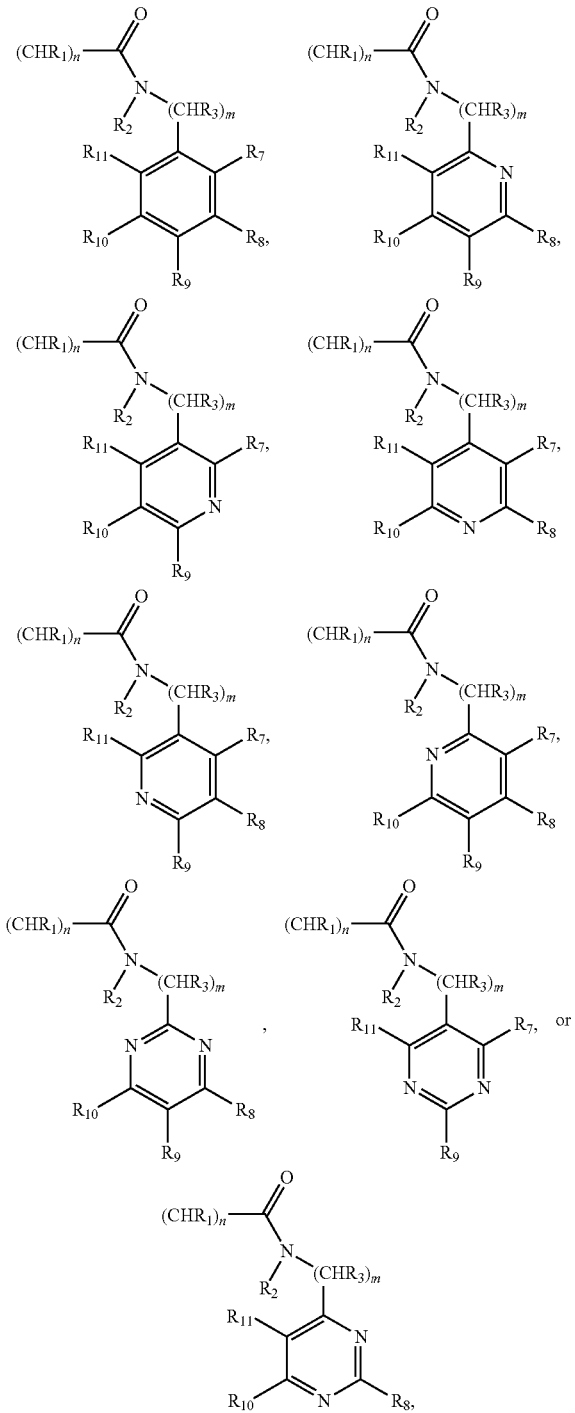

where
R$_1$, R$_2$, and R$_3$ are independently H or C$_1$, C$_2$, C$_3$, C$_4$, C$_5$, or C$_6$ alkyl;
n and m are, independently 0, 1, or 2;
R$_7$, R$_8$, R$_9$, R$_{10}$, and R$_{11}$ are, independently, hydrogen, hydroxyl, halogen, P, C$_1$, C$_2$, C$_3$, C$_4$, C$_5$, or C$_6$ alkyl, C$_1$, C$_2$, C$_3$, C$_4$, C$_5$, or C$_6$ alkoxy, O-lower (C$_1$, C$_2$, C$_3$, C$_4$, C$_5$, or C$_6$) alkyl-aryl, O-benzyl, C$_1$, C$_2$, C$_3$, C$_4$, C$_5$, or C$_6$ alkyl-OH, COOH, COO-lower (C$_1$, C$_2$, C$_3$, C$_4$, C$_5$, or C$_6$) alkyl, SO$_2$H, SO$_2$-lower (C$_1$, C$_2$, C$_3$, C$_4$, C$_5$, or C$_6$) alkyl,

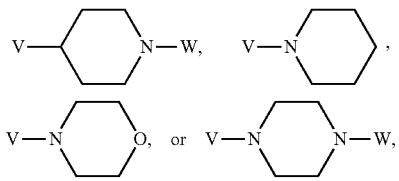

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl;
P is SO$_3$H, OSO$_3$H, PO$_3$H$_2$, OPO$_3$H$_2$, NH$_2$, NHR$_{19}$, NR$_{20}$R$_{21}$,

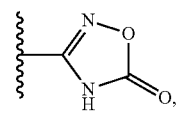 [SMILES: *c1noc(=O)[nH]1]

tetrazole, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q, further wherein lower (C$_1$, C$_2$, C$_3$, C$_4$, C$_5$, or C$_6$) alkyl is linear or branched alkyl;

K is aryl, heteroaryl, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

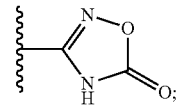 [SMILES: *c1noc(=O)[nH]1]

L is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

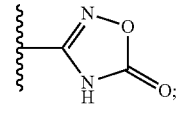 [SMILES: *c1noc(=O)[nH]1]

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

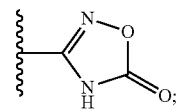 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

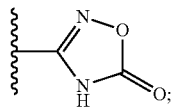

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring; and V is a bond, —$CH_2$—, —$CH_2CH_2$—, —$CH_2CH_2CH_2$—, —O—$CH_2$—, —$OCH_2CH_2$—, or —$OCH_2CH_2CH_2$—.

In one embodiment, the invention provides the pharmaceutical composition, wherein m is 1.

In one embodiment, the invention provides the pharmaceutical composition, wherein n is 1.

In one embodiment, the invention provides the pharmaceutical composition according to Formula IB, wherein at least one of $X_a$, $X_b$, $X_c$, $X_d$, $X_e$, $X_f$, $X_g$, $X_h$, and $X_y$ is N.

In one embodiment, the invention provides a pharmaceutical composition, wherein $X_a$ is N. In one embodiment, the invention provides the pharmaceutical composition, wherein $X_b$ is N. In one embodiment, the invention provides the pharmaceutical composition, wherein $X_c$ is N. In one embodiment, the invention provides the pharmaceutical composition, wherein $X_d$ is N. In one embodiment, the invention provides the pharmaceutical composition, wherein $X_e$ is N. In one embodiment, the invention provides the pharmaceutical composition, wherein $X_f$ is N. In one embodiment, the invention provides the pharmaceutical composition, wherein $X_g$ is N. In one embodiment, the invention provides the pharmaceutical composition, wherein $X_h$ is N.

In one embodiment, the invention provides the pharmaceutical composition according to formula IB, wherein $X_a$ and $X_y$ are each N. In one embodiment, the invention provides the pharmaceutical composition, wherein $X_e$ and $X_f$ are each N. In one embodiment, the invention provides the pharmaceutical composition, wherein $X_c$ and $X_g$ are each N. In one embodiment, the invention provides the pharmaceutical composition, wherein $X_d$ and $X_h$ are each N.

In one embodiment, the invention provides the pharmaceutical composition, wherein each of $X_e$, $X_f$, $X_c$ and $X_g$ is N.

In one embodiment, the invention provides the pharmaceutical composition wherein, $R_a$, $R_b$, $R_c$, $R_d$, $R_e$, $R_4$, $R_5$, and $R_6$ are not P.

In another embodiment, the invention provides a pharmaceutical composition, wherein $X_z$ is CZ and Z is

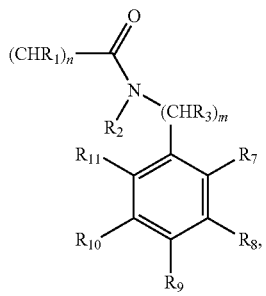

where $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

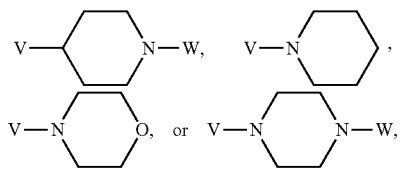

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl.

In another embodiment, the invention provides a pharmaceutical composition, wherein $X_f$ is $CR_4$, $X_g$ is $CR_5$, and $X_h$ is $CR_6$.

In another embodiment, the invention provides a pharmaceutical composition, wherein $R_4$, $R_5$ and $R_6$ are each H.

In another embodiment, the invention provides a pharmaceutical composition, wherein at least one of $R_7$, $R_8$, $R_9$, $R_{10}$ and $R_{11}$ is halogen, $C_1$, $C_2$, $C_3$, $C_4$, $C_5$, or $C_6$ alkyl, or O-benzyl.

In another embodiment, the invention provides the pharmaceutical composition, wherein m and n are each 1 and $R_2$ and $R_3$ are each H.

In another embodiment, the invention provides the pharmaceutical composition, wherein $R_h$ is not hydrogen.

In another embodiment, the invention provides the pharmaceutical composition, wherein the compound is selected from

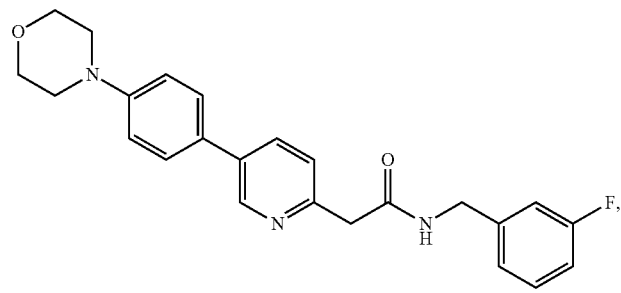 [SMILES: O=C(Cc1ccc(-c2ccc(N3CCOCC3)cc2)cn1)NCc1cccc(F)c1]

-continued
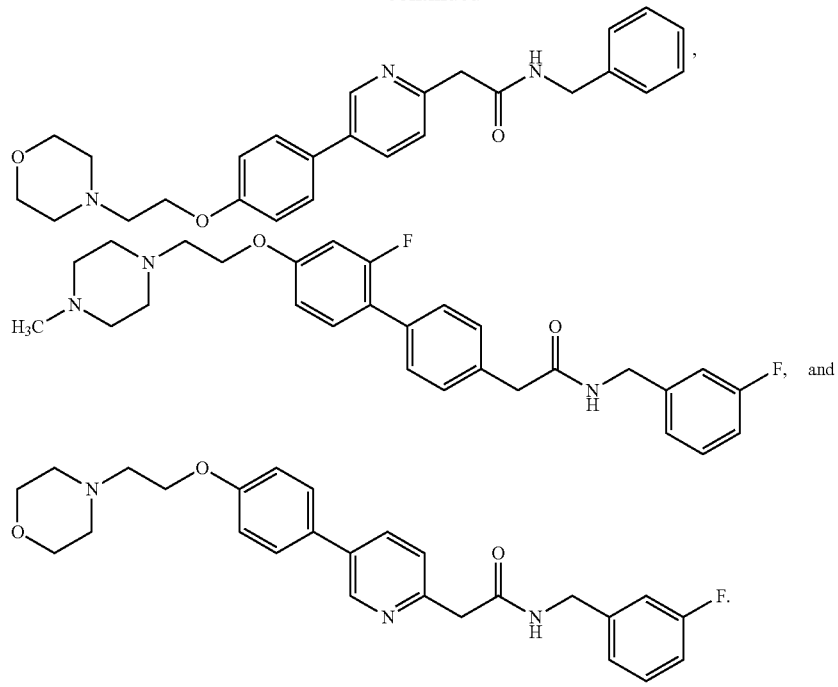
In another embodiment, the invention provides the pharmaceutical composition, wherein the compound is selected from
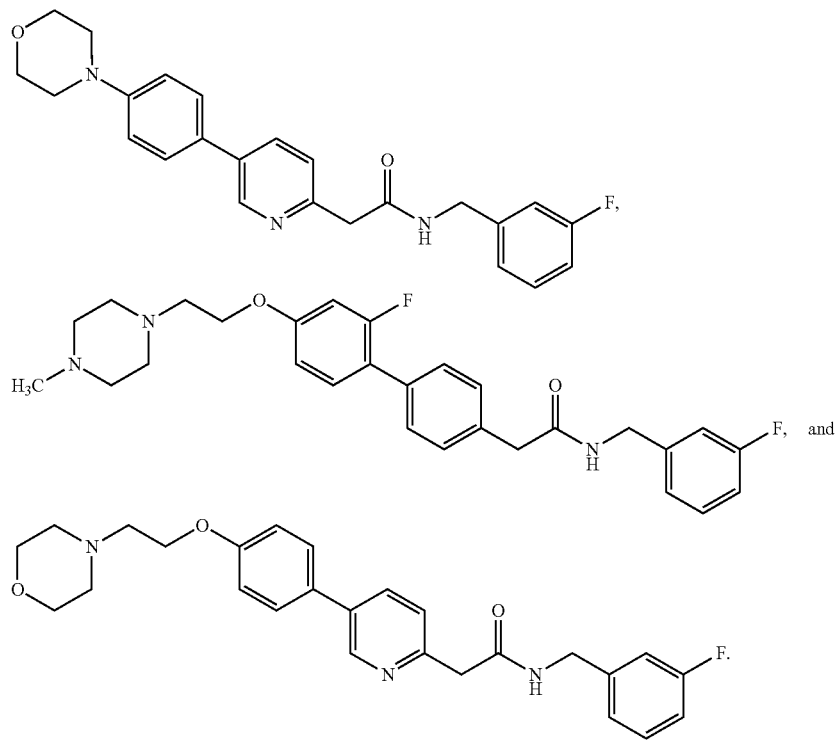
In another embodiment, the invention provides the pharmaceutical composition, wherein the compound is (Compound 76)

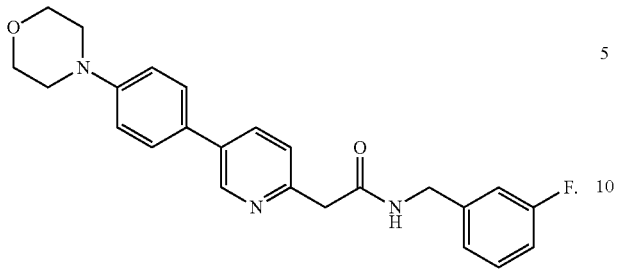

In another embodiment, the invention provides the pharmaceutical composition, wherein the compound is not (Compound 134)

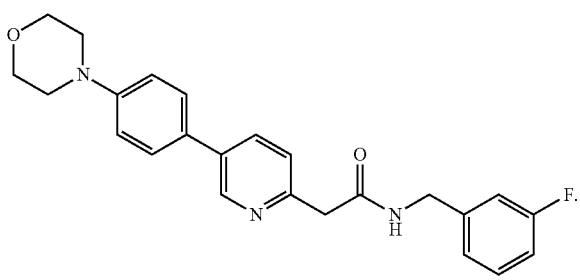 [SMILES: O=C(Cc1ccc(-c2ccc(N3CCOCC3)cc2)cn1)NCc1cccc(F)c1]

The pharmaceutical composition is formulated for oral, intravenous, intramuscular, or subcutaneous administration. Preferably, the pharmaceutical composition is formulated for oral administration. The pharmaceutical composition can include at least one pharmaceutically acceptable excipient or carrier. The formulation can be a tablet or a capsule.

The compound of the invention can be present in an amount from about 50 mg to about 500 mg (or any integer within said range (e.g., 50, 51, 52, ...)). Preferably, the compound of the invention can be present in an amount from about 100 mg to about 400 mg. Preferably, the compound of the invention can be present in an amount from about 200 mg to about 300 mg. More preferably, the compound of the invention can be present in an amount about 250 mg. More preferably, the compound of the invention can be present in an amount 250 mg. The compound of the invention can be present in an amount of 50 mg, 60 mg, 70 mg, 75 mg, 80 mg, 90 mg, 100 mg, 125 mg, 150 mg, 175 mg, 200 mg, 225 mg or 250 mg. The compound of the invention can be present in an amount of 250 mg, 275 mg, 300 mg, 325 mg, 350 mg, 375 mg, 400 mg, 425 mg, 450 mg, or 500 mg.

In one embodiment, the compound of the invention is administered up to four times daily (per 24 hour period). In one embodiment, the compound of the invention is administered twice daily (per 24 hour period). In a preferred embodiment, the compound of the invention is administered once daily (per 24 hour period).

Preferably, the compound is

The invention provides for a pharmaceutical composition comprising a compound according to Formula I:

(Formula I)

$$X_b \underset{X_d—X_c}{\overset{X_h=X_g}{\diagup}} —T— \underset{X_e—X_y}{\overset{X_f=X_a}{\diagdown}} X_z$$

or a pharmaceutically acceptable salt, solvate, hydrate, or prodrug thereof, where the compound is present in an amount from 50 mg to 500 mg in the composition and wherein:

T is a bond, $CR_{12}R_{13}$, $C(O)$, O, S, $S(O)$, $S(O)_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$ or N, or N—O;

$X_b$ is $CR_b$, N, or N—O;

$X_c$ is $CR_c$ or N, or N—O;

$X_d$ is $CR_d$ or N, or N—O;

$X_e$ is $CR_e$, N, or N—O;

$X_f$ is $CR_4$, N or N—O;

$X_g$ is $CR_5$, N, or N—O;

$X_h$ is $CR_6$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

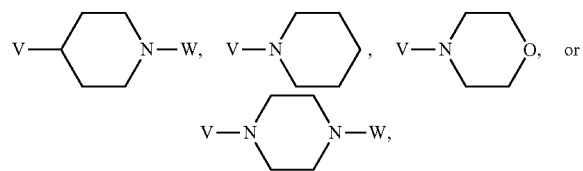

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $PO_3H_2$, $OPO_3H_2$, $NH_2$, $NHR_{19}$, $NR_{20}R_{21}$,

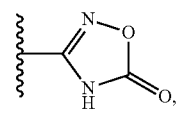

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower alkyl is linear or branched alkyl;

K is aryl, heteroaryl, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

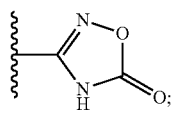 [SMILES: *c1noc(=O)[nH]1]

L is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

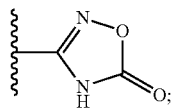

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

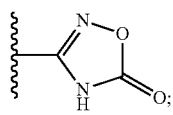 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

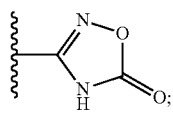 [SMILES: *c1noc(=O)[nH]1]

R$_{19}$, R$_{20}$ and R$_{21}$ are C$_1$, C$_2$, C$_3$, C$_4$, C$_5$, or C$_6$ alkyl or R$_{19}$ and R$_{20}$ taken together with the attached nitrogen atom form a five membered ring;

V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

R$_{12}$, R$_{13}$, R$_{14}$, R$_{15}$, R$_{16}$, R$_{17}$, and R$_{18}$, are, independently, H or C$_1$, C$_2$, C$_3$, C$_4$, C$_5$, or C$_6$ alkyl;

Z is (CHR$_1$)$_n$—C(O)—NR$_2$(CHR$_3$)$_m$—Ar, where Ar is a substituted or unsubstituted aryl or nitrogen-containing heteroaryl group, R$_1$, R$_2$, and R$_3$ are independently H or C$_1$, C$_2$, C$_3$, C$_4$, C$_5$, or C$_6$ alkyl; and n and m are independently 0, 1, or 2.

In one embodiment, the invention provides the pharmaceutical composition of Formula I, wherein m is 1.

In one embodiment, the invention provides the pharmaceutical composition of Formula I, wherein n is 1.

In another embodiment, the invention provides the pharmaceutical composition of Formula I, wherein R$_b$ is not hydrogen.

In one embodiment, the invention provides the pharmaceutical composition, wherein X$_a$ is N. In one embodiment, the invention provides the pharmaceutical composition, wherein X$_b$ is N. In one embodiment, the invention provides the pharmaceutical composition, wherein X$_c$ is N. In one embodiment, the invention provides the pharmaceutical composition, wherein X$_d$ is N. In one embodiment, the invention provides the pharmaceutical composition, wherein X$_e$ is N. In one embodiment, the invention provides the pharmaceutical composition, wherein X$_f$ is N. In one embodiment, the invention provides the pharmaceutical composition, wherein X$_g$ is N. In one embodiment, the invention provides the pharmaceutical composition, wherein X$_h$ is N.

In one embodiment, the invention provides the pharmaceutical composition, wherein X$_a$ and X$_y$ are each N. In one embodiment, the invention provides the pharmaceutical composition, wherein X$_e$ and X$_f$ are each N. In one embodiment, the invention provides the pharmaceutical composition, wherein X$_c$ and X$_g$ are each N. In one embodiment, the invention provides the pharmaceutical composition, wherein X$_d$ and X$_h$ are each N.

In one embodiment, the invention provides the pharmaceutical composition, wherein each of X$_e$, X$_f$, X$_c$ and X$_g$ is N.

In one embodiment, the invention provides the pharmaceutical composition wherein, R$_a$, R$_b$, R$_c$, R$_d$, R$_e$, R$_4$, R$_5$, and R$_6$ are not P.

In another embodiment, the invention provides the pharmaceutical composition, wherein the compound is selected from

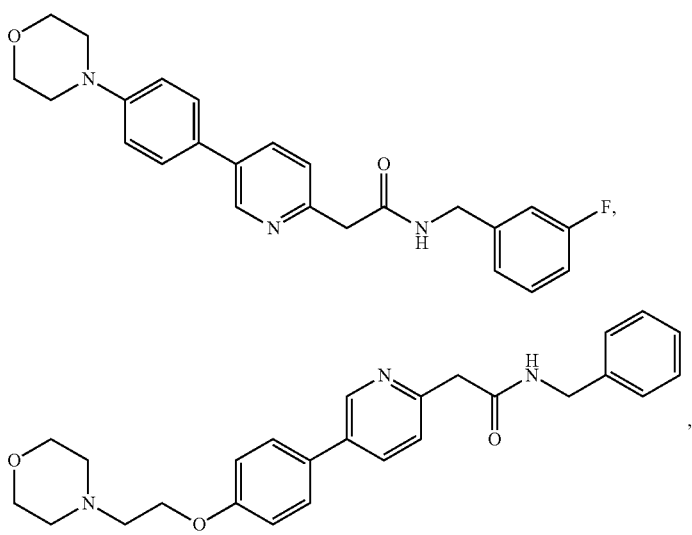

-continued
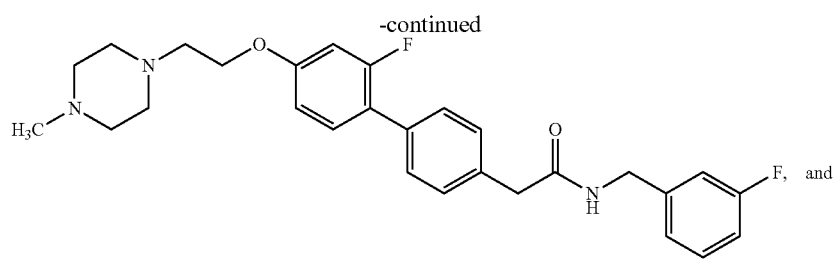
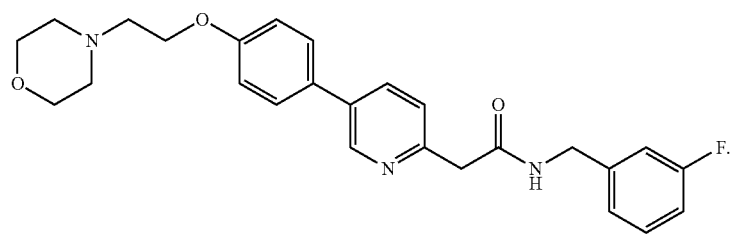
In another embodiment, the invention provides the pharmaceutical composition, wherein the compound is selected from
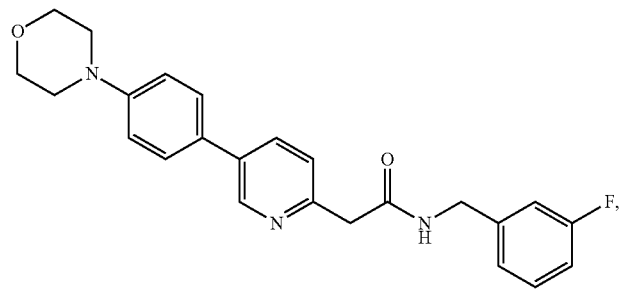
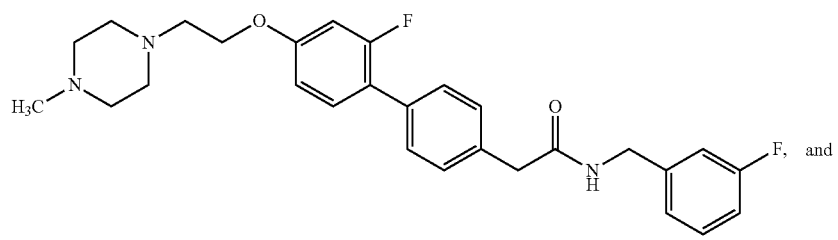
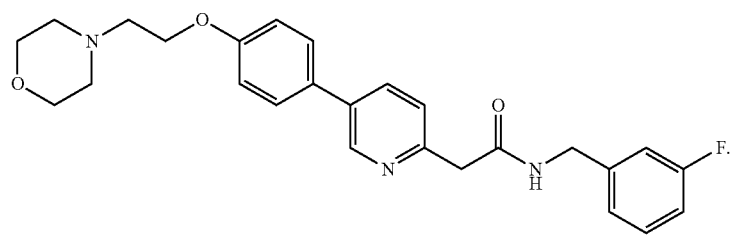
In another embodiment, the invention provides the pharmaceutical composition, wherein the compound is (Compound 76)

The pharmaceutical composition is formulated for oral, intravenous, intramuscular, or subcutaneous administration. Preferably, the pharmaceutical composition is formulated for oral administration. The pharmaceutical composition can include at least one pharmaceutically acceptable excipient or carrier.

The compound of Formula I can be present in an amount from about 50 mg to about 500 mg (or any integer with said range (e.g., 50, 51, 52, . . . )). Preferably, the compound of the invention can be present in an amount from about 100 mg to about 400 mg. Preferably, the compound of the invention can be present in an amount from about 200 mg to about 300 mg. More preferably, the compound of the invention can be present in an amount about 250 mg. More preferably, the compound of the invention can be present in an amount 250 mg. The compound of the invention can be present in an amount of 50 mg, 60 mg, 70 mg, 75 mg, 80 mg, 90 mg, 100 mg, 125 mg, 150 mg, 175 mg, 200 mg, 225 mg or 250 mg. The compound of the invention can be present in an amount of 250 mg, 275 mg, 300 mg, 325 mg, 350 mg, 375 mg, 400 mg, 425 mg, 450 mg, or 500 mg.

In one embodiment, the compounds of the invention are administered up to four times daily (per 24 hour period). In one embodiment, the compounds of the invention are administered twice daily (per 24 hour period). In a preferred embodiment, the compounds of the invention are administered once daily (per 24 hour period).

Preferably, the compound is

The invention provides for a pharmaceutical composition comprising a compound according to Formula IA:

(Formula IA)

wherein: T is absent (i.e., the rings are connected by a bond), $CR_{12}R_{13}$, C(O), O, S, S(O), $S(O)_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$X_f$ is $CR_4$, N or N—O;

$X_g$ is $CR_5$, N, or N—O;

$X_h$ is $CR_6$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl, wherein W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $PO_3H_2$, $OPO_3H_2$, $NH_2$, $NHR_{19}$, $NR_{20}R_{21}$, tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is aryl, heteroaryl, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or L is aryl, heteroaryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

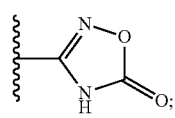 [SMILES: *c1noc(=O)[nH]1]

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

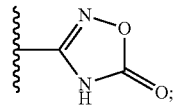 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

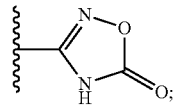 [SMILES: *c1noc(=O)[nH]1]

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring;

V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

R$_{12}$, R$_{13}$, R$_{14}$, R$_{15}$, R$_{16}$, R$_{17}$, and R$_{18}$, are, independently, H or C$_1$, C$_2$, C$_3$, C$_4$, C$_5$, or C$_6$ alkyl; and Z is (CHR$_1$)$_n$—C(O)—NR$_2$(CHR$_3$)$_m$—Ar, where Ar is a substituted or unsubstituted aryl or nitrogen-containing heteroaryl group, R$_1$, R$_2$, and R$_3$ are independently H or C$_1$, C$_2$, C$_3$, C$_4$, C$_5$, or C$_6$ alkyl; and n and m are, independently 0, 1, or 2;

provided that at least one of R$_a$, R$_b$, R$_c$, R$_d$, R$_e$, R$_4$, R$_5$, and R$_6$ is P.

The invention provides a pharmaceutical composition comprising a compound according to Formula I, IA, or IB, having a structure according to one of Formulae II, III, IV, V, VI, VII, VIII, IX, X, XI, XII, or XIII:

Formula II:

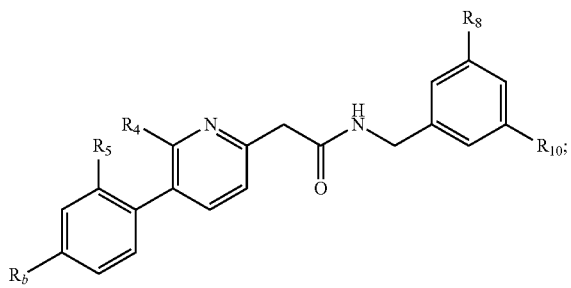

-continued

Formula III:

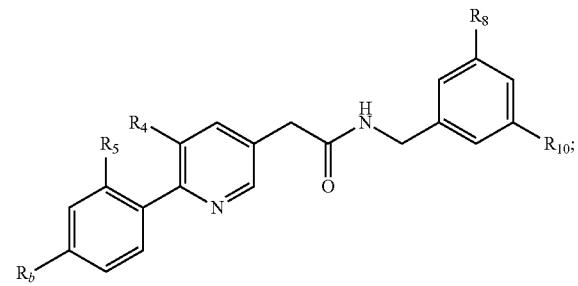

Formula IV:

Formula V:

Formula VI:

Formula VII:

-continued

Formula VIII:

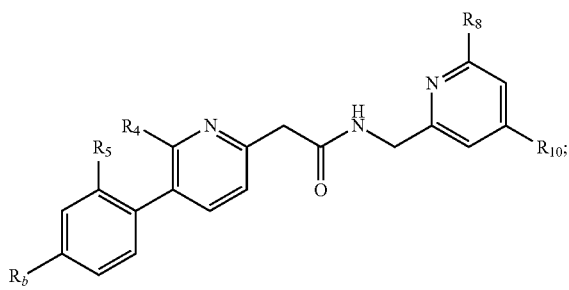

Formula IX:

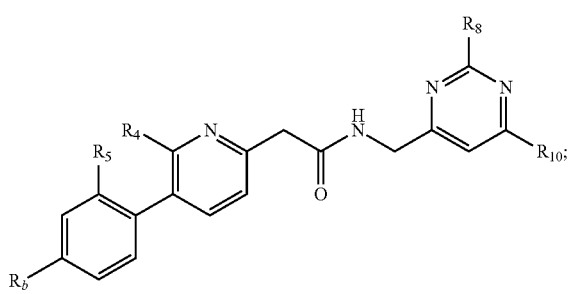

Formula X:

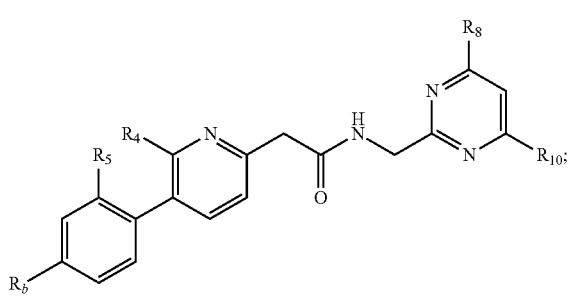

Formula XI:

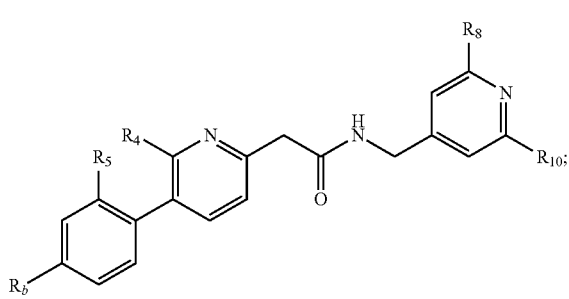

Formula XII:

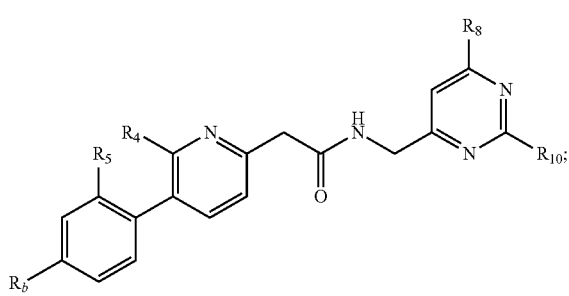

-continued

Formula XIII:

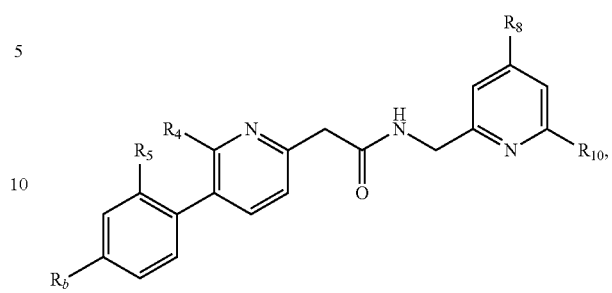

or a pharmaceutically acceptable salt, solvate, hydrate, or prodrug thereof, where: $R_b$, $R_4$, $R_5$, $R_8$, and $R_{10}$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

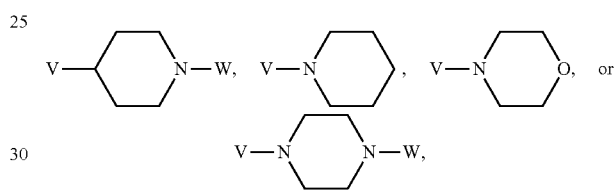

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $PO_3H_2$, $OPO_3H_2$, $NH_2$, $NHR_{19}$, $NR_{20}R_{21}$,

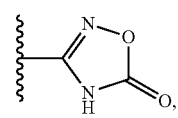

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is aryl, heteroaryl, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

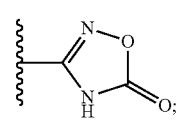 [SMILES: *c1noc(=O)[nH]1]

L is aryl, heteroaryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

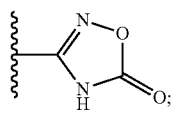 [SMILES: *c1noc(=O)[nH]1]

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

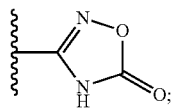 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

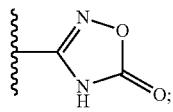 [SMILES: *c1noc(=O)[nH]1]

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—.

Formula II, III, IV, V, VI, VII, VIII, IX, X, XI, XII, XIII are within the scope of Formula I, IA, or IB.

The invention includes a solvate of a compound according to Formula I, IA, or IB.

The invention also includes a hydrate of a compound according to Formula I, IA, or IB.

The invention also includes an acid addition salt of a compound according to Formula I, IA, or IB. For example, a hydrochloride salt e.g., dihydrochloride.

The invention includes a mesylate salt of a compound according to Formula I, IA, or IB.

The invention also includes a prodrug of a compound according to Formula I, IA, or IB.

The invention also includes a pharmaceutically acceptable salt of a compound of Formula I, IA, or IB.

The invention also includes a composition of a compound according to Formula I, IA, or IB and at least one pharmaceutically acceptable excipient.

For example, in the compound of Formula II, III, IV, V, VI, VII, VIII, IX, X, XI, XII, and XIII, R$_8$ is hydrogen, F, Cl, Br, or I. For example, R$_8$ is F. In certain compounds, R$_8$ is H.

In certain compounds of Formula II, III, IV, V, VI, VII, VIII, IX, X, XI, XII, and XIII, R$_b$ is C$_1$, C$_2$, C$_3$, C$_4$, C$_5$, or C$_6$ alkoxy. For example, R$_b$ is methoxy or ethoxy.

In certain compounds of Formula II, III, IV, V, VI, VII, VIII, IX, X, XI, XII, and XIII, R$_b$ is hydrogen, Cl, Br, or I. In other compounds, in the compound of Formula II, III, IV, V, VI, VII, VIII, IX, X, XI, XII, and XIII, R$_b$ is

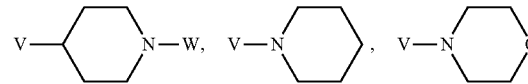

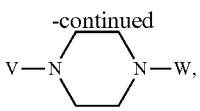

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl, and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—.

In certain compounds of Formula II, III, IV, V, VI, VII, VIII, IX, X, XI, XII, and XIII, R$_4$ is hydrogen, C$_1$, C$_2$, C$_3$, C$_4$, C$_5$, or C$_6$ alkoxy, F, Cl, Br, or I. In other compounds, in the compound of Formula II, III, IV, V, VI, VII, VIII, IX, X, XI, XII, and XIII, R$_4$ is

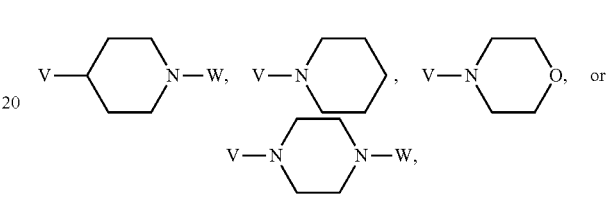

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—.

In certain compounds of Formula II, III, IV, V, VI, VII, VIII, IX, X, XI, XII, and XIII, R$_5$ is hydrogen, C$_1$, C$_2$, C$_3$, C$_4$, C$_5$, or C$_6$ alkoxy, F, Cl, Br, or I. In other compounds, in the compound of Formula II, III, IV, V, VI, VII, VIII, IX, X, XI, XII, and XIII, R$_5$ is

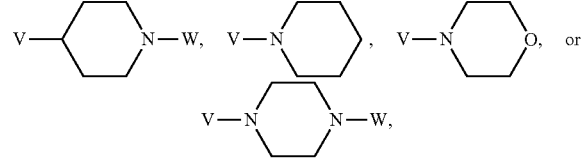

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—.

In certain compounds of Formula II, III, IV, V, VI, VII, VIII, IX, X, XI, XII, and XIII, R$_{10}$ is hydrogen, C$_1$, C$_2$, C$_3$, C$_4$, C$_5$, or C$_6$ alkoxy, F, Cl, Br, or I. For example, R$_{10}$ is methoxy, ethoxy or isobutoxy.

In other compounds of Formula II, III, IV, V, VI, VII, VIII, IX, X, XI, XII, and XIII, R$_{10}$ is

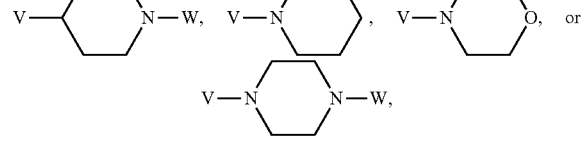

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl; and V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—.

For example, in the compound of Formula II, III, IV, V, VI, VII, VIII, IX, X, XI, XII, and XIII, W is hydrogen, or $C_1$, $C_2$, $C_3$, $C_4$, $C_5$, or $C_6$ alkyl.

Certain compounds of the invention include compounds according to Formula II.

The invention relates to a solvate of a compound according to one of Formulae II, III, IV, V, VI, VII, VIII, IX, X, XI, XII, and XIII. The invention also relates to a hydrate of a compound according to one of Formulae II, III, IV, V, VI, VII, VIII, IX, X, XI, XII, and XIII.

The invention also relates to an acid addition salt of a compound according to one of Formulae II, III, IV, V, VI, VII, VIII, IX, X, XI, XII, and XIII. For example, a hydrochloride salt.

Further, the invention relates to a prodrug of a compound according to one of Formulae II, III, IV, V, VI, VII, VIII, IX, X, XI, XII, and XIII.

The invention also relates to a pharmaceutically acceptable salt of a compound of one of Formulae II, III, IV, V, VI, VII, VIII, IX, X, XI, XII, and XIII.

The invention includes compositions comprising a compound according to one of Formulae I, II, III, IV, V, VI, VII, VIII, IX, X, XI, XII, and XIII and at least one pharmaceutically acceptable excipient.

In one embodiment of the invention in a compound of Formula I, at least one of $X_a$, $X_b$, $X_c$, $X_d$, $X_e$, $X_f$, $X_g$, $X_h$, $X_y$ and $X_z$ is N. In another embodiment, at least two of $X_a$, $X_b$, $X_c$, $X_d$, $X_e$, $X_f$, $X_g$, $X_h$, $X_y$, and $X_z$ are N. In another embodiment, at least one of $X_a$ and $X_y$ is N. For example, both $X_a$ and $X_y$ are N. In another embodiment, $X_a$, $X_b$, $X_c$, $X_d$, and $X_e$ are not each N or N—O. In another embodiment, $X_c$, $X_d$, and $X_e$ are not each N or N—O.

In one embodiment, $X_a$ is N. In one embodiment, $X_b$ is N. In one embodiment, $X_c$ is N. In one embodiment, $X_d$ is N. In one embodiment, $X_e$ is N. In one embodiment, $X_f$ is N. In one embodiment, $X_g$ is N. In one embodiment, $X_h$ is N.

In one embodiment, $X_a$ and $X_y$ are each N. In one embodiment, $X_e$ and $X_f$ are each N. In one embodiment, $X_c$ and $X_g$ are each N. In one embodiment, $X_d$ and $X_h$ are each N.

In one embodiment, $X_e$, $X_f$, $X_c$ and $X_g$ are each N.

In one embodiment, a compound of formula I has T as a bond. In another embodiment, $X_b$ is $CR_b$. In another embodiment, $R_b$ is P. For example, in one embodiment, P is O-lower ($C_1$, $C_2$, $C_3$, $C_4$, $C_5$, or $C_6$) alkyl-K. In one embodiment, lower ($C_1$, $C_2$, $C_3$, $C_4$, $C_5$, or $C_6$) alkyl is $CH_2CH_2CH_2$ In one embodiment, lower ($C_1$, $C_2$, $C_3$, $C_4$, $C_5$, or $C_6$) alkyl is branched alkyl. For example, branched alkyl is

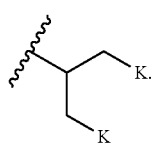

In another embodiment, K, L, M, or Q, if present, is lower $C_1$, $C_2$, $C_3$, $C_4$, $C_5$ or $C_6$ alkoxy. For example, K is methoxy. In one embodiment, branched alkyl is

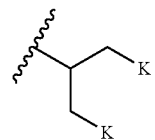

and K is methoxy. In another embodiment, K, L, M, or Q, if present, is COOH. For example, in one embodiment, K is COOH. In another embodiment, K, L, M, or Q, if present, is aryl or heteroaryl. For example, heteroaryl is tetrazole.

In one embodiment, $R_b$ is

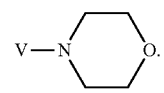

In another embodiment, $R_b$ is

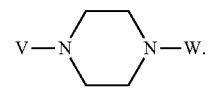

In one embodiment, V is —$OCH_2CH_2$. In another embodiment, V is a bond. In one embodiment, W is $C_1$, $C_2$, $C_3$, $C_4$, $C_5$, or $C_6$ alkyl. For example, W is methyl or ethyl.

In one embodiment, $X_z$ is CZ, further wherein Z is

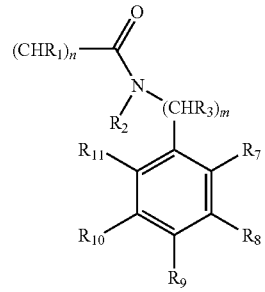

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

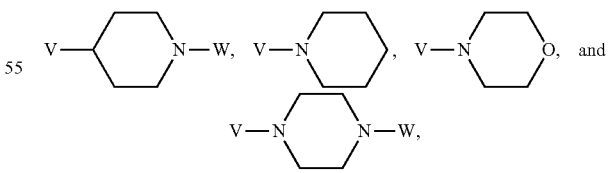

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl. In another embodiment, at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl. In another embodiment, at least one of $R_8$ or $R_{10}$ is halogen. For example, halogen is fluorine. In another embodiment, at least one of $R_7$ or $R_{11}$ is $C_1$, $C_2$, $C_3$, $C_4$, $C_5$, or $C_6$ alkoxy or O-benzyl. For example, at least one of $R_7$ or $R_{11}$ is ethoxy or at least one of $R_7$ or $R_{11}$ is O-benzyl. In one embodiment, $R_1$ is H. In one embodiment, n is 1. In one embodiment, $R_2$ is H. In one embodiment, $R_3$ is H. In one embodiment, m is 1. In another embodiment, m and n are each 1 and $R_2$ and $R_3$ are each H.

In one embodiment, $R_4$ and $R_6$ are each H. In another embodiment $R_5$ is selected from halogen and $C_1$, $C_2$, $C_3$, $C_4$, $C_5$, or $C_6$ alkyl. In one embodiment, $R_5$ is halogen. For example, $R_5$ is Cl or F. In another embodiment, $R_5$ is $C_1$, $C_2$, $C_3$, $C_4$, $C_5$, or $C_6$ alkyl. For example, $R_5$ is methyl or ethyl.

In one embodiment, at least one of $X_a$, $X_b$, $X_c$, $X_d$, $X_e$, $X_f$, $X_g$, $X_h$, $X_y$, and $X_z$ is N.

In another embodiment, $X_i$ is CZ, further wherein Z is

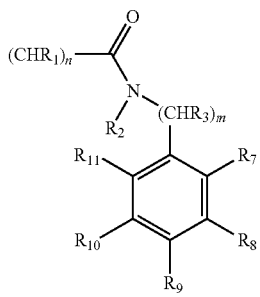

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl,

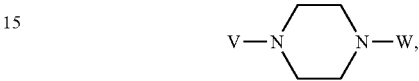

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl. In one embodiment, at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl. In another embodiment, m and n are each 1 and $R_2$ and $R_3$ are each H. In one embodiment, $R_4$ and $R_6$ are each H.

Certain compounds of the invention include compounds according to Formula II.

Compounds of the invention include those listed in Table 1:

TABLE 1

| Compound | Structure |
|---|---|
| 1 | 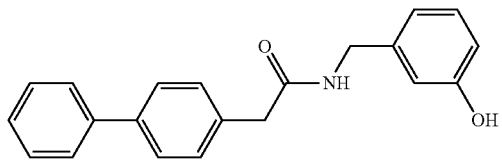 [SMILES: O=C(Cc1ccc(-c2ccccc2)cc1)NCc1cccc(O)c1] |
| 2 | 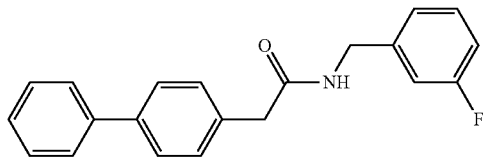 [SMILES: O=C(Cc1ccc(-c2ccccc2)cc1)NCc1cccc(F)c1] |
| 3 | 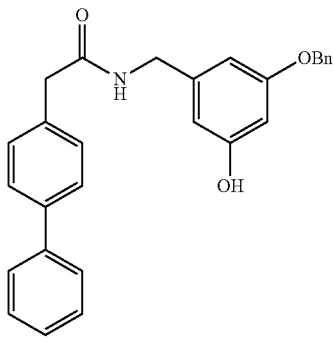 [SMILES: O=C(Cc1ccc(-c2ccccc2)cc1)NCc1cc(O)cc(OCc2ccccc2)c1] |

TABLE 1-continued

| Compound | Structure |
|---|---|
| 4 | *(structure: biphenyl-CH2-C(=O)-NH-CH2-(3-fluorophenyl))* |
| 5 | *(structure: 4-biphenyl-CH2-C(=O)-NH-(3-fluorophenyl))* |
| 6 | *(structure: 2'-fluoro-biphenyl-CH2-C(=O)-NH-CH2-(3-fluorophenyl))* |
| 7 | *(structure: 3'-fluoro-biphenyl-CH2-C(=O)-NH-CH2-(3-fluorophenyl))* |
| 8 | *(structure: 4'-fluoro-terphenyl-CH2-C(=O)-NH-CH2-(3-fluorophenyl))* |

TABLE 1-continued

| Compound | Structure |
|---|---|
| 9 | N-(3-fluorobenzyl)-N-methyl-2-(biphenyl-4-yl)acetamide |
| 10 | 2-(3-fluoro-4-phenylphenyl)-N-(3-fluorobenzyl)acetamide |
| 11 | N-(3-fluorobenzyl)-2-(6-phenylpyridin-3-yl)acetamide |
| 12 | N-(3-fluorobenzyl)-2-(4-(pyridin-2-yl)phenyl)acetamide |

TABLE 1-continued
| Compound | Structure |
|---|---|
| 13 | 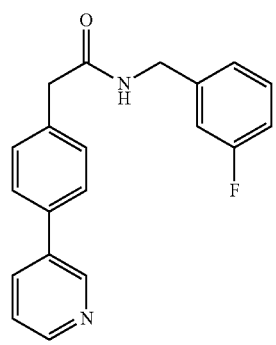 [SMILES: O=C(Cc1ccc(-c2cccnc2)cc1)NCc1cccc(F)c1] |
| 14 | 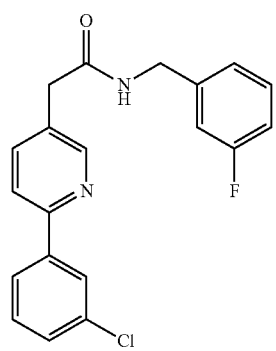 [SMILES: O=C(Cc1ccc(-c2cccc(Cl)c2)nc1)NCc1cccc(F)c1] |
| 15 | 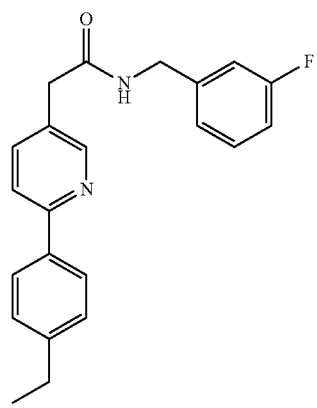 [SMILES: CCc1ccc(-c2ccc(CC(=O)NCc3cccc(F)c3)cn2)cc1] |
| 16 | 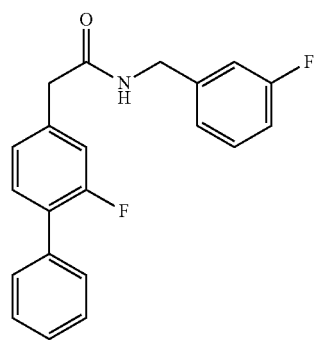 [SMILES: O=C(Cc1ccc(-c2ccccc2)c(F)c1)NCc1cccc(F)c1] |

TABLE 1-continued
| Compound | Structure |
|---|---|
| 17 | 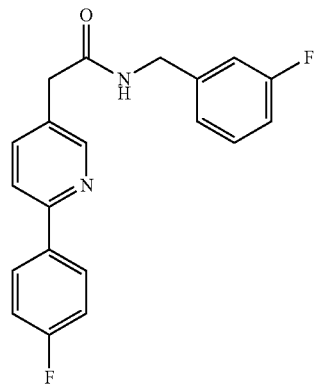 [SMILES: O=C(Cc1ccc(-c2ccc(F)cc2)nc1)NCc1cccc(F)c1] |
| 18 | 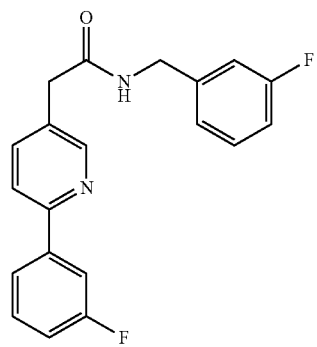 [SMILES: O=C(Cc1ccc(-c2cccc(F)c2)nc1)NCc1cccc(F)c1] |
| 19 | 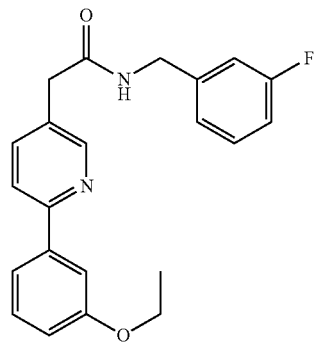 [SMILES: CCOc1cccc(-c2ccc(CC(=O)NCc3cccc(F)c3)cn2)c1] |
| 20 | 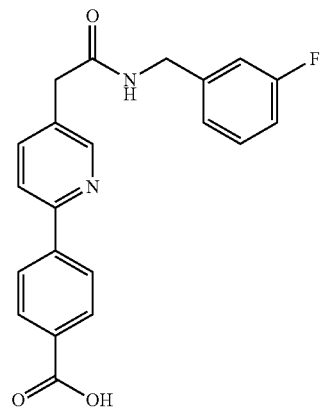 [SMILES: O=C(Cc1ccc(-c2ccc(C(=O)O)cc2)nc1)NCc1cccc(F)c1] |

TABLE 1-continued

| Compound | Structure |
|---|---|
| 21 | 2-(6-(2-ethoxyphenyl)pyridin-3-yl)-N-(3-fluorobenzyl)acetamide |
| 22 | 2-(6-(4-ethoxyphenyl)pyridin-3-yl)-N-(3-fluorobenzyl)acetamide |
| 23 | N-(3-fluorobenzyl)-2-(6-(4-(methylsulfonyl)phenyl)pyridin-3-yl)acetamide |
| 24 | N-(3-fluorobenzyl)-2-(4-(pyridin-4-yl)phenyl)acetamide |

TABLE 1-continued
| Compound | Structure |
|---|---|
| 25 | 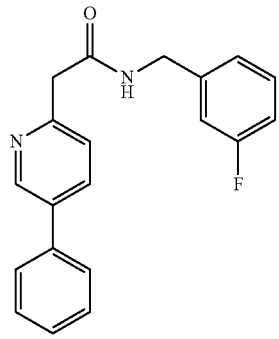 [SMILES: O=C(Cc1ccc(-c2ccccc2)cn1)NCc1cccc(F)c1] |
| 26 | 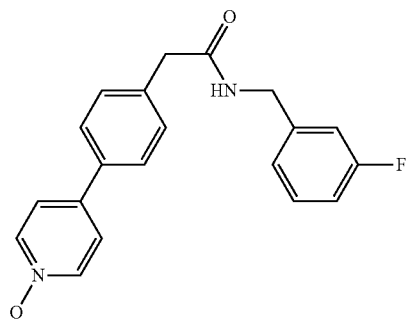 |
| 27 | 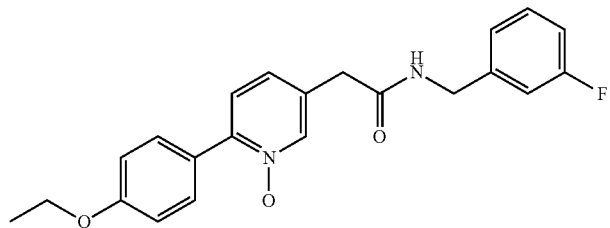 |
| 28 | 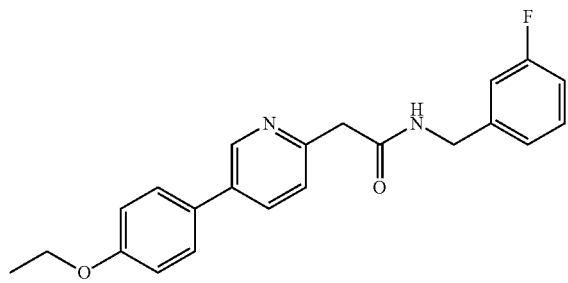 [SMILES: CCOc1ccc(-c2ccc(CC(=O)NCc3cccc(F)c3)nc2)cc1] |
| 29 | 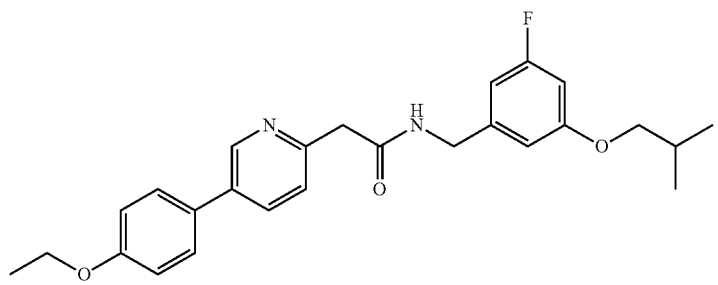 [SMILES: CCOc1ccc(-c2ccc(CC(=O)NCc3cc(F)cc(OCC(C)C)c3)nc2)cc1] |

TABLE 1-continued

| Compound | Structure |
|---|---|
| 30 | 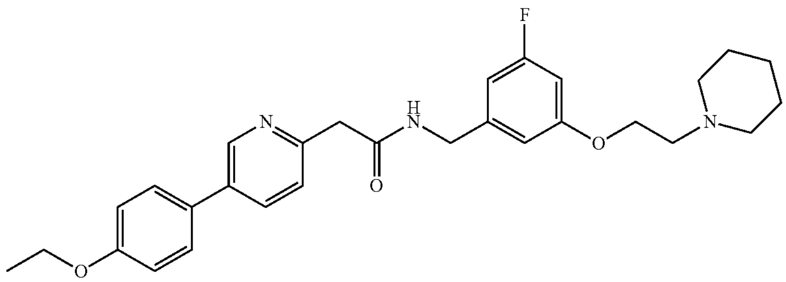 [SMILES: CCOc1ccc(-c2ccc(CC(=O)NCc3cc(F)cc(OCCN4CCCCC4)c3)nc2)cc1] |
| 31 | 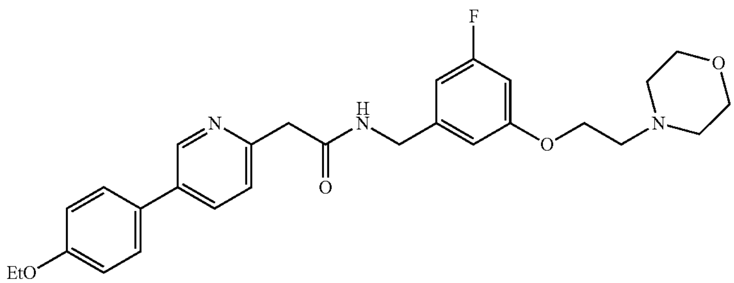 [SMILES: CCOc1ccc(-c2ccc(CC(=O)NCc3cc(F)cc(OCCN4CCOCC4)c3)nc2)cc1] |
| 32 | 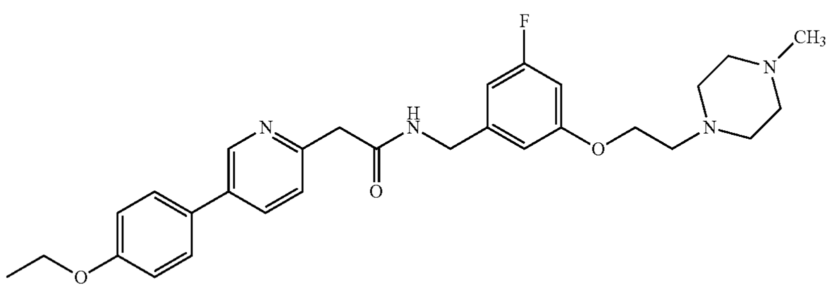 [SMILES: CCOc1ccc(-c2ccc(CC(=O)NCc3cc(F)cc(OCCN4CCN(C)CC4)c3)nc2)cc1] |
| 33 | 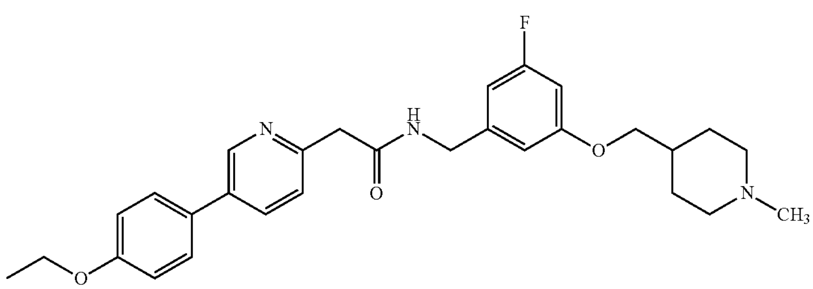 [SMILES: CCOc1ccc(-c2ccc(CC(=O)NCc3cc(F)cc(OCC4CCN(C)CC4)c3)nc2)cc1] |
| 34 | 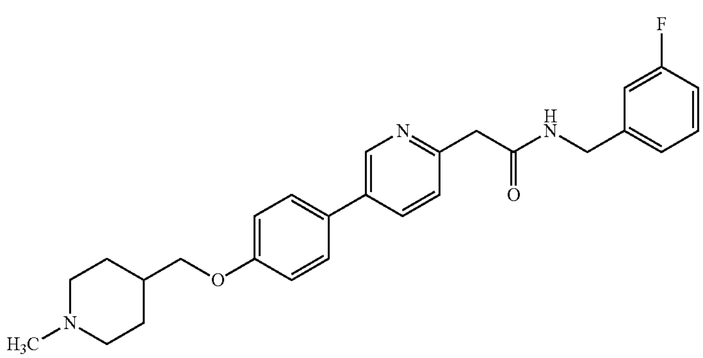 [SMILES: CN1CCC(COc2ccc(-c3ccc(CC(=O)NCc4cccc(F)c4)nc3)cc2)CC1] |

TABLE 1-continued
| Compound | Structure |
|---|---|
| 35 | 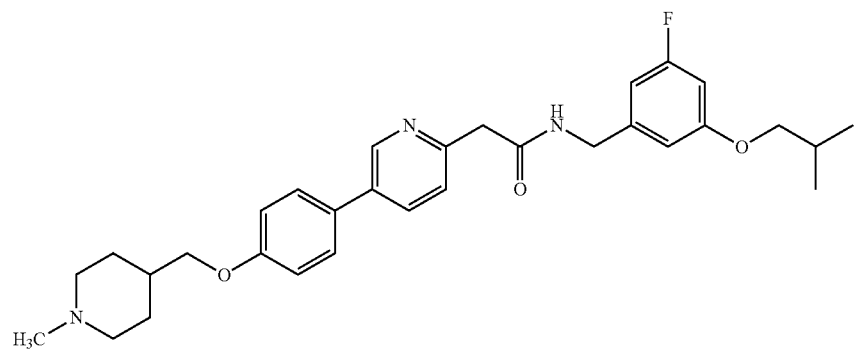 [SMILES: CC(C)COc1cc(F)cc(CNC(=O)Cc2ccc(-c3ccc(OCC4CCN(C)CC4)cc3)cn2)c1] |
| 36 | 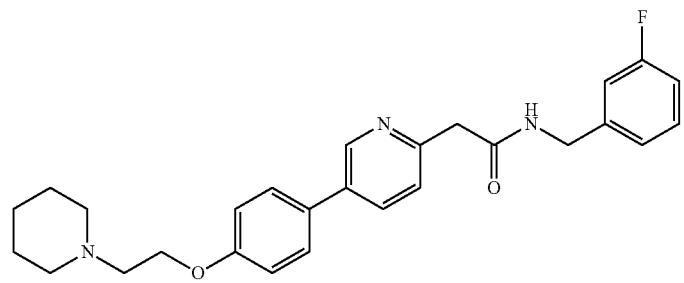 [SMILES: O=C(Cc1ccc(-c2ccc(OCCN3CCCCC3)cc2)cn1)NCc1cccc(F)c1] |
| 37 | 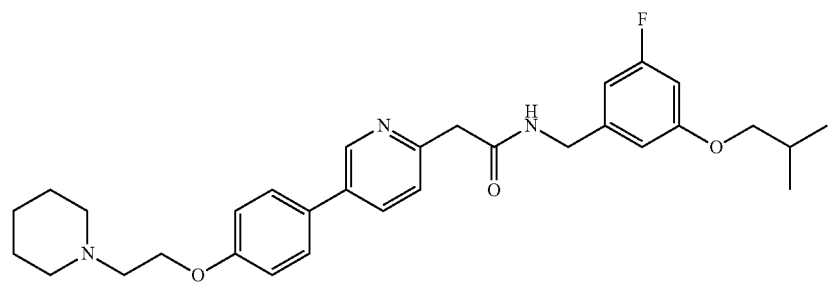 [SMILES: CC(C)COc1cc(F)cc(CNC(=O)Cc2ccc(-c3ccc(OCCN4CCCCC4)cc3)cn2)c1] |
| 38 | 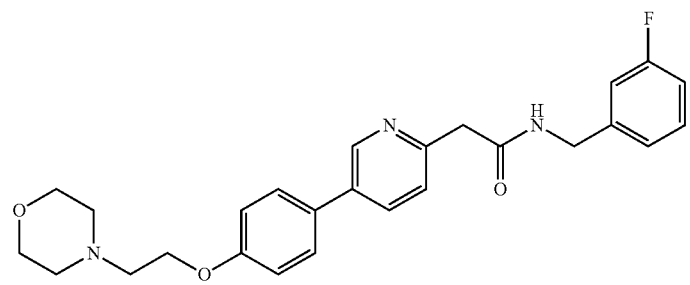 [SMILES: O=C(Cc1ccc(-c2ccc(OCCN3CCOCC3)cc2)cn1)NCc1cccc(F)c1] |
| 39 | 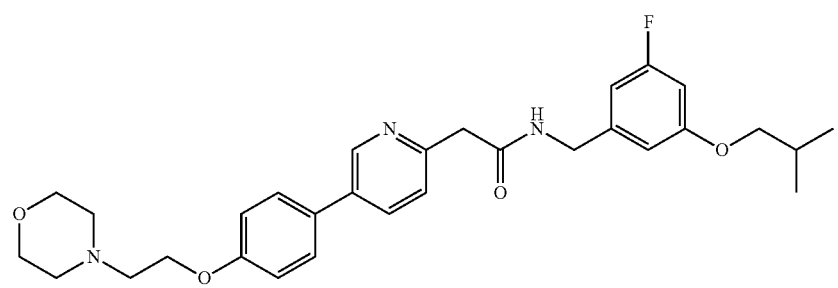 [SMILES: CC(C)COc1cc(F)cc(CNC(=O)Cc2ccc(-c3ccc(OCCN4CCOCC4)cc3)cn2)c1] |

TABLE 1-continued
| Compound | Structure |
|---|---|
| 40 | 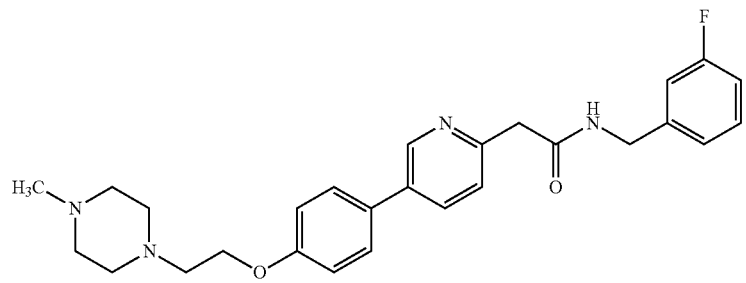 [SMILES: CN1CCN(CCOc2ccc(-c3ccc(CC(=O)NCc4cccc(F)c4)nc3)cc2)CC1] |
| 41 | 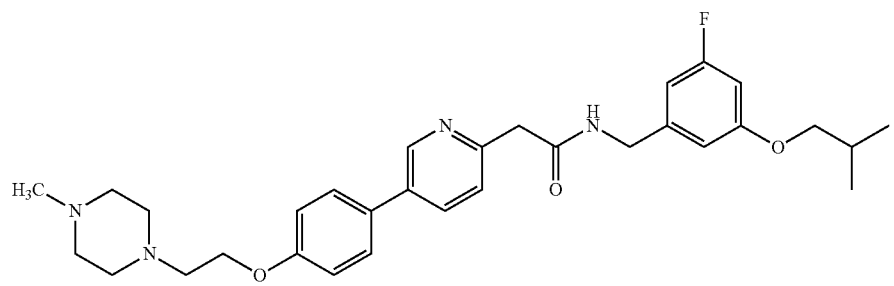 [SMILES: CC(C)COc1cc(F)cc(CNC(=O)Cc2ccc(-c3ccc(OCCN4CCN(C)CC4)cc3)cn2)c1] |
| 42 | 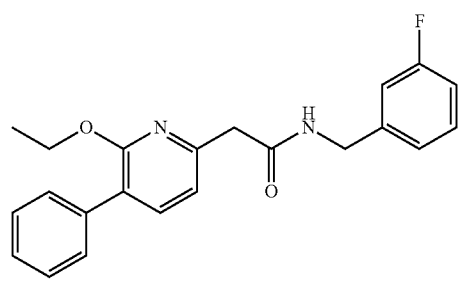 [SMILES: CCOc1nc(CC(=O)NCc2cccc(F)c2)ccc1-c1ccccc1] |
| 43 | 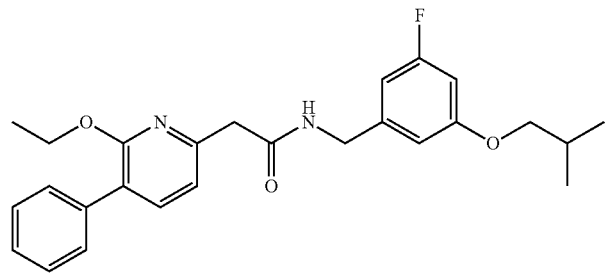 [SMILES: CCOc1nc(CC(=O)NCc2cc(F)cc(OCC(C)C)c2)ccc1-c1ccccc1] |
| 44 | 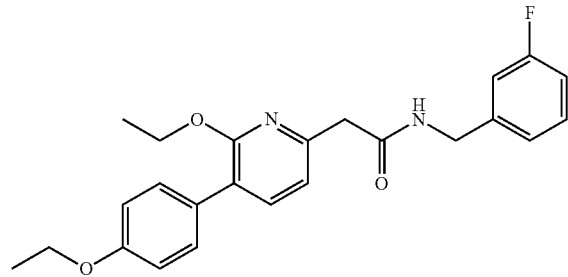 [SMILES: CCOc1ccc(-c2ccc(CC(=O)NCc3cccc(F)c3)nc2OCC)cc1] |

TABLE 1-continued
| Compound | Structure |
|---|---|
| 45 | 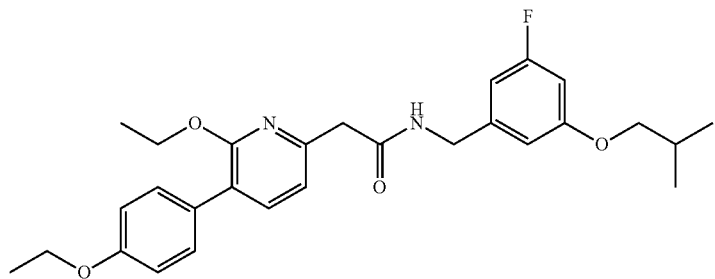 [SMILES: CCOc1ccc(-c2ccc(CC(=O)NCc3cc(F)cc(OCC(C)C)c3)nc2OCC)cc1] |
| 46 | 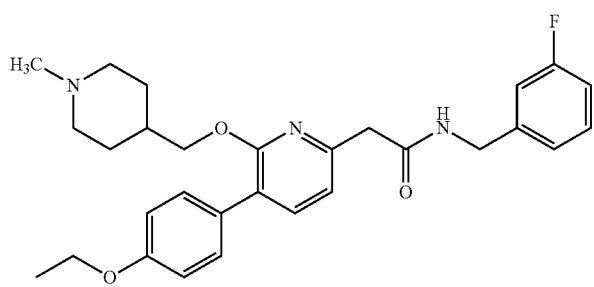 [SMILES: CCOc1ccc(-c2ccc(CC(=O)NCc3cccc(F)c3)nc2OCC2CCN(C)CC2)cc1] |
| 47 | 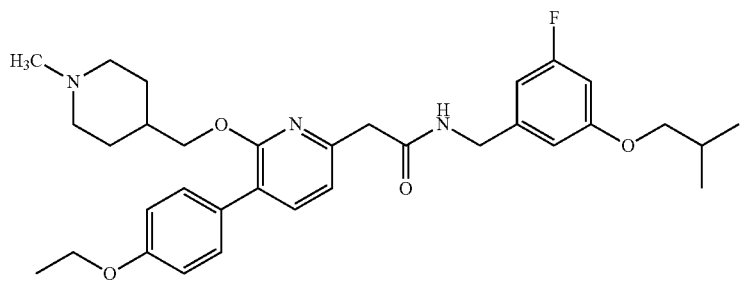 [SMILES: CCOc1ccc(-c2ccc(CC(=O)NCc3cc(F)cc(OCC(C)C)c3)nc2OCC2CCN(C)CC2)cc1] |
| 48 | 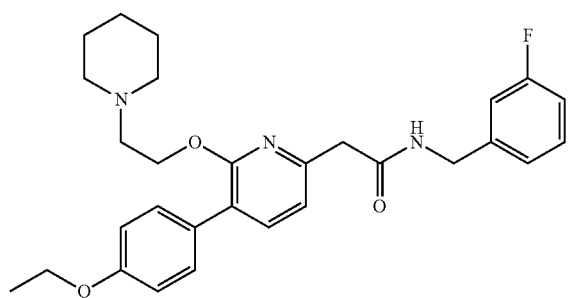 [SMILES: CCOc1ccc(-c2ccc(CC(=O)NCc3cccc(F)c3)nc2OCCN2CCCCC2)cc1] |
| 49 | 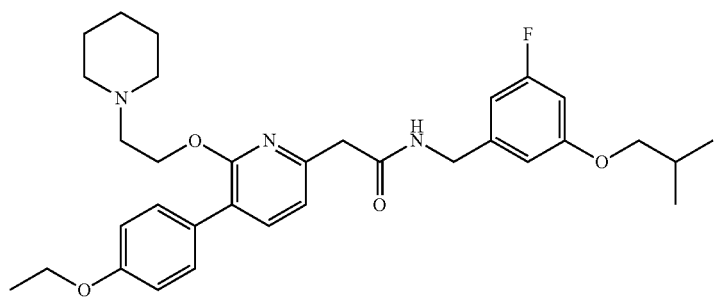 [SMILES: CCOc1ccc(-c2ccc(CC(=O)NCc3cc(F)cc(OCC(C)C)c3)nc2OCCN2CCCCC2)cc1] |

TABLE 1-continued

| Compound | Structure |
|---|---|
| 50 | 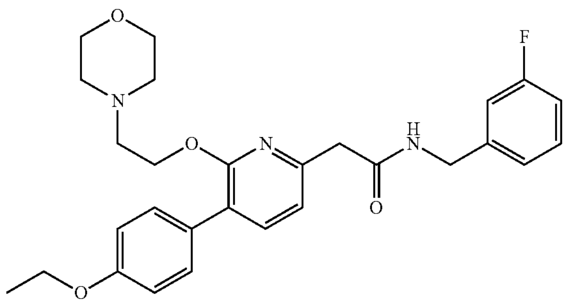 [SMILES: CCOc1ccc(-c2ccc(CC(=O)NCc3cccc(F)c3)nc2OCCN2CCOCC2)cc1] |
| 51 | 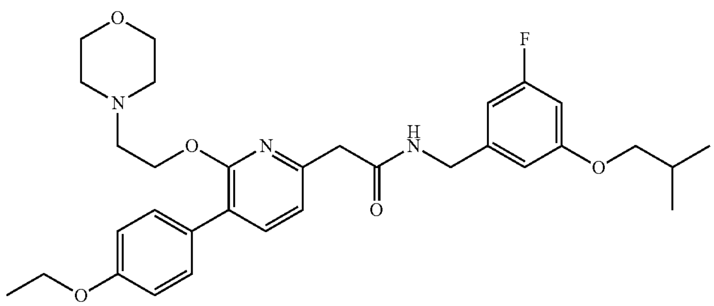 [SMILES: CCOc1ccc(-c2ccc(CC(=O)NCc3cc(F)cc(OCC(C)C)c3)nc2OCCN2CCOCC2)cc1] |
| 52 | 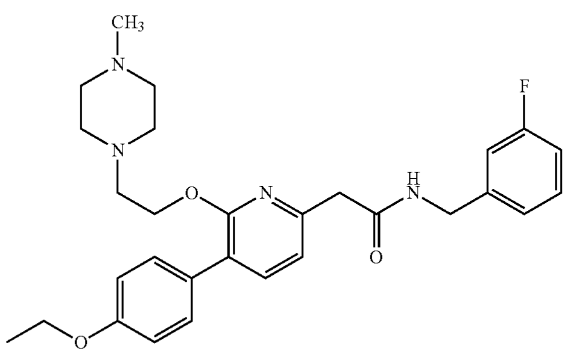 [SMILES: CCOc1ccc(-c2ccc(CC(=O)NCc3cccc(F)c3)nc2OCCN2CCN(C)CC2)cc1] |
| 53 | 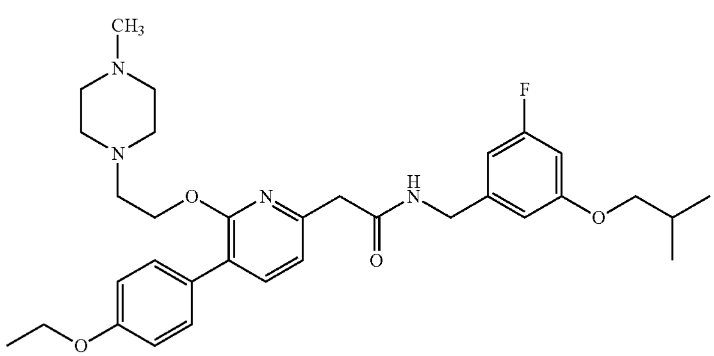 [SMILES: CCOc1ccc(-c2ccc(CC(=O)NCc3cc(F)cc(OCC(C)C)c3)nc2OCCN2CCN(C)CC2)cc1] |
| 54 | 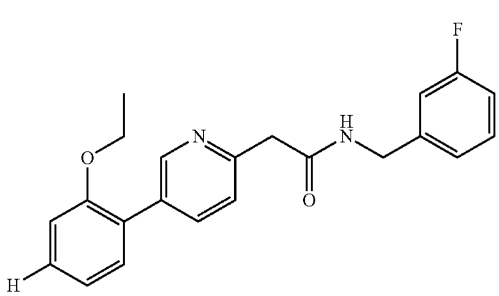 [SMILES: CCOc1ccccc1-c1ccc(CC(=O)NCc2cccc(F)c2)nc1] |

TABLE 1-continued
| Compound | Structure |
|---|---|
| 55 | 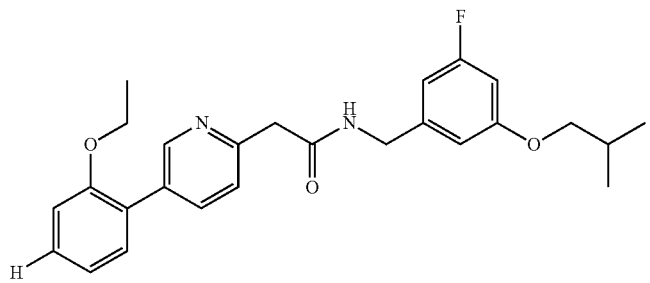 [SMILES: CCOc1ccccc1-c1ccc(CC(=O)NCc2cc(F)cc(OCC(C)C)c2)nc1] |
| 56 | 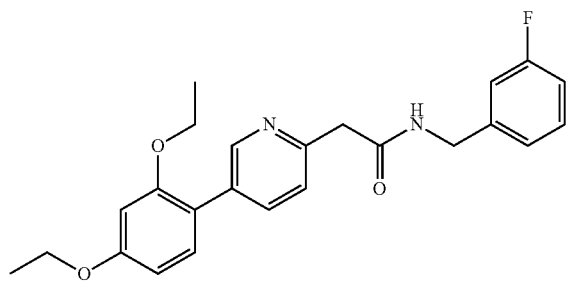 [SMILES: CCOc1ccc(-c2ccc(CC(=O)NCc3cccc(F)c3)nc2)c(OCC)c1] |
| 57 | 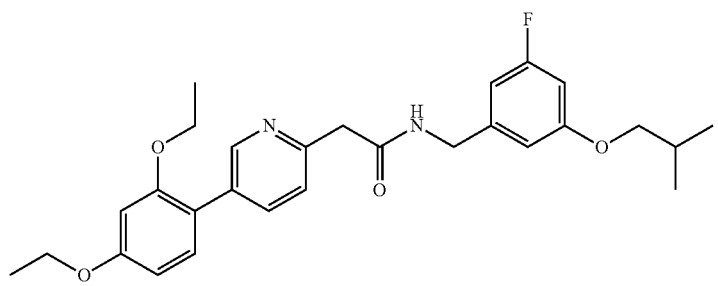 [SMILES: CCOc1ccc(-c2ccc(CC(=O)NCc3cc(F)cc(OCC(C)C)c3)nc2)c(OCC)c1] |
| 58 | 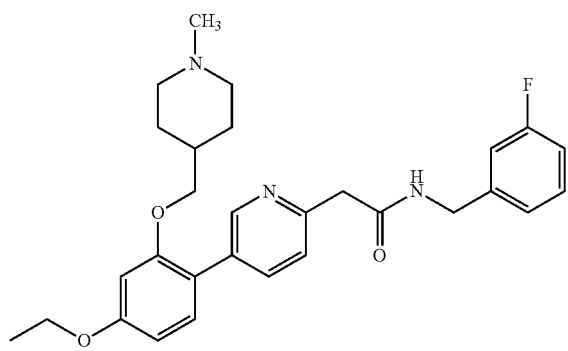 [SMILES: CCOc1ccc(-c2ccc(CC(=O)NCc3cccc(F)c3)nc2)c(OCC2CCN(C)CC2)c1] |
| 59 | 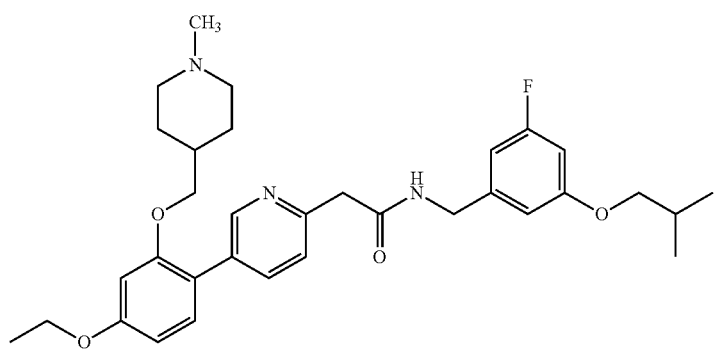 [SMILES: CCOc1ccc(-c2ccc(CC(=O)NCc3cc(F)cc(OCC(C)C)c3)nc2)c(OCC2CCN(C)CC2)c1] |

TABLE 1-continued

| Compound | Structure |
|---|---|
| 60 | 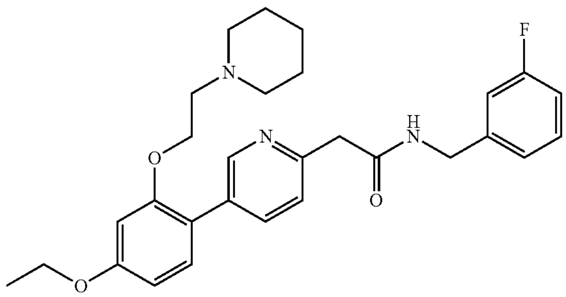 [SMILES: CCOc1ccc(-c2ccc(CC(=O)NCc3cccc(F)c3)nc2)c(OCCN2CCOCC2)c1] |
| 61 | 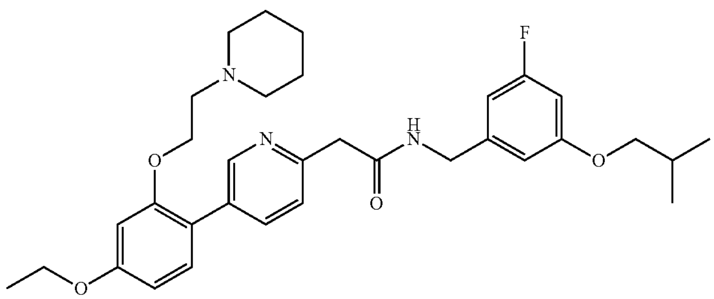 [SMILES: CCOc1ccc(-c2ccc(CC(=O)NCc3cc(F)cc(OCC(C)C)c3)nc2)c(OCCN2CCOCC2)c1] |
| 62 | 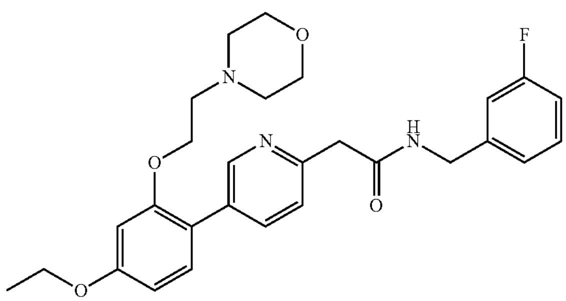 |
| 63 | 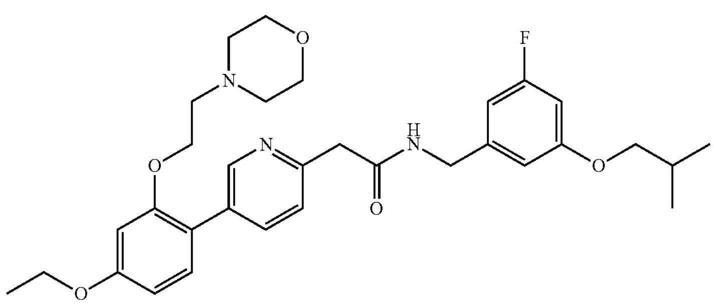 |
| 64 | 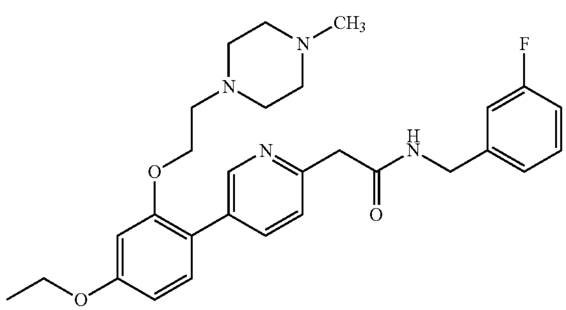 [SMILES: CCOc1ccc(-c2ccc(CC(=O)NCc3cccc(F)c3)nc2)c(OCCN2CCN(C)CC2)c1] |

TABLE 1-continued
| Compound | Structure |
|---|---|
| 65 | 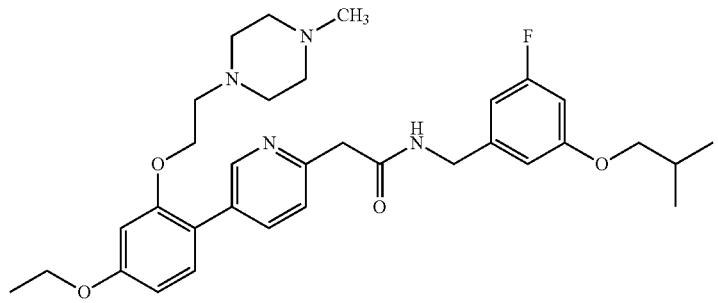 [SMILES: CCOc1ccc(-c2ccc(CC(=O)NCc3cc(F)cc(OCC(C)C)c3)nc2)c(OCCN2CCN(C)CC2)c1] |
| 66 | 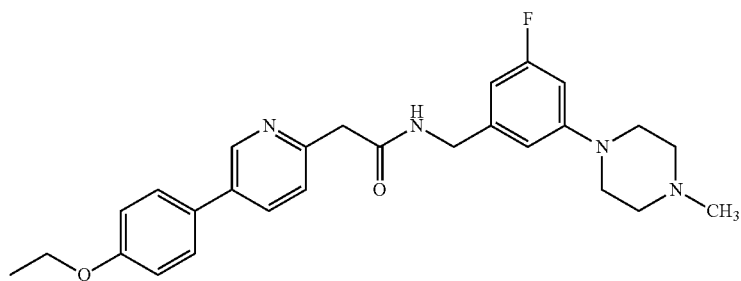 [SMILES: CCOc1ccc(-c2ccc(CC(=O)NCc3cc(F)cc(N4CCN(C)CC4)c3)nc2)cc1] |
| 67 | 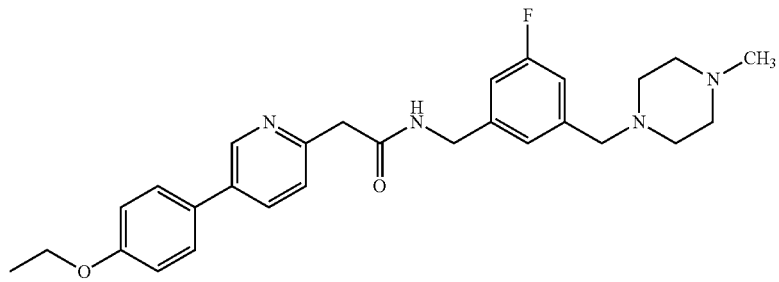 [SMILES: CCOc1ccc(-c2ccc(CC(=O)NCc3cc(F)cc(CN4CCN(C)CC4)c3)nc2)cc1] |
| 68 | 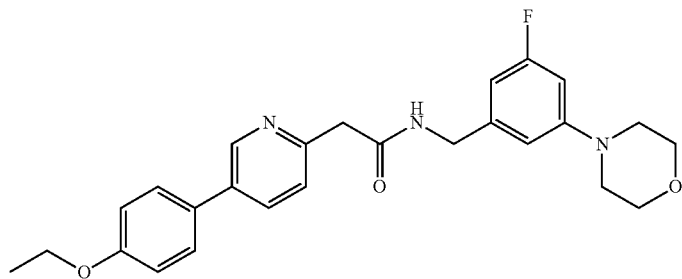 [SMILES: CCOc1ccc(-c2ccc(CC(=O)NCc3cc(F)cc(N4CCOCC4)c3)nc2)cc1] |
| 69 | 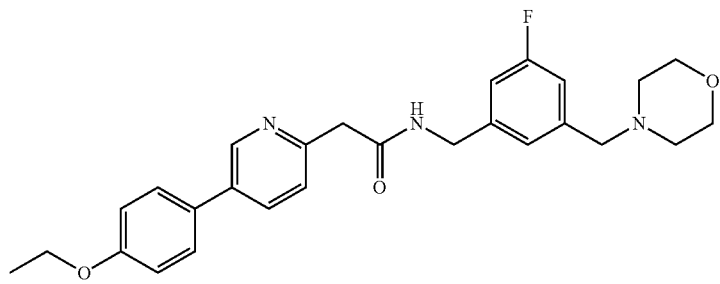 [SMILES: CCOc1ccc(-c2ccc(CC(=O)NCc3cc(F)cc(CN4CCOCC4)c3)nc2)cc1] |

TABLE 1-continued
| Compound | Structure |
|---|---|
| 70 | 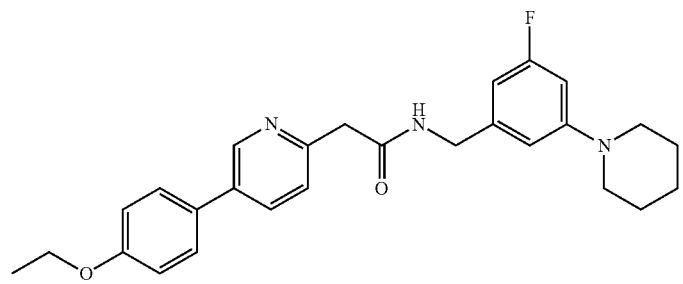 [SMILES: CCOc1ccc(-c2ccc(CC(=O)NCc3cc(F)cc(N4CCCCC4)c3)nc2)cc1] |
| 71 | 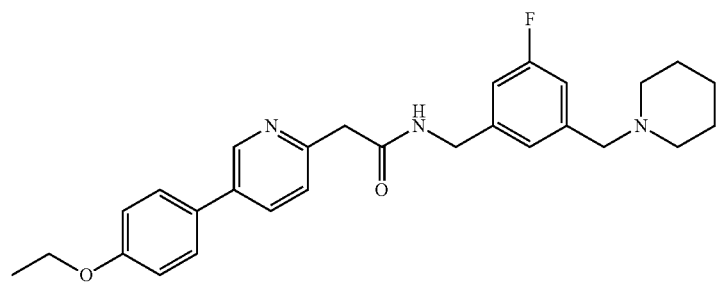 [SMILES: CCOc1ccc(-c2ccc(CC(=O)NCc3cc(F)cc(CN4CCCCC4)c3)nc2)cc1] |
| 72 | 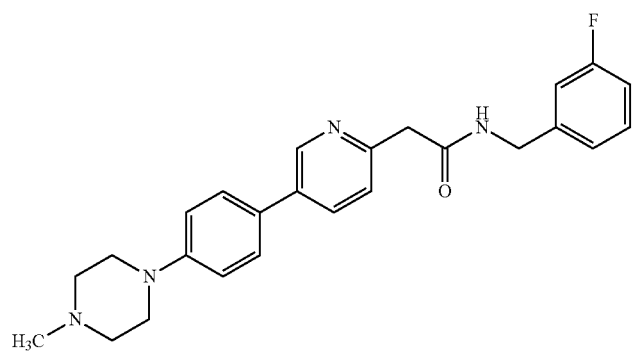 [SMILES: CN1CCN(c2ccc(-c3ccc(CC(=O)NCc4cccc(F)c4)nc3)cc2)CC1] |
| 73 | 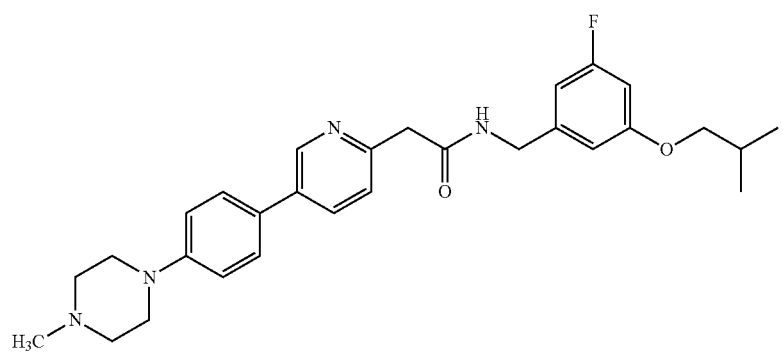 [SMILES: CC(C)COc1cc(F)cc(CNC(=O)Cc2ccc(-c3ccc(N4CCN(C)CC4)cc3)cn2)c1] |
| 74 | 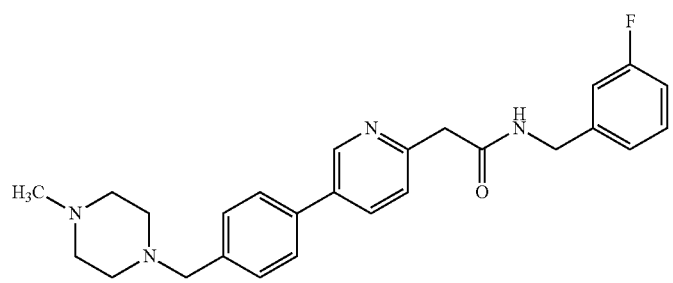 [SMILES: CN1CCN(Cc2ccc(-c3ccc(CC(=O)NCc4cccc(F)c4)nc3)cc2)CC1] |

TABLE 1-continued
| Compound | Structure |
|---|---|
| 75 | 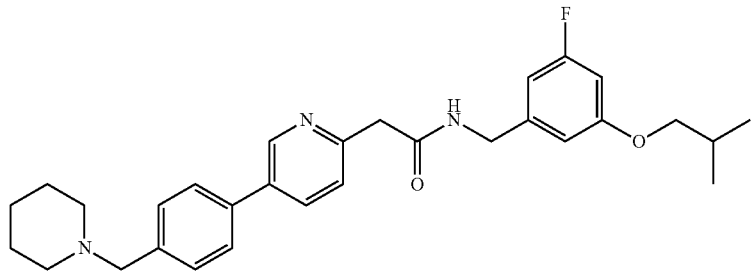 [SMILES: CC(C)COc1cc(F)cc(CNC(=O)Cc2ccc(-c3ccc(CN4CCCCC4)cc3)cn2)c1] |
| 76 | 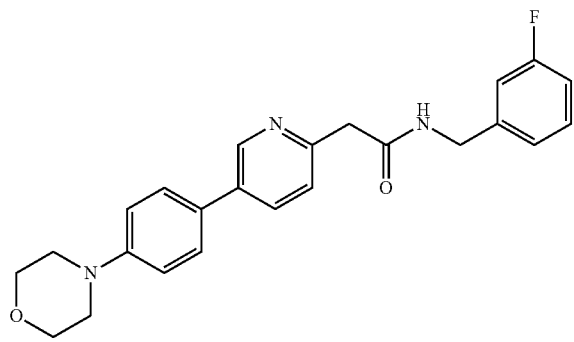 [SMILES: O=C(Cc1ccc(-c2ccc(N3CCOCC3)cc2)cn1)NCc1cccc(F)c1] |
| 77 | 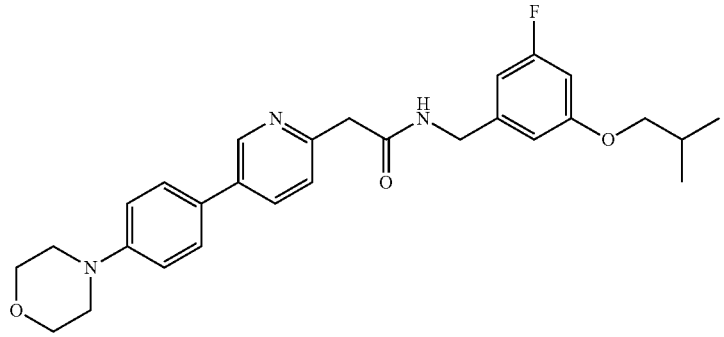 [SMILES: CC(C)COc1cc(F)cc(CNC(=O)Cc2ccc(-c3ccc(N4CCOCC4)cc3)cn2)c1] |
| 78 | 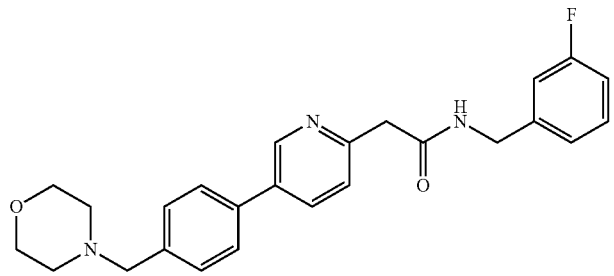 [SMILES: O=C(Cc1ccc(-c2ccc(CN3CCOCC3)cc2)cn1)NCc1cccc(F)c1] |
| 79 | 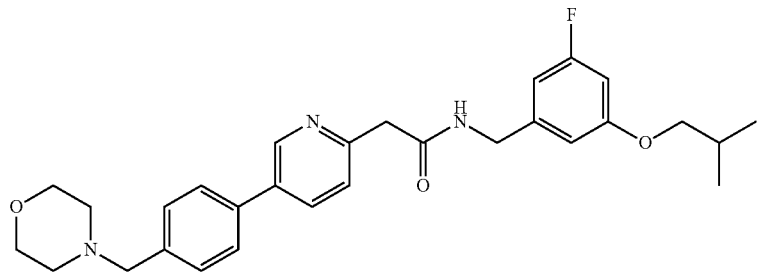 [SMILES: CC(C)COc1cc(F)cc(CNC(=O)Cc2ccc(-c3ccc(CN4CCOCC4)cc3)cn2)c1] |

TABLE 1-continued
| Compound | Structure |
|---|---|
| 80 | 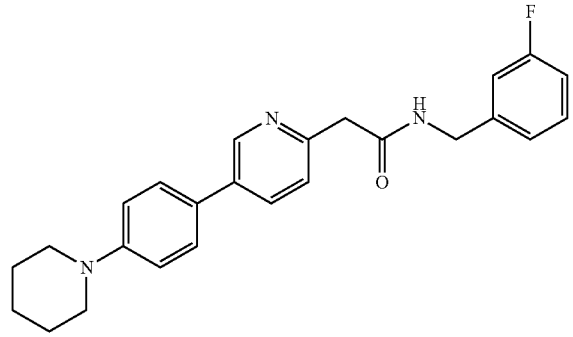 [SMILES: O=C(Cc1ccc(-c2ccc(N3CCCCC3)cc2)cn1)NCc1cccc(F)c1] |
| 81 | 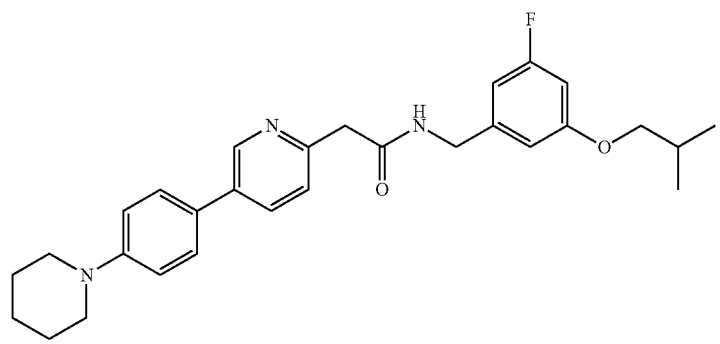 [SMILES: CC(C)COc1cc(F)cc(CNC(=O)Cc2ccc(-c3ccc(N4CCCCC4)cc3)cn2)c1] |
| 82 | 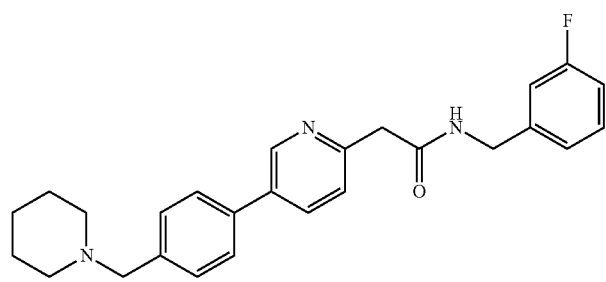 [SMILES: O=C(Cc1ccc(-c2ccc(CN3CCCCC3)cc2)cn1)NCc1cccc(F)c1] |
| 83 | 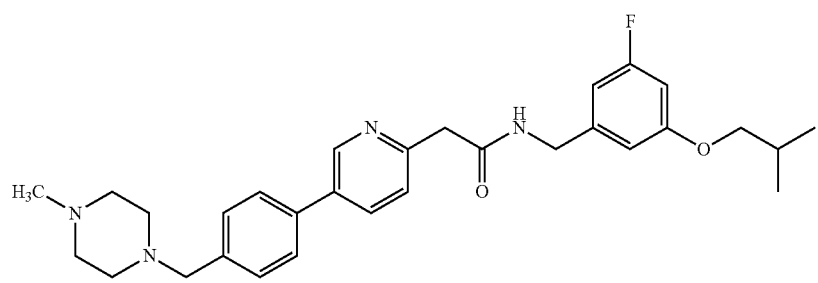 [SMILES: CC(C)COc1cc(F)cc(CNC(=O)Cc2ccc(-c3ccc(CN4CCN(C)CC4)cc3)cn2)c1] |
| 84 | 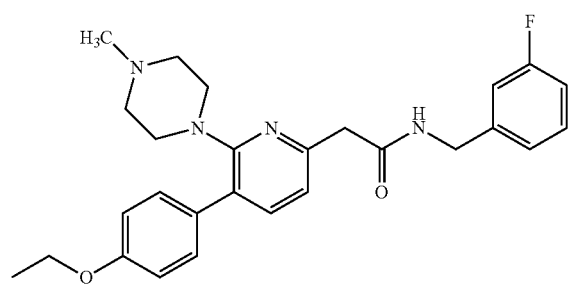 |

TABLE 1-continued
| Compound | Structure |
|---|---|
| 85 | 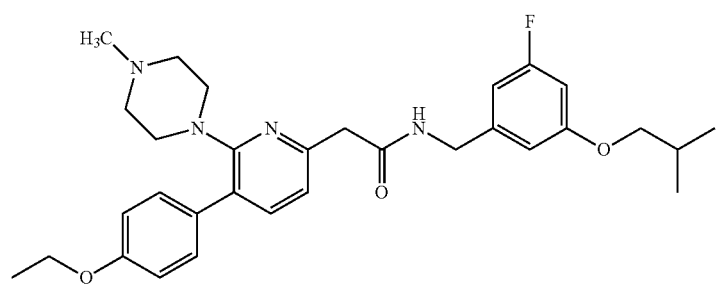 [SMILES: CCOc1ccc(-c2ccc(CC(=O)NCc3cc(F)cc(OCC(C)C)c3)nc2N2CCN(C)CC2)cc1] |
| 86 | 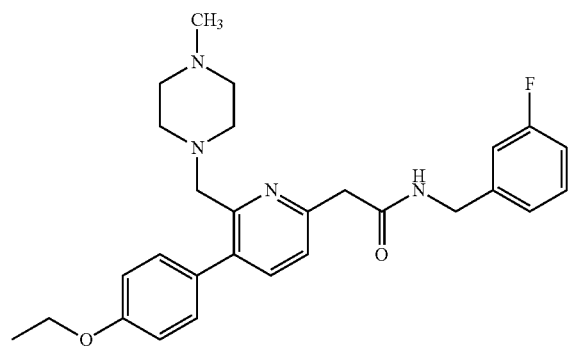 [SMILES: CCOc1ccc(-c2ccc(CC(=O)NCc3cccc(F)c3)nc2CN2CCN(C)CC2)cc1] |
| 87 | 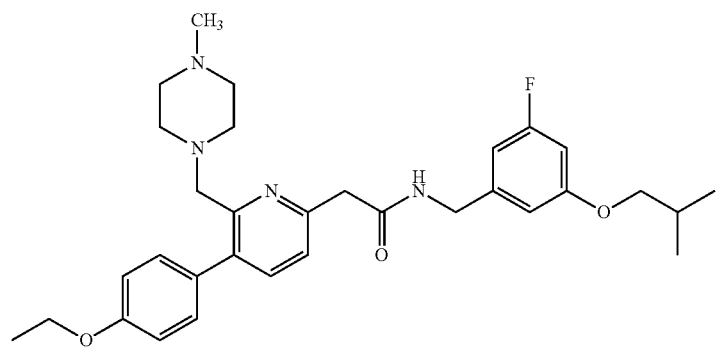 [SMILES: CCOc1ccc(-c2ccc(CC(=O)NCc3cc(F)cc(OCC(C)C)c3)nc2CN2CCN(C)CC2)cc1] |
| 88 | 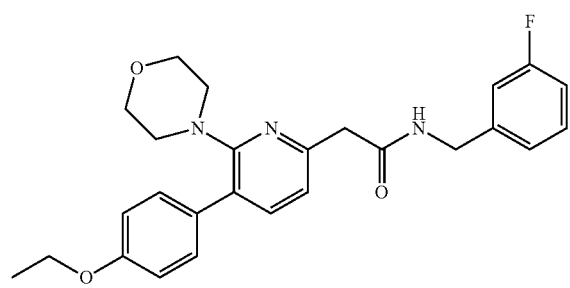 [SMILES: CCOc1ccc(-c2ccc(CC(=O)NCc3cccc(F)c3)nc2N2CCOCC2)cc1] |
| 89 | 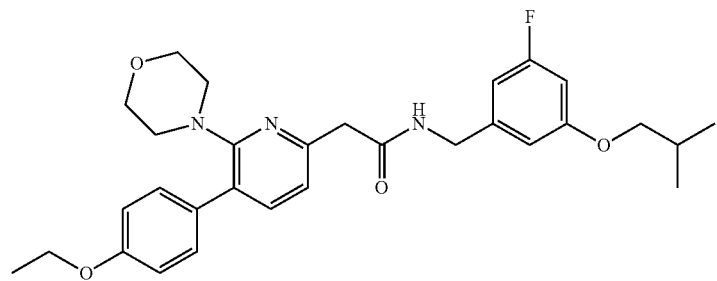 [SMILES: CCOc1ccc(-c2ccc(CC(=O)NCc3cc(F)cc(OCC(C)C)c3)nc2N2CCOCC2)cc1] |

TABLE 1-continued
| Compound | Structure |
|---|---|
| 90 | 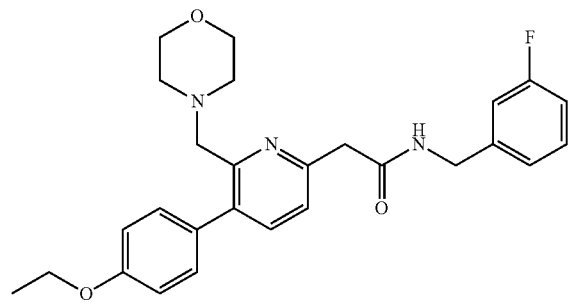 [SMILES: CCOc1ccc(-c2ccc(CC(=O)NCc3cccc(F)c3)nc2CN2CCOCC2)cc1] |
| 91 | 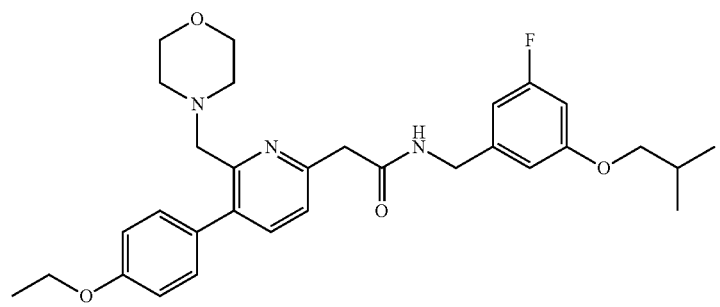 [SMILES: CCOc1ccc(-c2ccc(CC(=O)NCc3cc(F)cc(OCC(C)C)c3)nc2CN2CCOCC2)cc1] |
| 92 | 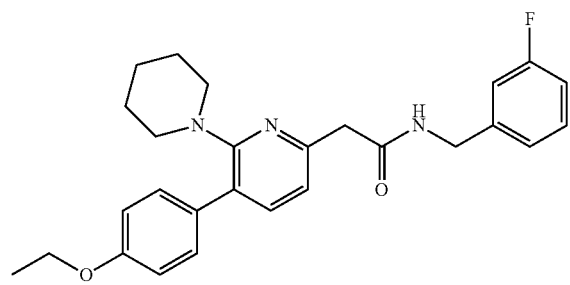 [SMILES: CCOc1ccc(-c2ccc(CC(=O)NCc3cccc(F)c3)nc2N2CCCCC2)cc1] |
| 93 | 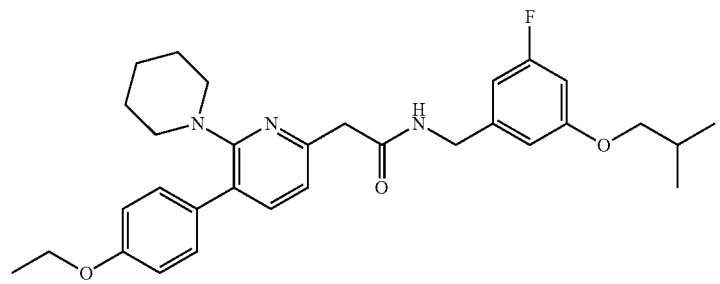 |
| 94 | 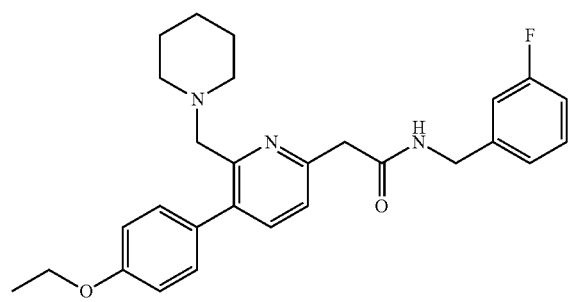 [SMILES: CCOc1ccc(-c2ccc(CC(=O)NCc3cccc(F)c3)nc2CN2CCCCC2)cc1] |

TABLE 1-continued
| Compound | Structure |
|---|---|
| 95 | 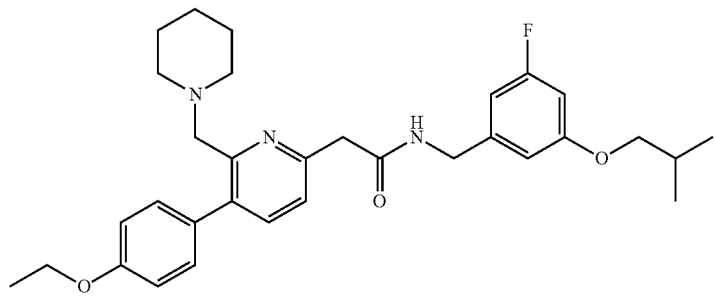 [SMILES: CCOc1ccc(-c2ccc(CC(=O)NCc3cc(F)cc(OCC(C)C)c3)nc2CN2CCCCC2)cc1] |
| 96 | 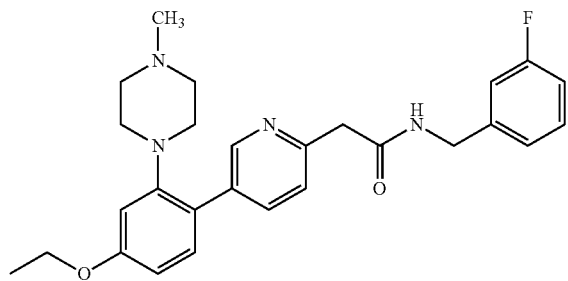 [SMILES: CCOc1ccc(-c2ccc(CC(=O)NCc3cccc(F)c3)nc2)c(N2CCN(C)CC2)c1] |
| 97 | 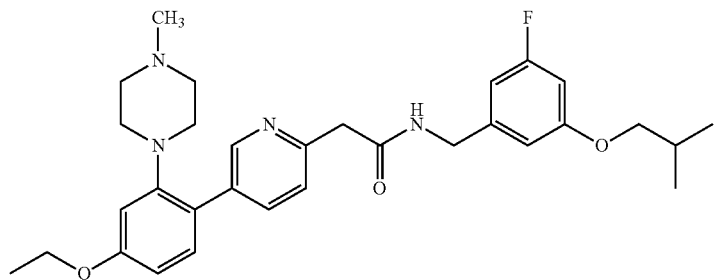 [SMILES: CCOc1ccc(-c2ccc(CC(=O)NCc3cc(F)cc(OCC(C)C)c3)nc2)c(N2CCN(C)CC2)c1] |
| 98 | 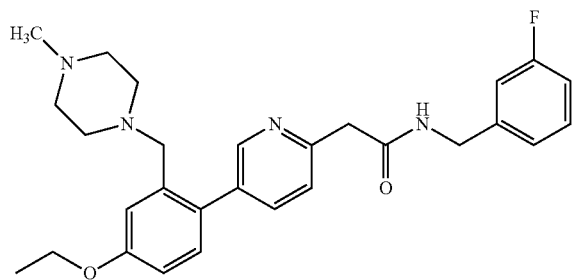 [SMILES: CCOc1ccc(-c2ccc(CC(=O)NCc3cccc(F)c3)nc2)c(CN2CCN(C)CC2)c1] |
| 99 | 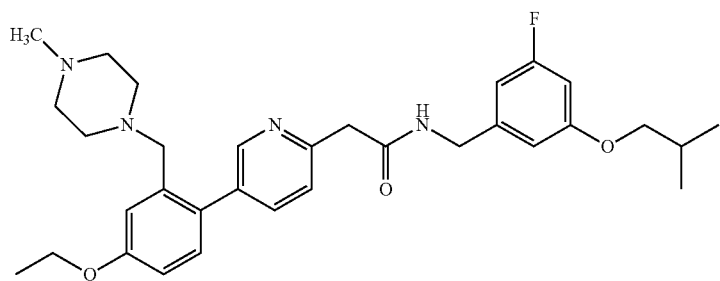 [SMILES: CCOc1ccc(-c2ccc(CC(=O)NCc3cc(F)cc(OCC(C)C)c3)nc2)c(CN2CCN(C)CC2)c1] |

TABLE 1-continued
| Compound | Structure |
|---|---|
| 100 | 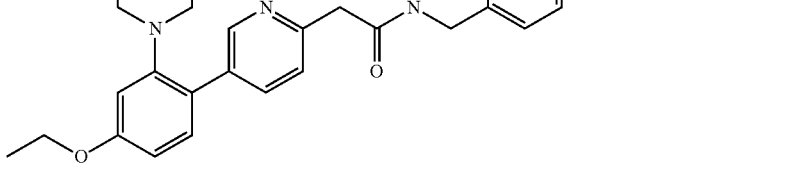 |
| 101 | 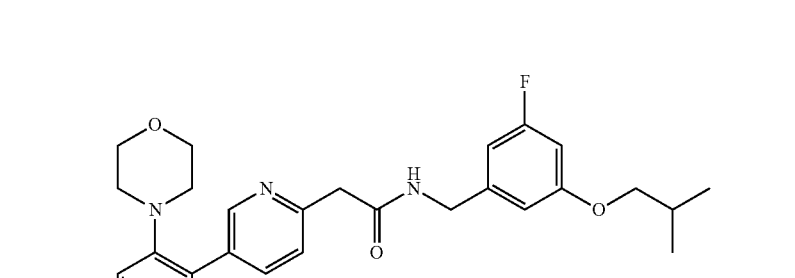 |
| 102 | 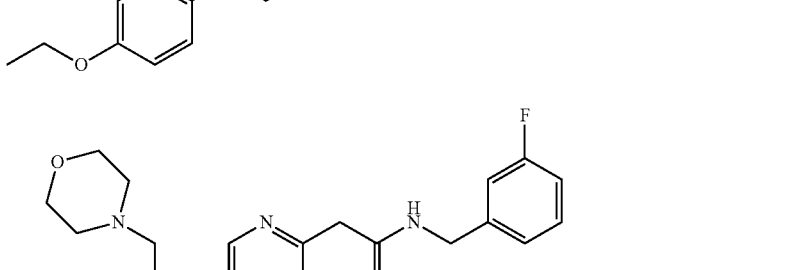 |
| 103 | 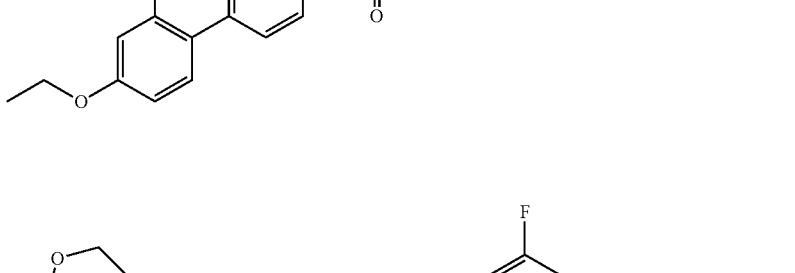 |
| 104 | 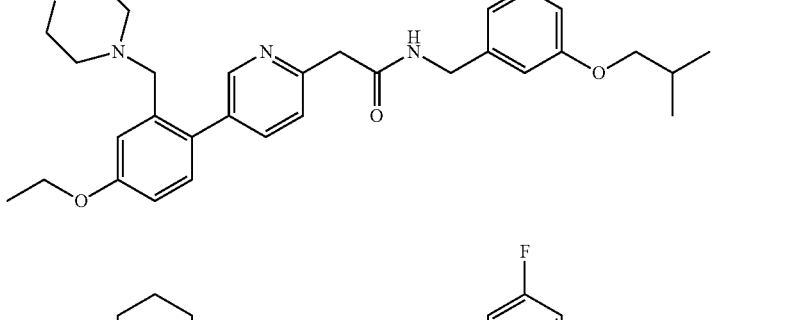 |

TABLE 1-continued
| Compound | Structure |
|---|---|
| 105 | 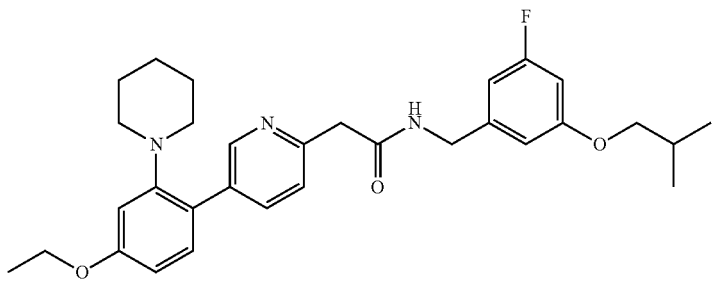 |
| 106 | 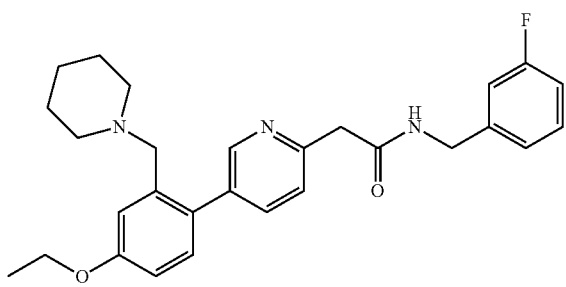 [SMILES: CCOc1ccc(-c2ccc(CC(=O)NCc3cccc(F)c3)nc2)c(CN2CCOCC2)c1] |
| 107 | 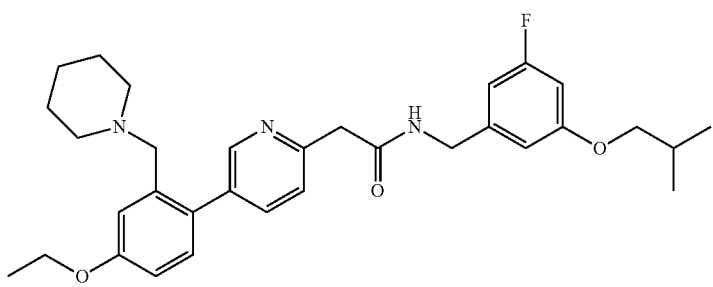 [SMILES: CCOc1ccc(-c2ccc(CC(=O)NCc3cc(F)cc(OCC(C)C)c3)nc2)c(CN2CCCCC2)c1] |
| 108A | 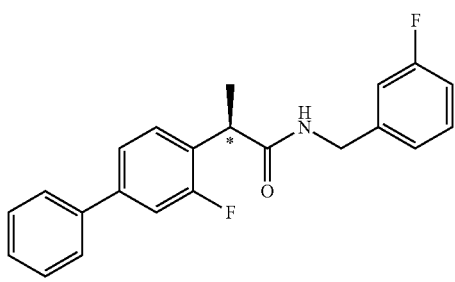 [SMILES: C[C@@H](C(=O)NCc1cccc(F)c1)c1ccc(-c2ccccc2)cc1F] |
| 108B | 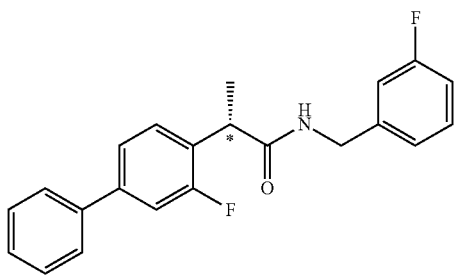 [SMILES: C[C@H](C(=O)NCc1cccc(F)c1)c1ccc(-c2ccccc2)cc1F] |

TABLE 1-continued
| Compound | Structure |
|---|---|
| 109 | 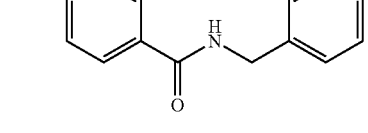 |
| 110 | 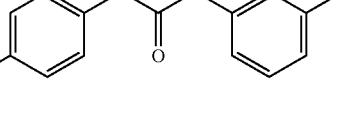 |
| 111 | 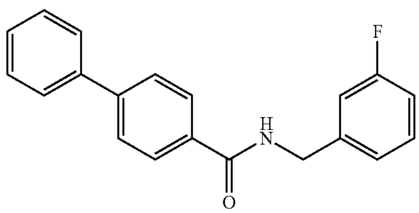 [SMILES: O=C(NCc1cccc(F)c1)c1ccc(-c2ccccc2)cc1] |
| 112 | 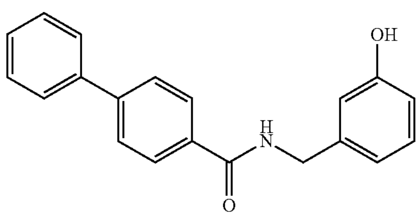 [SMILES: O=C(NCc1cccc(O)c1)c1ccc(-c2ccccc2)cc1] |
| 113 | 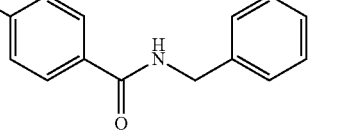 |
| 114 | 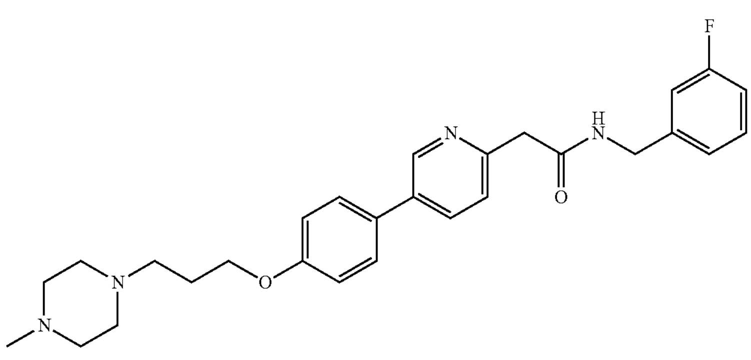 [SMILES: CN1CCN(CCCOc2ccc(-c3ccc(CC(=O)NCc4cccc(F)c4)nc3)cc2)CC1] |

TABLE 1-continued

| Compound | Structure |
|---|---|
| 115 | 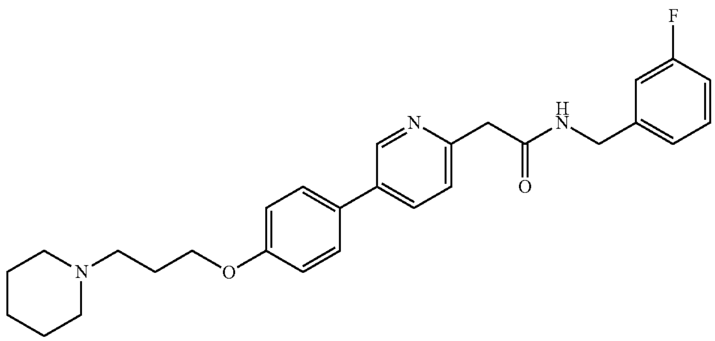 [SMILES: O=C(Cc1ccc(-c2ccc(OCCCN3CCCCC3)cc2)cn1)NCc1cccc(F)c1] |
| 116 | 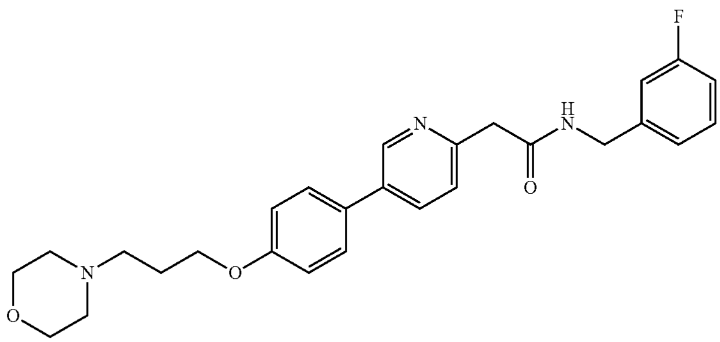 [SMILES: O=C(Cc1ccc(-c2ccc(OCCCN3CCOCC3)cc2)cn1)NCc1cccc(F)c1] |
| 117 | 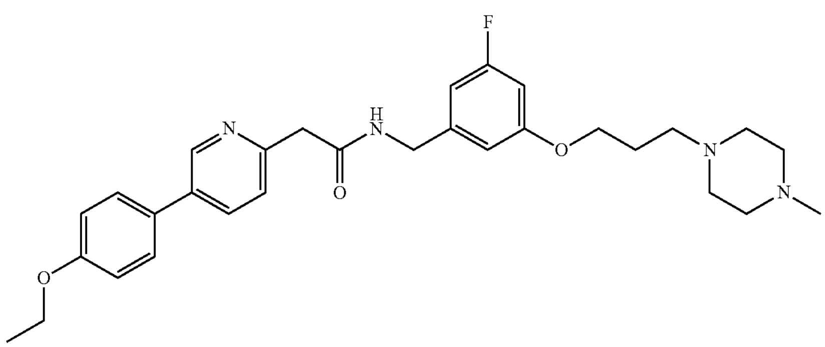 [SMILES: CCOc1ccc(-c2ccc(CC(=O)NCc3cc(F)cc(OCCCN4CCN(C)CC4)c3)nc2)cc1] |
| 118 | 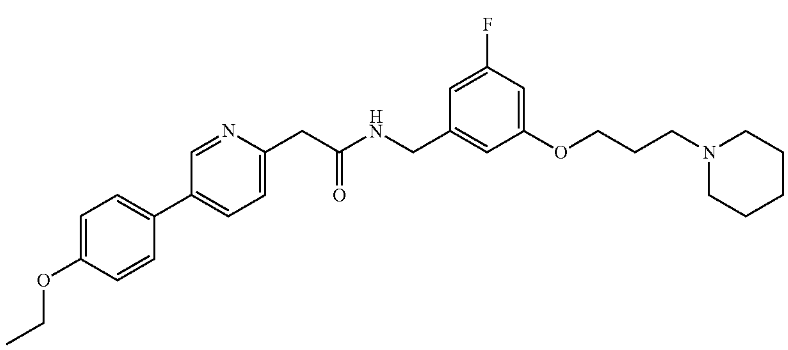 [SMILES: CCOc1ccc(-c2ccc(CC(=O)NCc3cc(F)cc(OCCCN4CCCCC4)c3)nc2)cc1] |

TABLE 1-continued
| Compound | Structure |
|---|---|
| 119 | 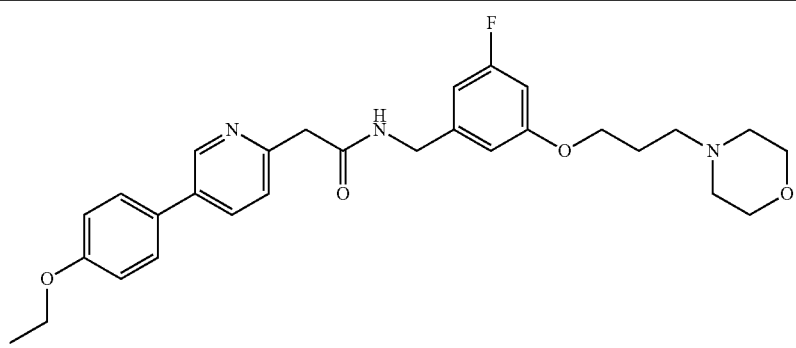 |
| 120 | 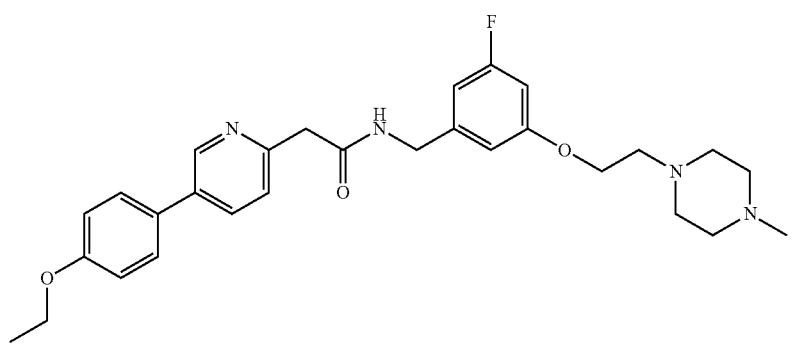 [SMILES: CCOc1ccc(-c2ccc(CC(=O)NCc3cc(F)cc(OCCN4CCN(C)CC4)c3)nc2)cc1] |
| 121 | 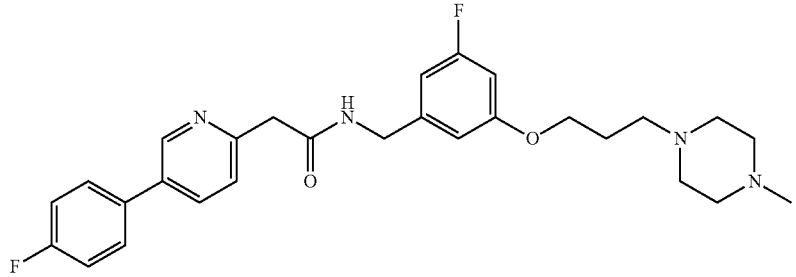 [SMILES: CN1CCN(CCCOc2cc(F)cc(CNC(=O)Cc3ccc(-c4ccc(F)cc4)cn3)c2)CC1] |
| 122 | 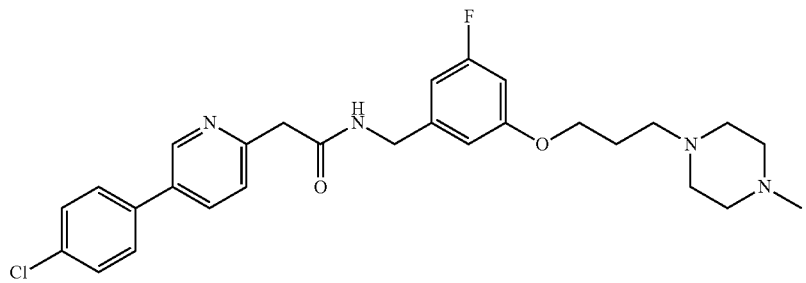 [SMILES: CN1CCN(CCCOc2cc(F)cc(CNC(=O)Cc3ccc(-c4ccc(Cl)cc4)cn3)c2)CC1] |
| 123 | 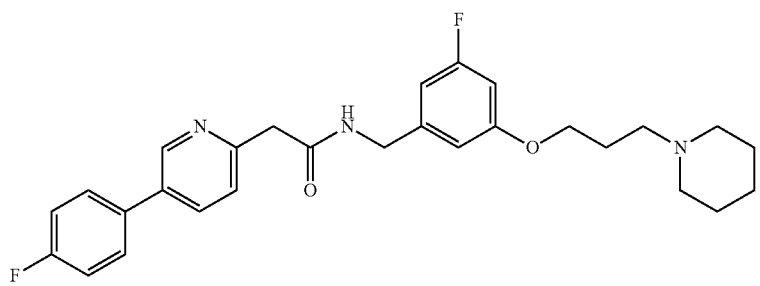 [SMILES: O=C(Cc1ccc(-c2ccc(F)cc2)cn1)NCc1cc(F)cc(OCCCN2CCCCC2)c1] |

TABLE 1-continued
| Compound | Structure |
|---|---|
| 124 | 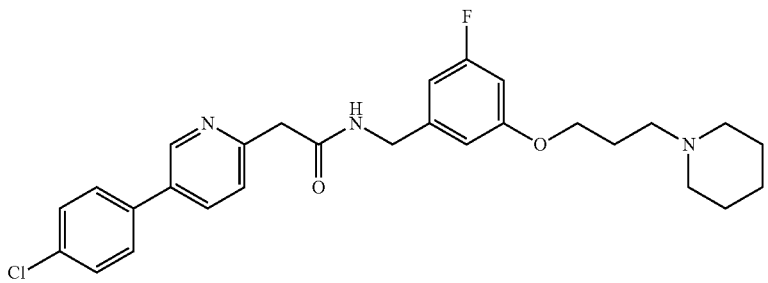 [SMILES: O=C(Cc1ccc(-c2ccc(Cl)cc2)cn1)NCc1cc(F)cc(OCCCN2CCCCC2)c1] |
| 125 | 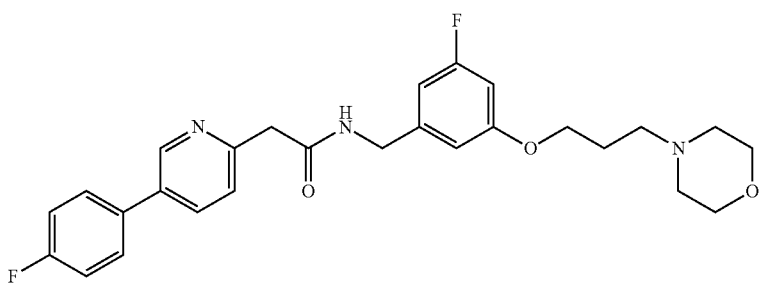 [SMILES: O=C(Cc1ccc(-c2ccc(F)cc2)cn1)NCc1cc(F)cc(OCCCN2CCOCC2)c1] |
| 126 | 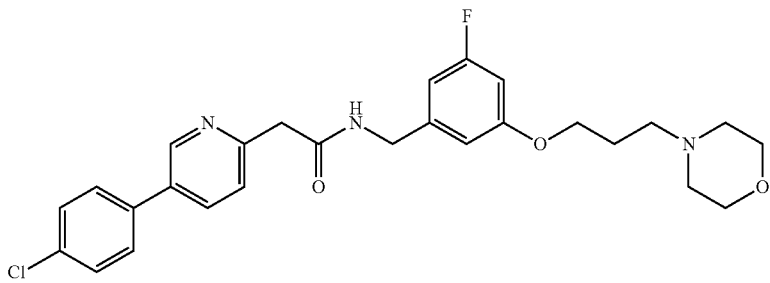 [SMILES: O=C(Cc1ccc(-c2ccc(Cl)cc2)cn1)NCc1cc(F)cc(OCCCN2CCOCC2)c1] |
| 127 | 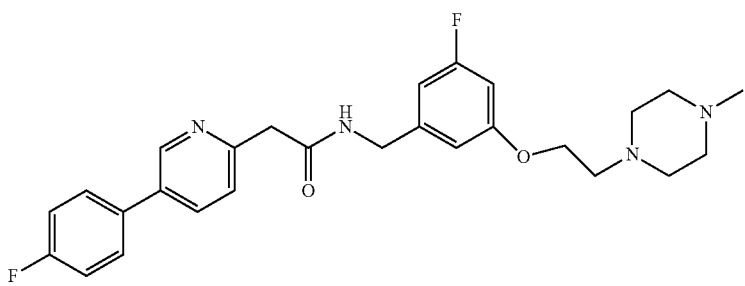 [SMILES: CN1CCN(CCOc2cc(F)cc(CNC(=O)Cc3ccc(-c4ccc(F)cc4)cn3)c2)CC1] |
| 128 | 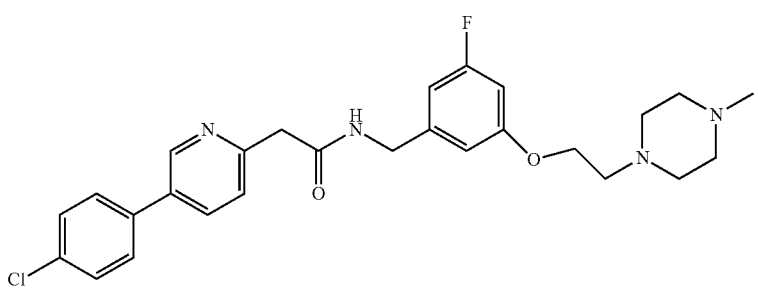 [SMILES: CN1CCN(CCOc2cc(F)cc(CNC(=O)Cc3ccc(-c4ccc(Cl)cc4)cn3)c2)CC1] |

| Compound | Structure |
|---|---|
| 129 | (5-(4-fluorophenyl)pyridin-2-yl)-CH2-C(=O)-NH-CH2-(3-fluoro-5-(2-(piperidin-1-yl)ethoxy)phenyl) |
| 130 | (5-(4-chlorophenyl)pyridin-2-yl)-CH2-C(=O)-NH-CH2-(3-fluoro-5-(2-(piperidin-1-yl)ethoxy)phenyl) |
| 131 | (5-(4-fluorophenyl)pyridin-2-yl)-CH2-C(=O)-NH-CH2-(3-fluoro-5-(2-morpholinoethoxy)phenyl) |
| 132 | (5-(4-chlorophenyl)pyridin-2-yl)-CH2-C(=O)-NH-CH2-(3-fluoro-5-(2-morpholinoethoxy)phenyl) |
| 133 | (5-(4-(2-morpholinoethoxy)-2-fluorophenyl)pyridin-2-yl)-CH2-C(=O)-NH-CH2-(3-fluorophenyl) |

TABLE 1-continued
| Compound | Structure |
|---|---|
| 134 | 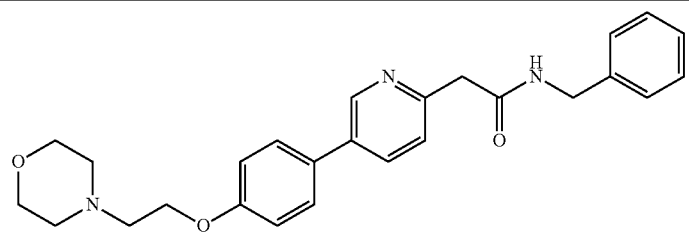 |
| 135 | 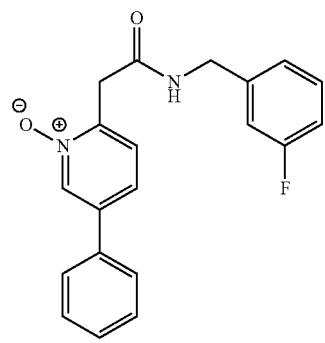 [SMILES: O=C(Cc1ccc(-c2ccccc2)c[n+]1[O-])NCc1cccc(F)c1] |
| 136 | 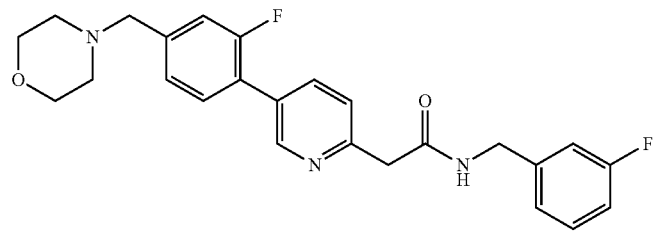 [SMILES: O=C(Cc1ccc(-c2ccc(CN3CCOCC3)cc2F)cn1)NCc1cccc(F)c1] |
| 137 | 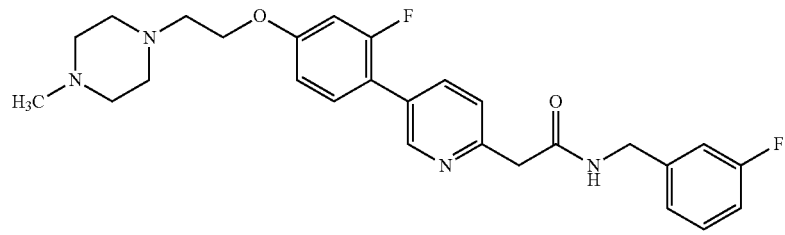 [SMILES: CN1CCN(CCOc2ccc(-c3ccc(CC(=O)NCc4cccc(F)c4)nc3)c(F)c2)CC1] |
Other Compounds are listed in Table 2.
TABLE 2
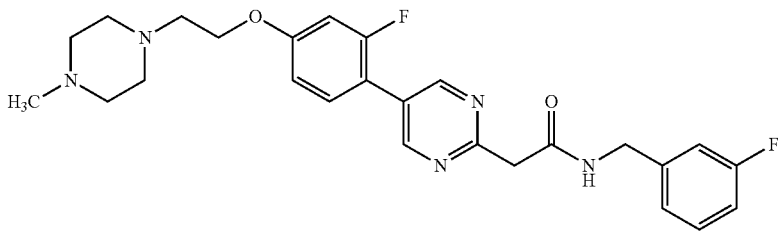 [SMILES: CN1CCN(CCOc2ccc(-c3cnc(CC(=O)NCc4cccc(F)c4)nc3)c(F)c2)CC1]
138

TABLE 2-continued
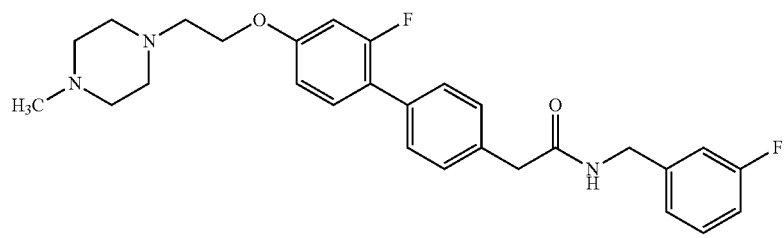 [SMILES: CN1CCN(CCOc2ccc(-c3ccc(CC(=O)NCc4cccc(F)c4)cc3)c(F)c2)CC1]
139
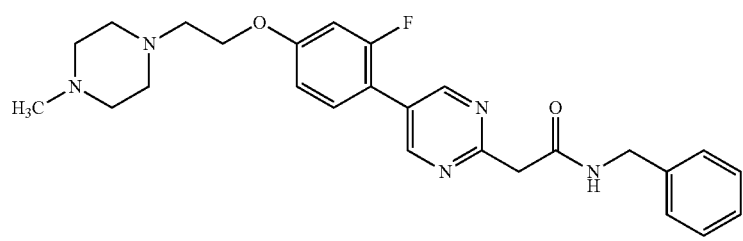 [SMILES: CN1CCN(CCOc2ccc(-c3cnc(CC(=O)NCc4ccccc4)nc3)c(F)c2)CC1]
140
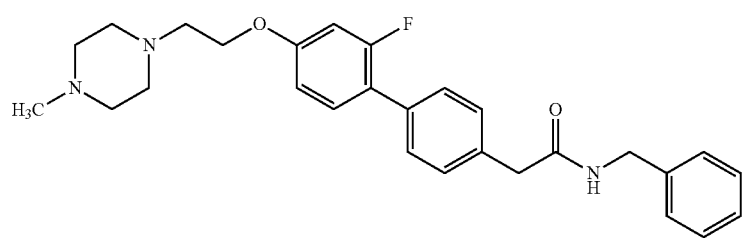 [SMILES: CN1CCN(CCOc2ccc(-c3ccc(CC(=O)NCc4ccccc4)cc3)c(F)c2)CC1]
141
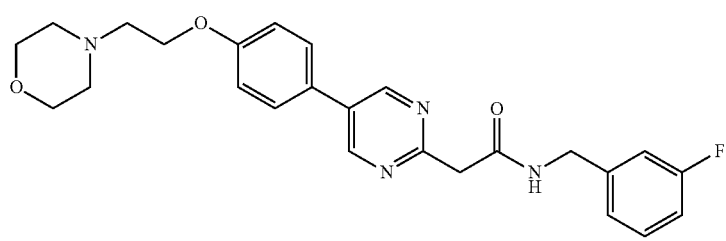 [SMILES: O=C(Cc1ncc(-c2ccc(OCCN3CCOCC3)cc2)cn1)NCc1cccc(F)c1]
142
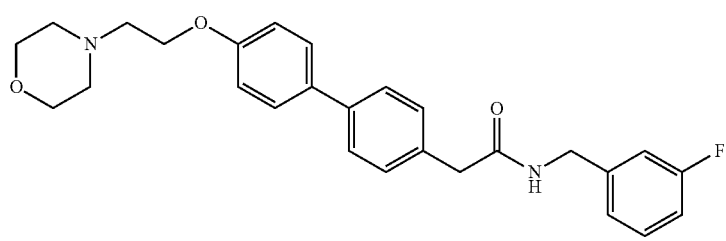 [SMILES: O=C(Cc1ccc(-c2ccc(OCCN3CCOCC3)cc2)cc1)NCc1cccc(F)c1]
143
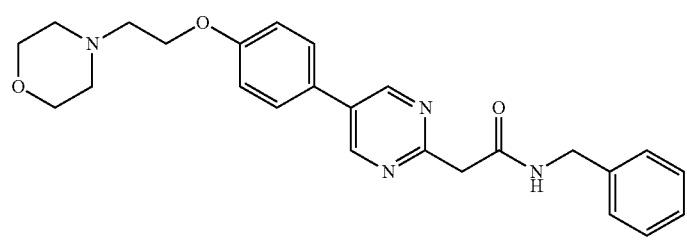 [SMILES: O=C(Cc1ncc(-c2ccc(OCCN3CCOCC3)cc2)cn1)NCc1ccccc1]
144

TABLE 2-continued
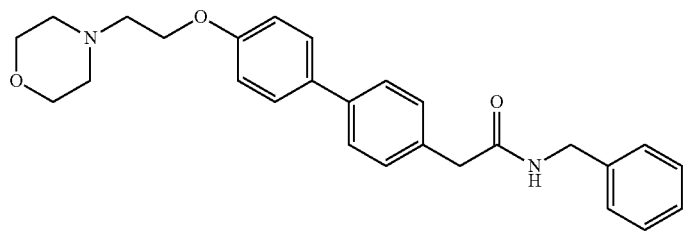 [SMILES: O=C(Cc1ccc(-c2ccc(OCCN3CCOCC3)cc2)cc1)NCc1ccccc1]
145
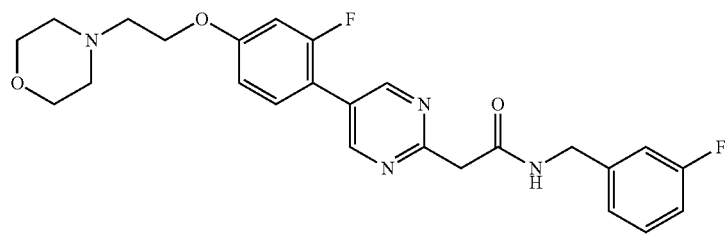 [SMILES: O=C(Cc1ncc(-c2ccc(OCCN3CCOCC3)cc2F)cn1)NCc1cccc(F)c1]
146
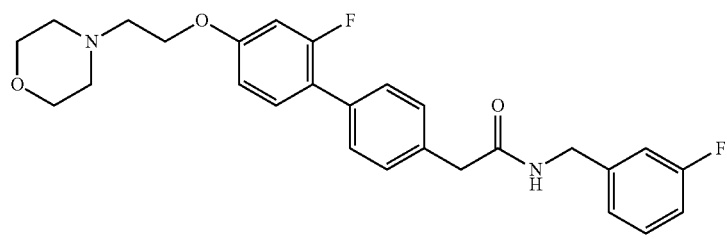 [SMILES: O=C(Cc1ccc(-c2ccc(OCCN3CCOCC3)cc2F)cc1)NCc1cccc(F)c1]
147
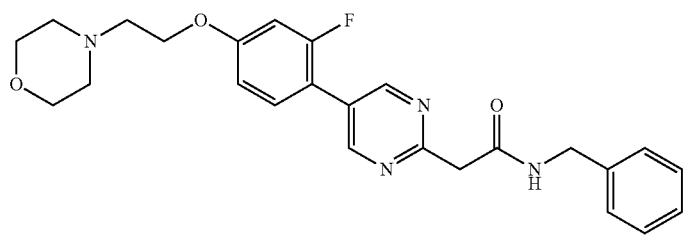 [SMILES: O=C(Cc1ncc(-c2ccc(OCCN3CCOCC3)cc2F)cn1)NCc1ccccc1]
148
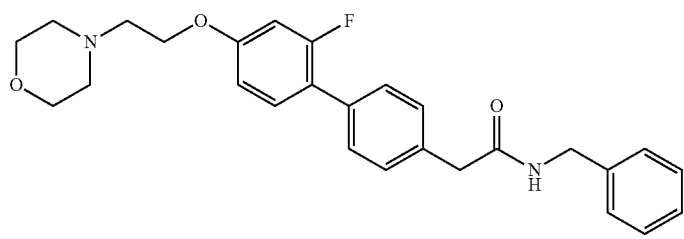 [SMILES: O=C(Cc1ccc(-c2ccc(OCCN3CCOCC3)cc2F)cc1)NCc1ccccc1]
149
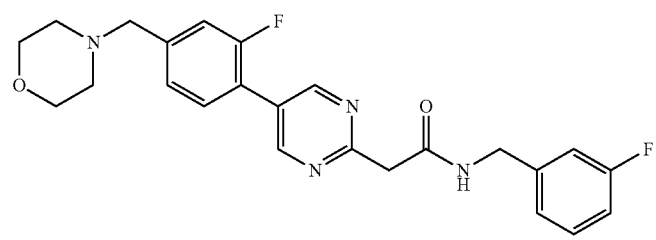
150

TABLE 2-continued
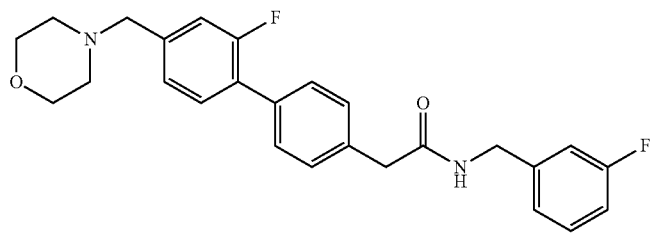 [SMILES: O=C(Cc1ccc(-c2ccc(CN3CCOCC3)cc2F)cc1)NCc1cccc(F)c1]
151
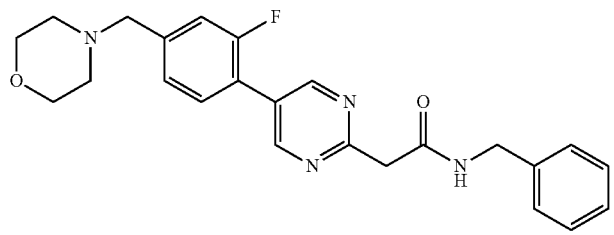 [SMILES: O=C(Cc1ncc(-c2ccc(CN3CCOCC3)cc2F)cn1)NCc1ccccc1]
152
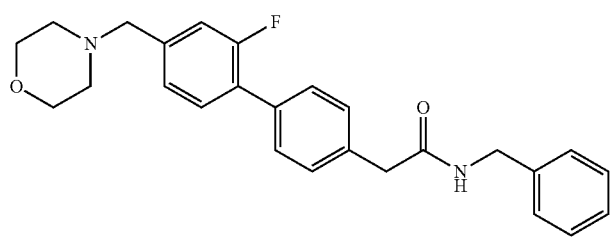 [SMILES: O=C(Cc1ccc(-c2ccc(CN3CCOCC3)cc2F)cc1)NCc1ccccc1]
153
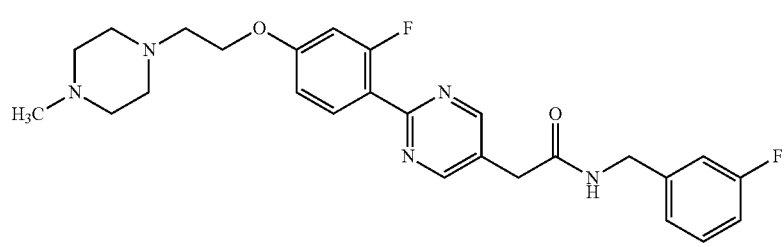 [SMILES: CN1CCN(CCOc2ccc(-c3ncc(CC(=O)NCc4cccc(F)c4)cn3)c(F)c2)CC1]
154
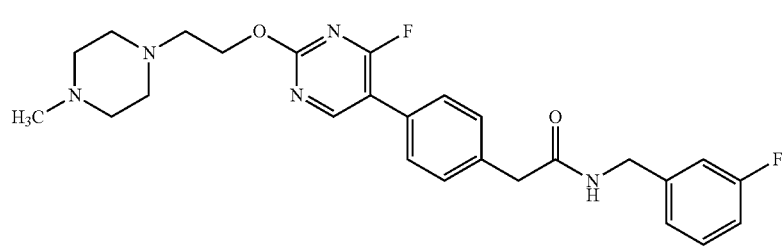 [SMILES: CN1CCN(CCOc2ncc(-c3ccc(CC(=O)NCc4cccc(F)c4)cc3)c(F)n2)CC1]
155
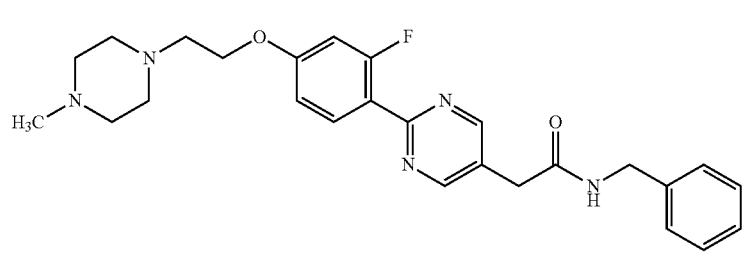 [SMILES: CN1CCN(CCOc2ccc(-c3ncc(CC(=O)NCc4ccccc4)cn3)c(F)c2)CC1]
156

TABLE 2-continued
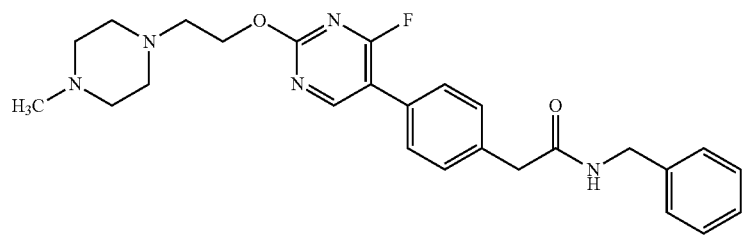 [SMILES: CN1CCN(CCOc2ncc(-c3ccc(CC(=O)NCc4ccccc4)cc3)c(F)n2)CC1]
157
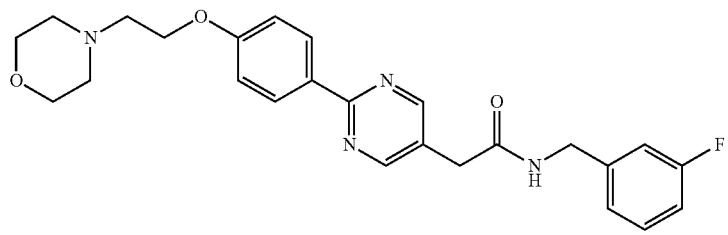
158
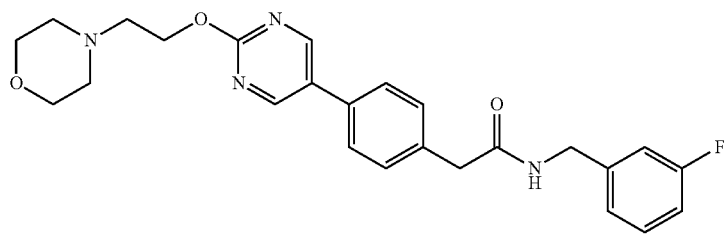
159
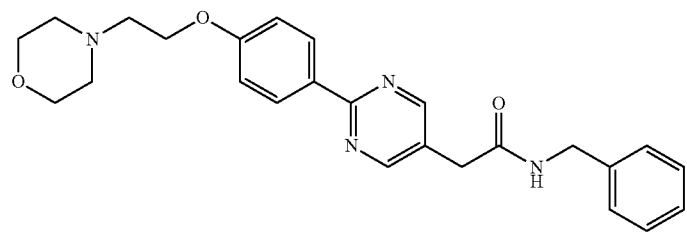 [SMILES: O=C(Cc1cnc(-c2ccc(OCCN3CCOCC3)cc2)nc1)NCc1ccccc1]
160
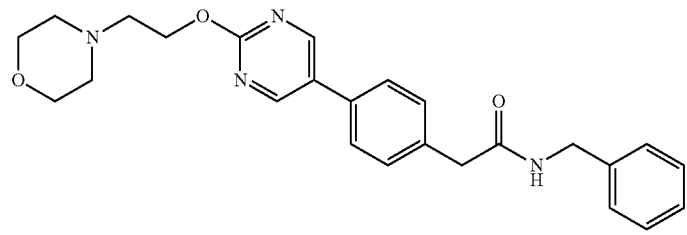
161
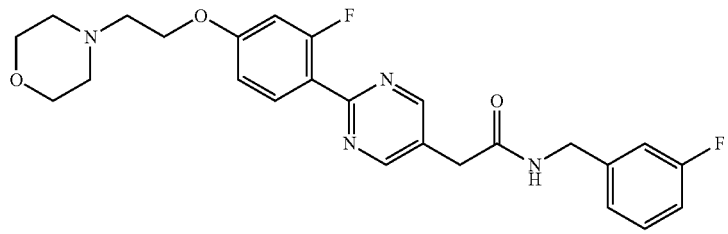
162

TABLE 2-continued
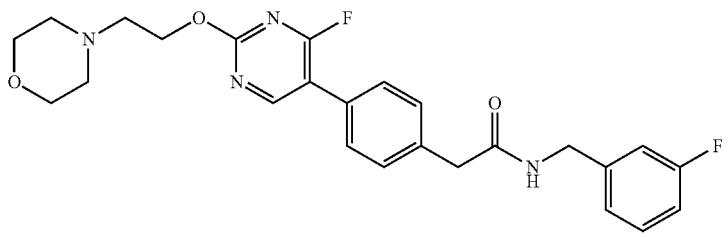 [SMILES: O=C(Cc1ccc(-c2cnc(OCCN3CCOCC3)nc2F)cc1)NCc1cccc(F)c1]
163
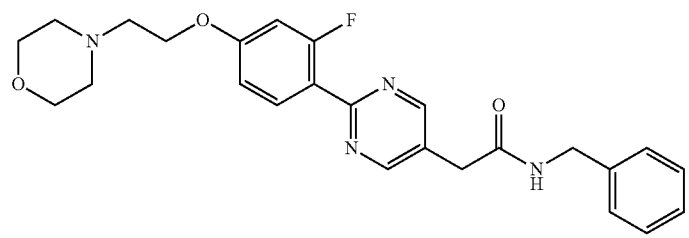 [SMILES: O=C(Cc1cnc(-c2ccc(OCCN3CCOCC3)cc2F)nc1)NCc1ccccc1]
164
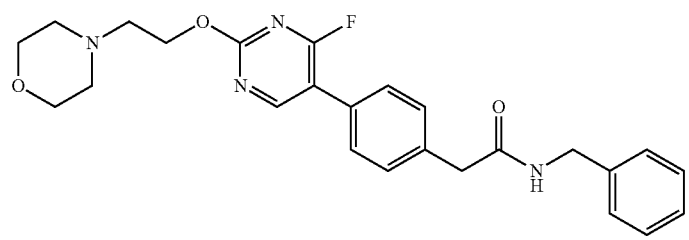 [SMILES: O=C(Cc1ccc(-c2cnc(OCCN3CCOCC3)nc2F)cc1)NCc1ccccc1]
165
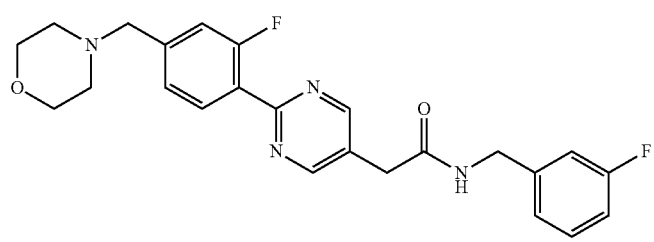 [SMILES: O=C(Cc1cnc(-c2ccc(CN3CCOCC3)cc2F)nc1)NCc1cccc(F)c1]
166
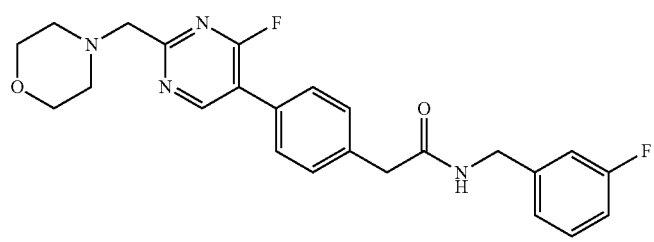 [SMILES: O=C(Cc1ccc(-c2cnc(CN3CCOCC3)nc2F)cc1)NCc1cccc(F)c1]
167
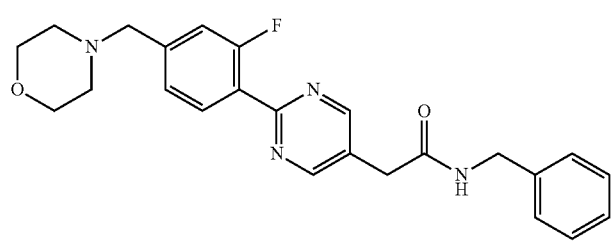 [SMILES: O=C(Cc1cnc(-c2ccc(CN3CCOCC3)cc2F)nc1)NCc1ccccc1]
168

TABLE 2-continued
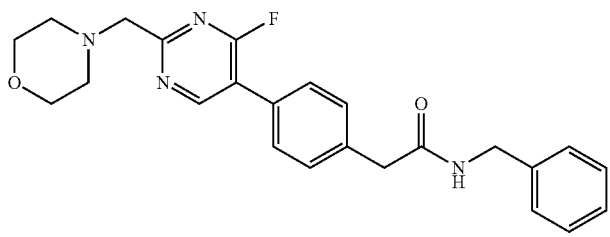 [SMILES: O=C(Cc1ccc(-c2cnc(CN3CCOCC3)nc2F)cc1)NCc1ccccc1]
169
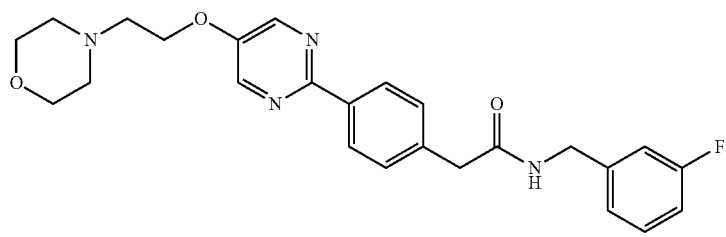 [SMILES: O=C(Cc1ccc(-c2ncc(OCCN3CCOCC3)cn2)cc1)NCc1cccc(F)c1]
170
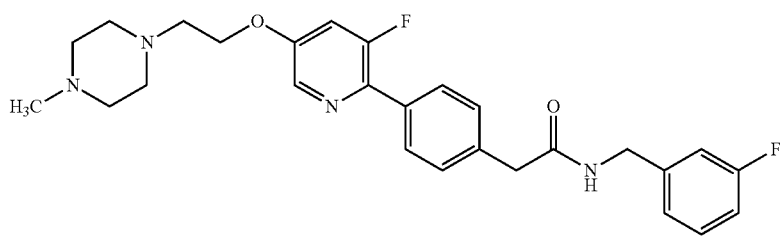 [SMILES: CN1CCN(CCOc2cnc(-c3ccc(CC(=O)NCc4cccc(F)c4)cc3)c(F)c2)CC1]
171
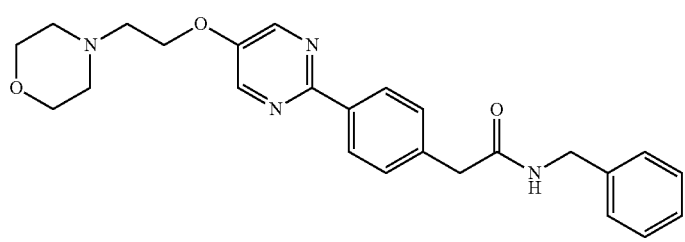 [SMILES: O=C(Cc1ccc(-c2ncc(OCCN3CCOCC3)cn2)cc1)NCc1ccccc1]
172
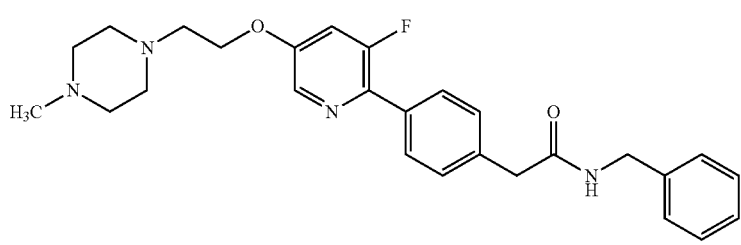 [SMILES: CN1CCN(CCOc2cnc(-c3ccc(CC(=O)NCc4ccccc4)cc3)c(F)c2)CC1]
173
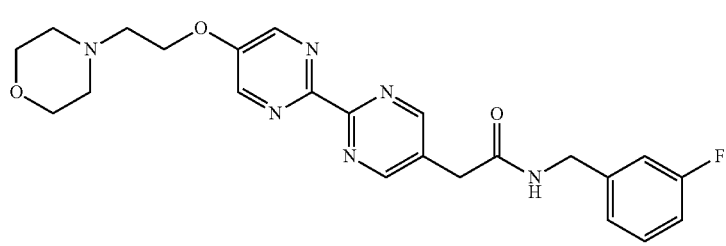 [SMILES: O=C(Cc1cnc(-c2ncc(OCCN3CCOCC3)cn2)nc1)NCc1cccc(F)c1]
174

TABLE 2-continued
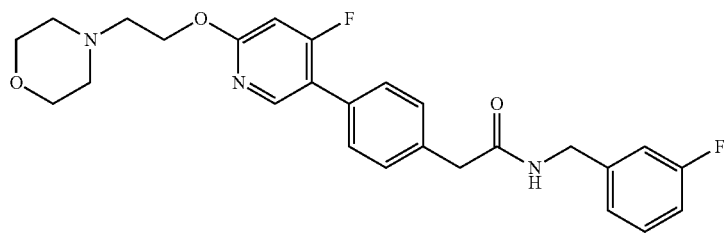 [SMILES: O=C(Cc1ccc(-c2cnc(OCCN3CCOCC3)cc2F)cc1)NCc1cccc(F)c1]
175
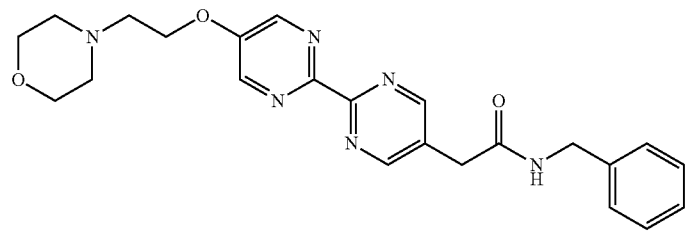 [SMILES: O=C(Cc1cnc(-c2ncc(OCCN3CCOCC3)cn2)nc1)NCc1ccccc1]
176
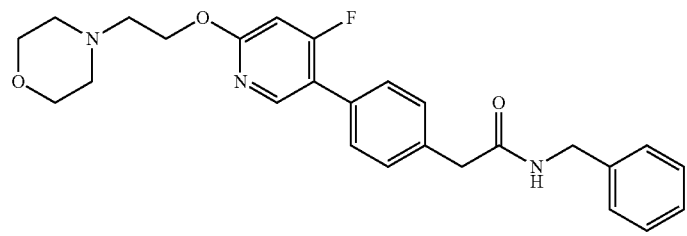
177
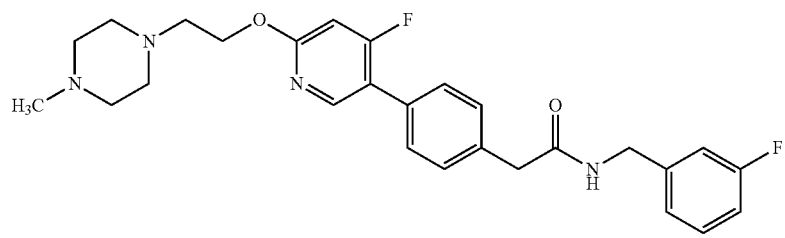 [SMILES: CN1CCN(CCOc2cc(F)c(-c3ccc(CC(=O)NCc4cccc(F)c4)cc3)cn2)CC1]
178
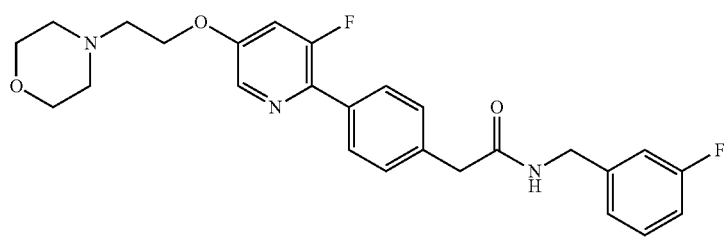 [SMILES: O=C(Cc1ccc(-c2ncc(OCCN3CCOCC3)cc2F)cc1)NCc1cccc(F)c1]
179
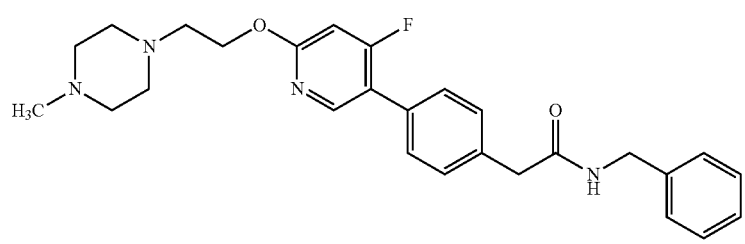 [SMILES: CN1CCN(CCOc2cc(F)c(-c3ccc(CC(=O)NCc4ccccc4)cc3)cn2)CC1]
180

TABLE 2-continued
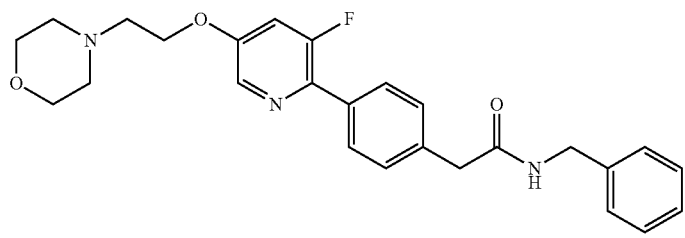 [SMILES: O=C(Cc1ccc(-c2ncc(OCCN3CCOCC3)cc2F)cc1)NCc1ccccc1]
181
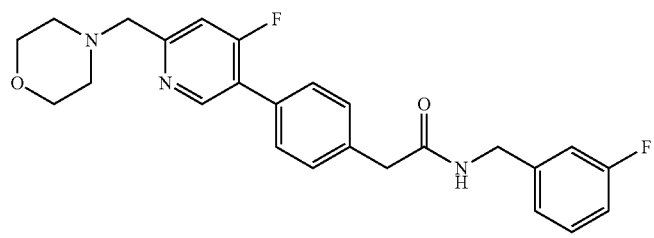 [SMILES: O=C(Cc1ccc(-c2cnc(CN3CCOCC3)cc2F)cc1)NCc1cccc(F)c1]
182
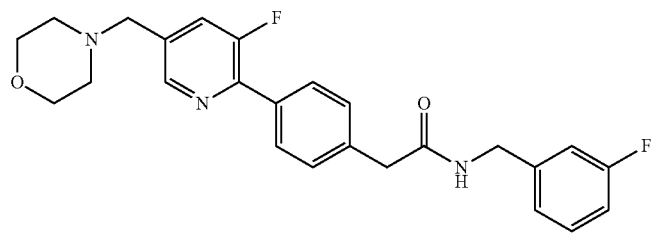 [SMILES: O=C(Cc1ccc(-c2ncc(CN3CCOCC3)cc2F)cc1)NCc1cccc(F)c1]
183
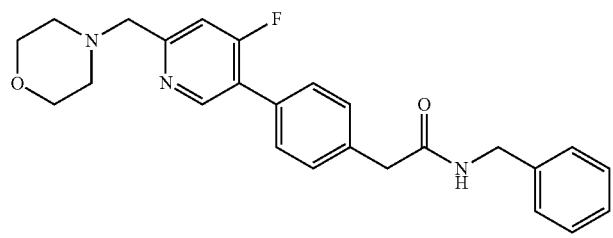
184
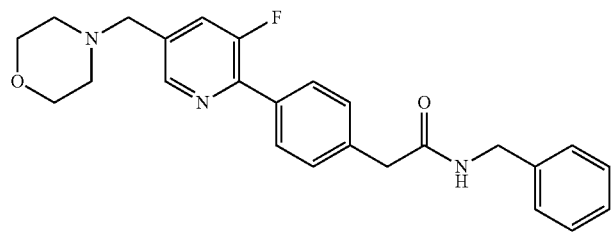
185
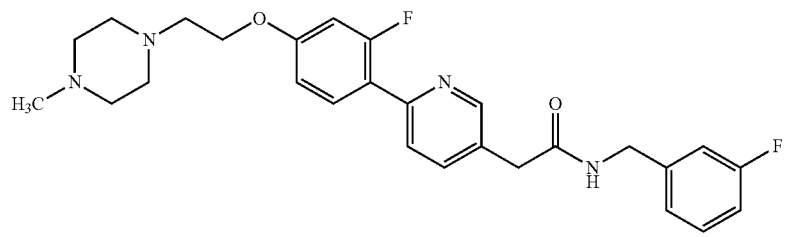
186

TABLE 2-continued
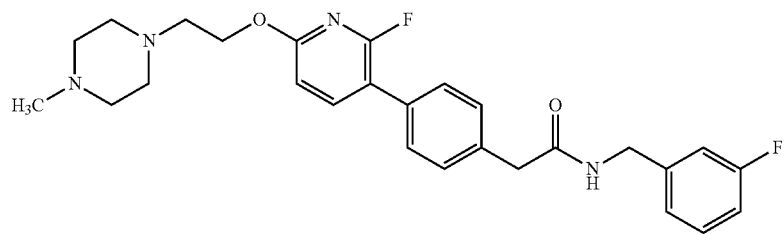 [SMILES: CN1CCN(CCOc2ccc(-c3ccc(CC(=O)NCc4cccc(F)c4)cc3)c(F)n2)CC1]
187
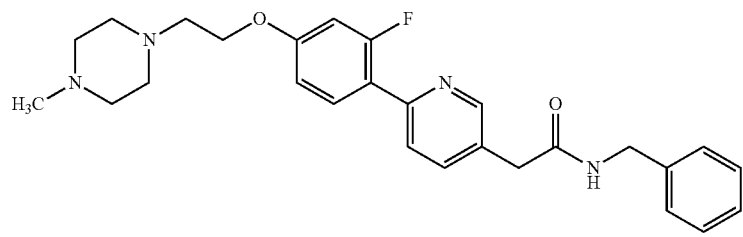 [SMILES: CN1CCN(CCOc2ccc(-c3ccc(CC(=O)NCc4ccccc4)cn3)c(F)c2)CC1]
188
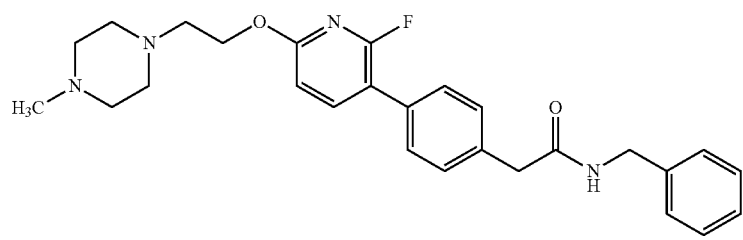 [SMILES: CN1CCN(CCOc2ccc(-c3ccc(CC(=O)NCc4ccccc4)cc3)c(F)n2)CC1]
189
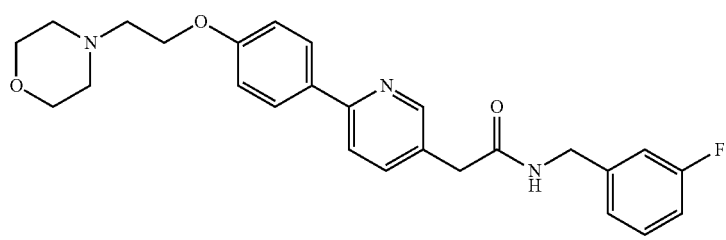 [SMILES: O=C(Cc1ccc(-c2ccc(OCCN3CCOCC3)cc2)nc1)NCc1cccc(F)c1]
190
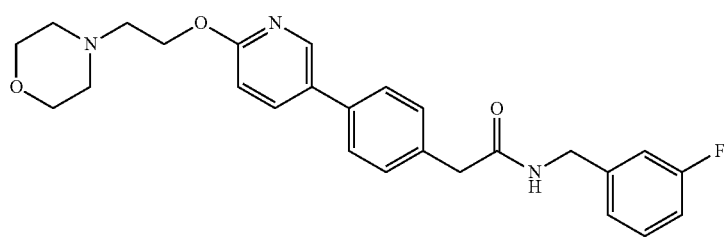 [SMILES: O=C(Cc1ccc(-c2ccc(OCCN3CCOCC3)nc2)cc1)NCc1cccc(F)c1]
191
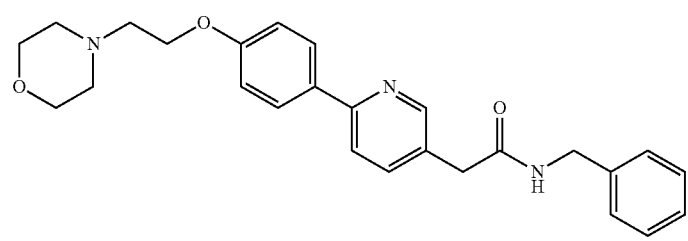 [SMILES: O=C(Cc1ccc(-c2ccc(OCCN3CCOCC3)cc2)nc1)NCc1ccccc1]
192

TABLE 2-continued
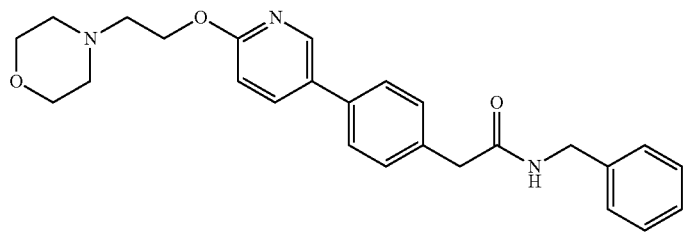
193
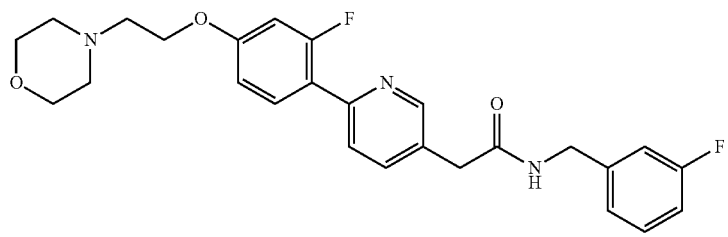 [SMILES: O=C(Cc1ccc(-c2ccc(OCCN3CCOCC3)cc2F)nc1)NCc1cccc(F)c1]
194
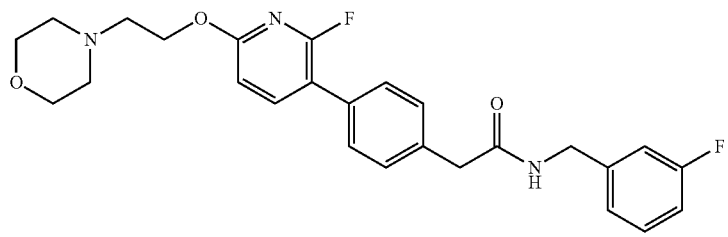
195
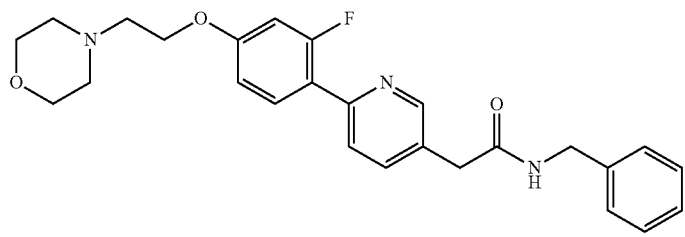 [SMILES: O=C(Cc1ccc(-c2ccc(OCCN3CCOCC3)cc2F)nc1)NCc1ccccc1]
196
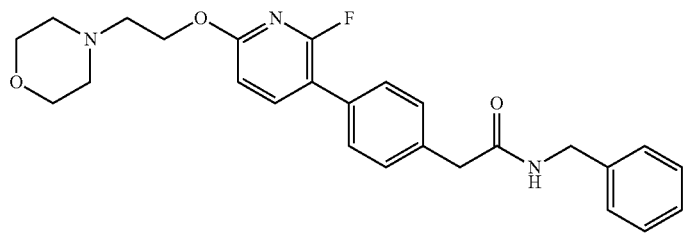 [SMILES: O=C(Cc1ccc(-c2ccc(OCCN3CCOCC3)nc2F)cc1)NCc1ccccc1]
197
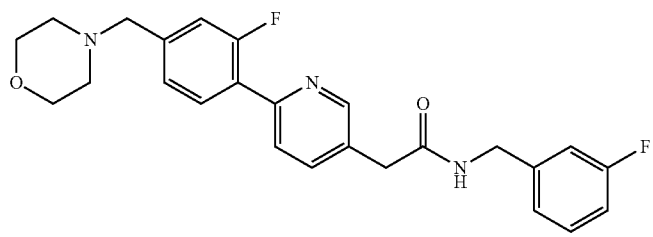 [SMILES: O=C(Cc1ccc(-c2ccc(CN3CCOCC3)cc2F)nc1)NCc1cccc(F)c1]
198

TABLE 2-continued
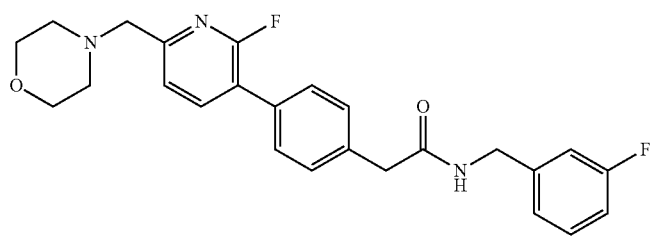 [SMILES: O=C(Cc1ccc(-c2ccc(CN3CCOCC3)nc2F)cc1)NCc1cccc(F)c1]
199
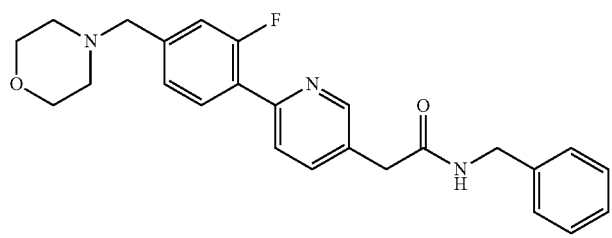
200
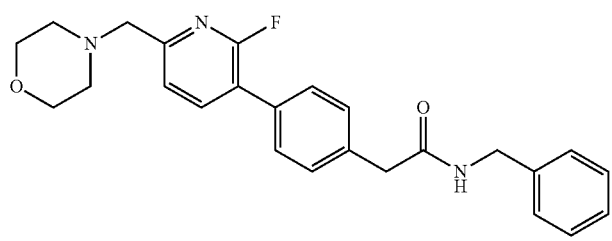
201
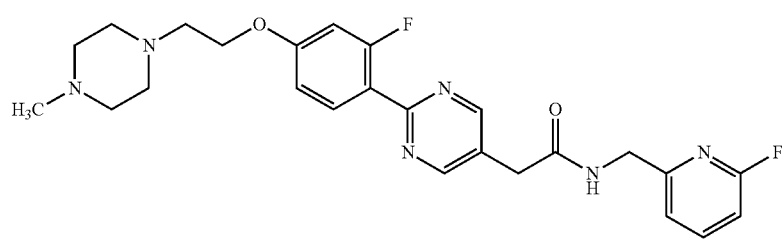
202
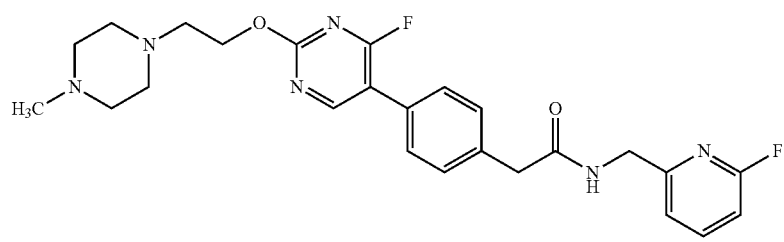
203
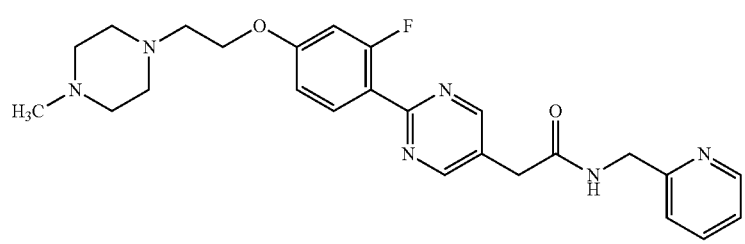 [SMILES: CN1CCN(CCOc2ccc(-c3ncc(CC(=O)NCc4ccccn4)cn3)c(F)c2)CC1]
204

TABLE 2-continued
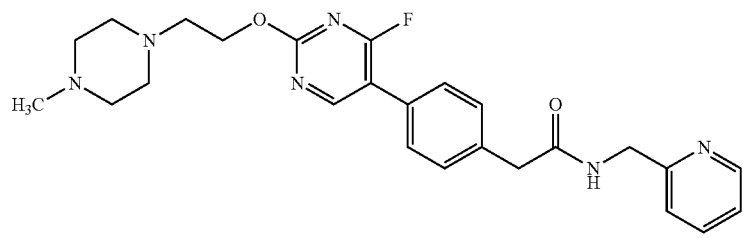 [SMILES: CN1CCN(CCOc2ncc(-c3ccc(CC(=O)NCc4ccccn4)cc3)c(F)n2)CC1]
205
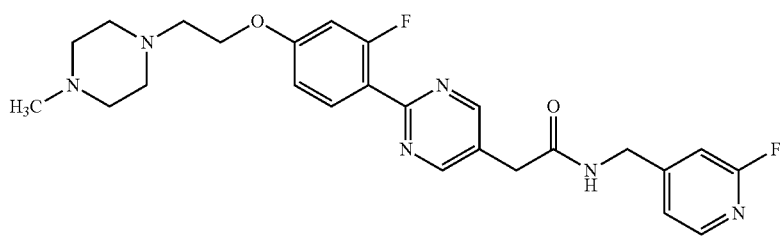
206
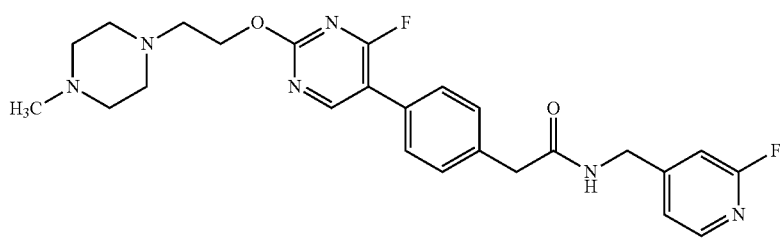
207
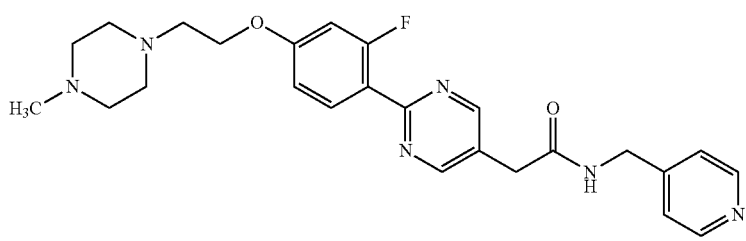 [SMILES: CN1CCN(CCOc2ccc(-c3ncc(CC(=O)NCc4ccncc4)cn3)c(F)c2)CC1]
208
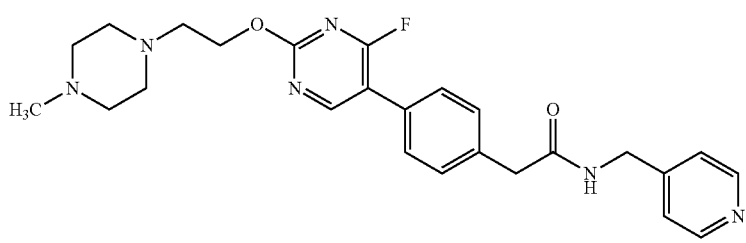
209
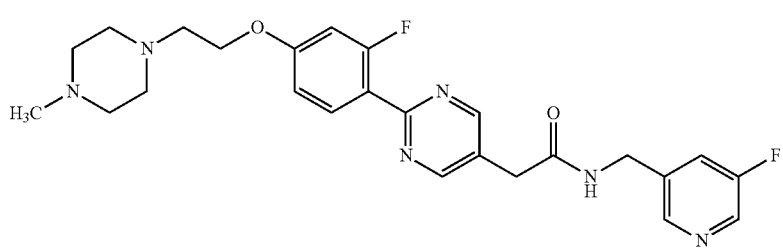 [SMILES: CN1CCN(CCOc2ccc(-c3ncc(CC(=O)NCc4cncc(F)c4)cn3)c(F)c2)CC1]
210

TABLE 2-continued
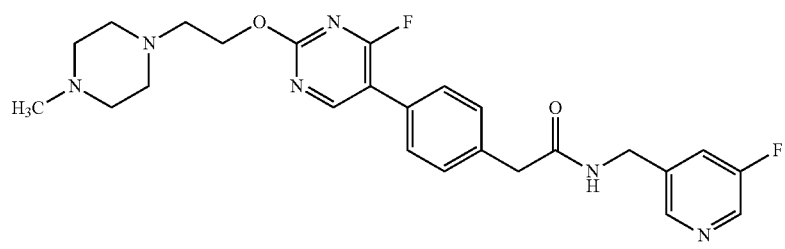 [SMILES: CN1CCN(CCOc2ncc(-c3ccc(CC(=O)NCc4cncc(F)c4)cc3)c(F)n2)CC1]
211
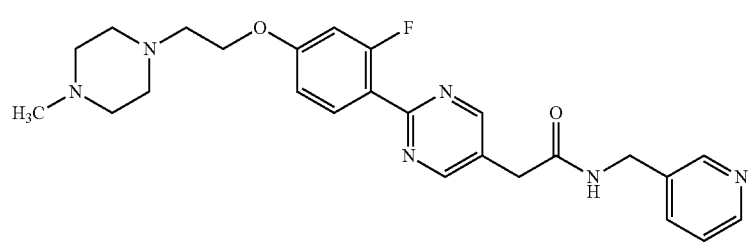 [SMILES: CN1CCN(CCOc2ccc(-c3ncc(CC(=O)NCc4cccnc4)cn3)c(F)c2)CC1]
212
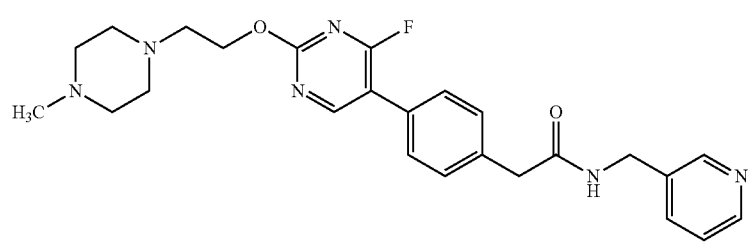 [SMILES: CN1CCN(CCOc2ncc(-c3ccc(CC(=O)NCc4cccnc4)cc3)c(F)n2)CC1]
213
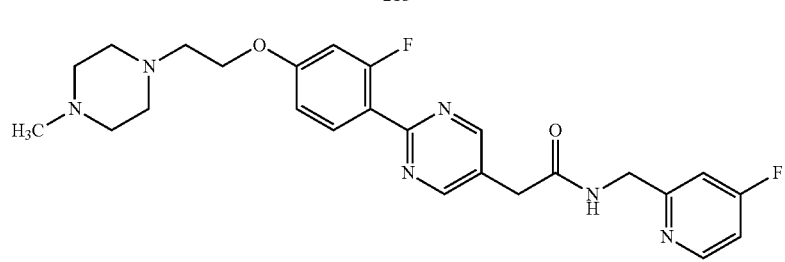
214
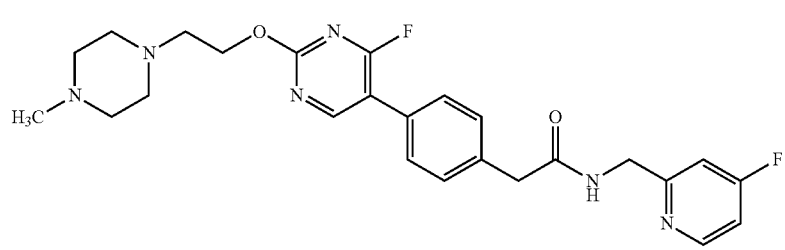
215
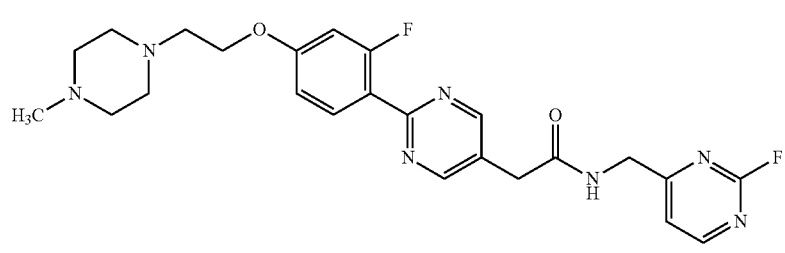 [SMILES: CN1CCN(CCOc2ccc(-c3ncc(CC(=O)NCc4ccnc(F)n4)cn3)c(F)c2)CC1]
216

TABLE 2-continued
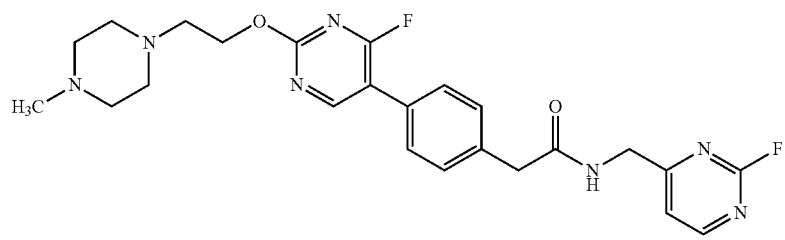 [SMILES: CN1CCN(CCOc2ncc(-c3ccc(CC(=O)NCc4ccnc(F)n4)cc3)c(F)n2)CC1]
217
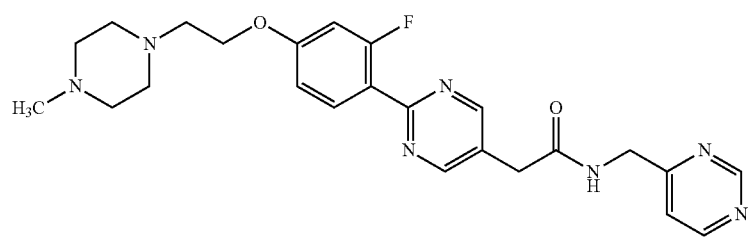 [SMILES: CN1CCN(CCOc2ccc(-c3ncc(CC(=O)NCc4ccncn4)cn3)c(F)c2)CC1]
218
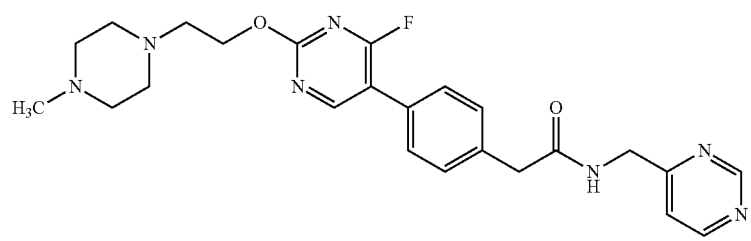 [SMILES: CN1CCN(CCOc2ncc(-c3ccc(CC(=O)NCc4ccncn4)cc3)c(F)n2)CC1]
219
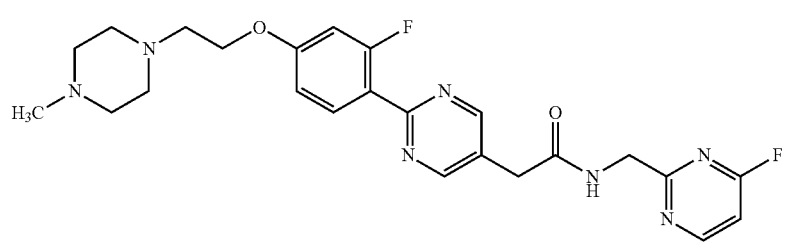
220
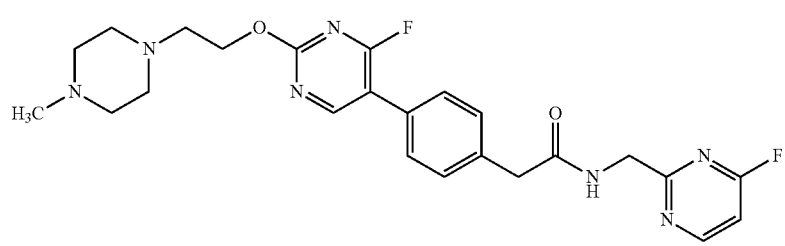 [SMILES: CN1CCN(CCOc2ncc(-c3ccc(CC(=O)NCc4nccc(F)n4)cc3)c(F)n2)CC1]
221
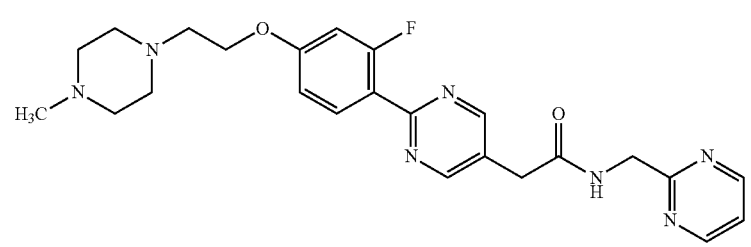
222

TABLE 2-continued
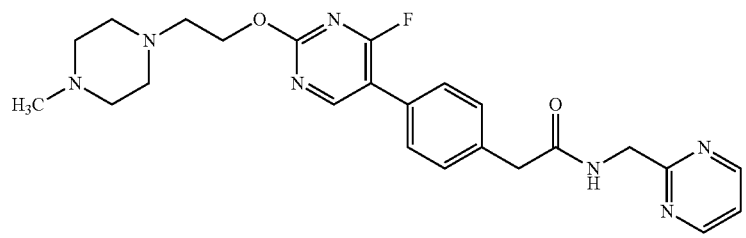
223
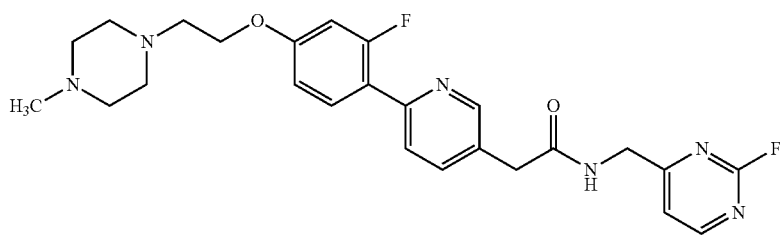
224
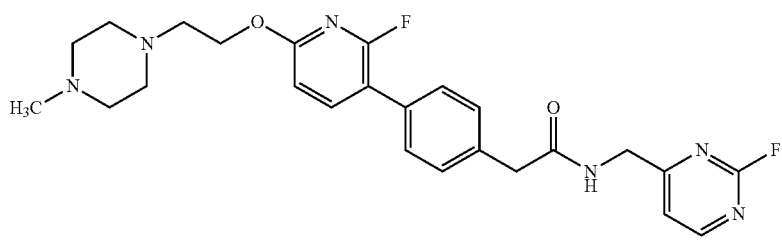 [SMILES: CN1CCN(CCOc2ccc(-c3ccc(CC(=O)NCc4ccnc(F)n4)cc3)c(F)n2)CC1]
225
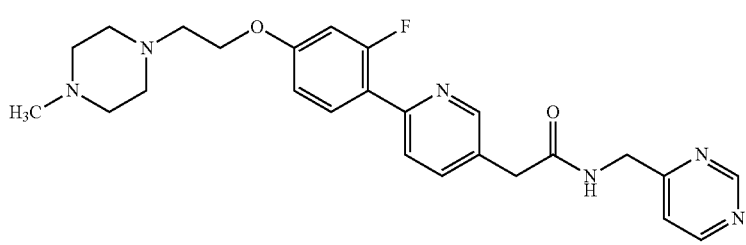 [SMILES: CN1CCN(CCOc2ccc(-c3ccc(CC(=O)NCc4ccncn4)cn3)c(F)c2)CC1]
226
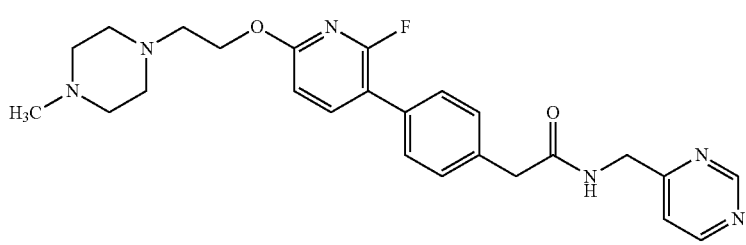 [SMILES: CN1CCN(CCOc2ccc(-c3ccc(CC(=O)NCc4ccncn4)cc3)c(F)n2)CC1]
227
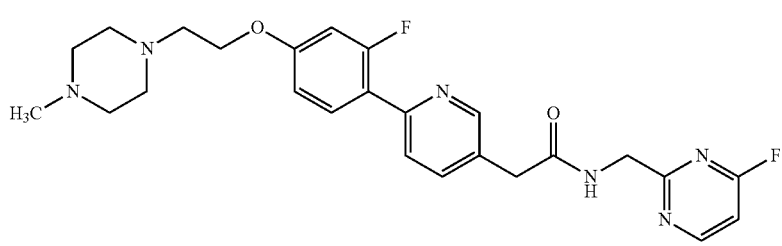 [SMILES: CN1CCN(CCOc2ccc(-c3ccc(CC(=O)NCc4nccc(F)n4)cn3)c(F)c2)CC1]
228

TABLE 2-continued
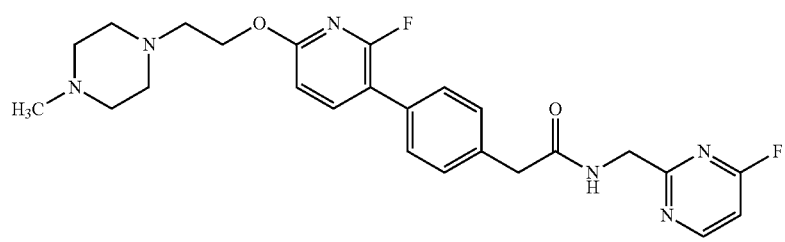
229
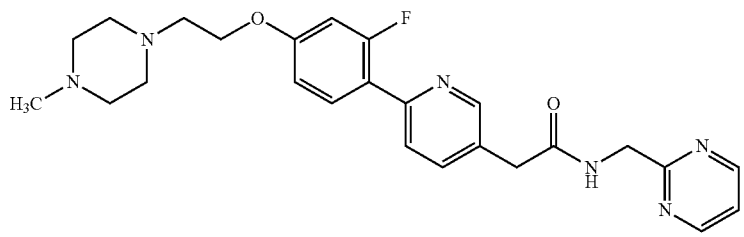
230
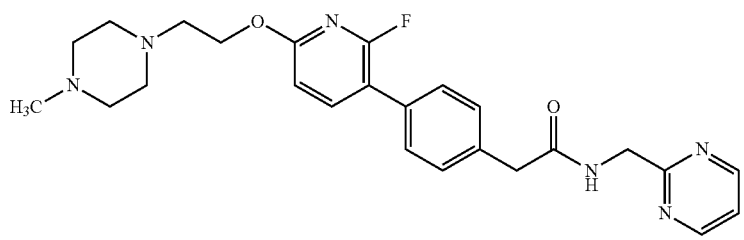 [SMILES: CN1CCN(CCOc2ccc(-c3ccc(CC(=O)NCc4ncccn4)cc3)c(F)n2)CC1]
231
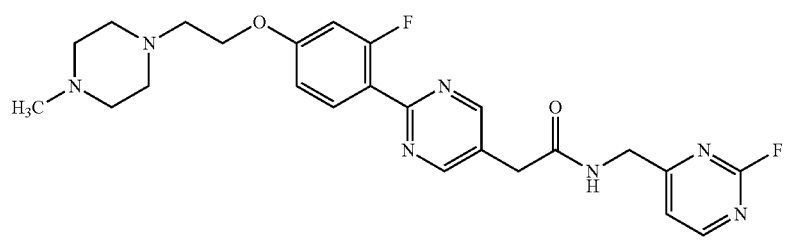
232
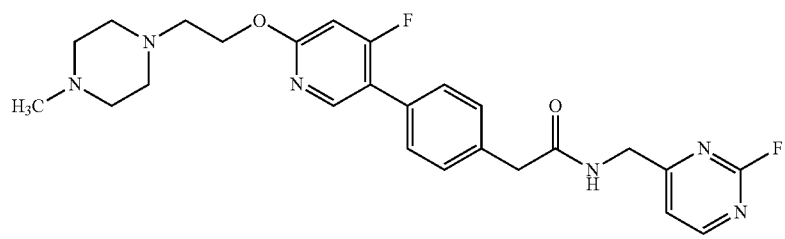
233
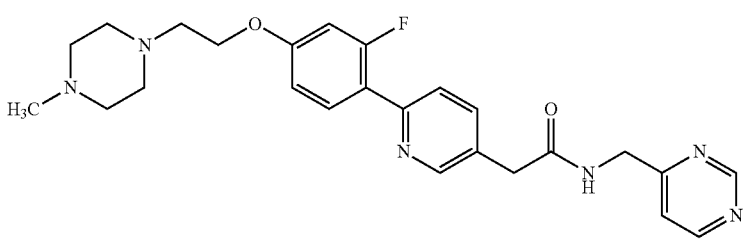
234

TABLE 2-continued
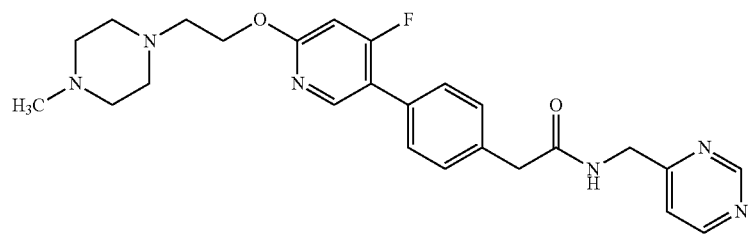
235
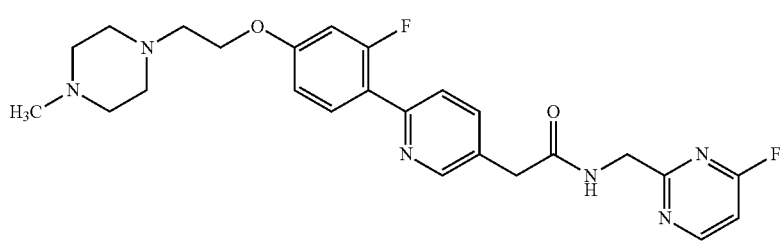
236
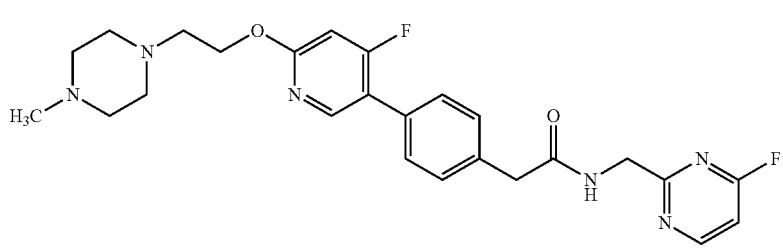 [SMILES: CN1CCN(CCOc2cc(F)c(-c3ccc(CC(=O)NCc4nccc(F)n4)cc3)cn2)CC1]
237
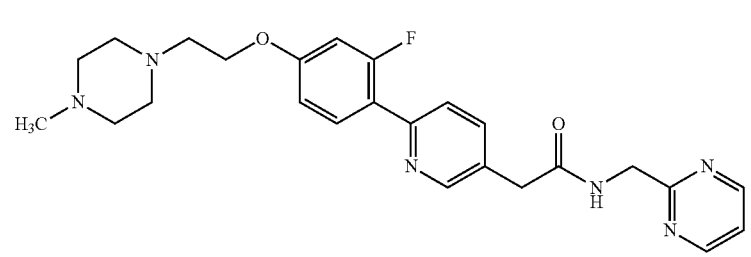
238
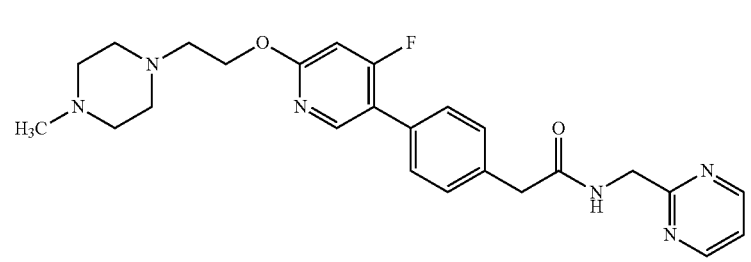
239
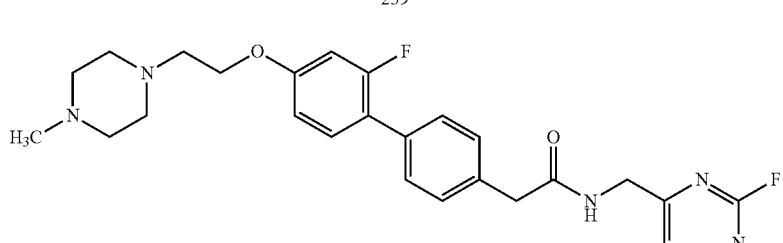
240

TABLE 2-continued
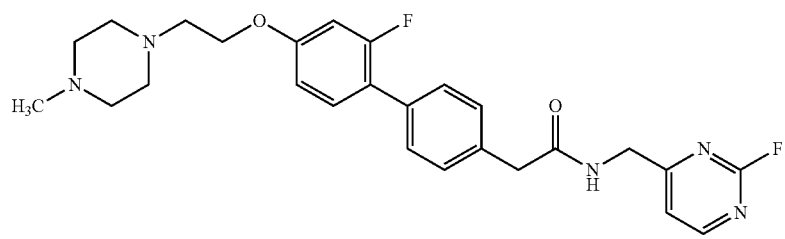 [SMILES: CN1CCN(CCOc2ccc(-c3ccc(CC(=O)NCc4ccnc(F)n4)cc3)c(F)c2)CC1]
241
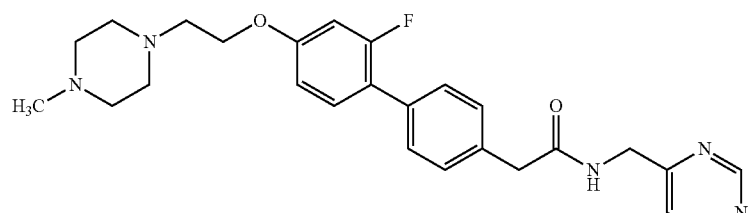
242
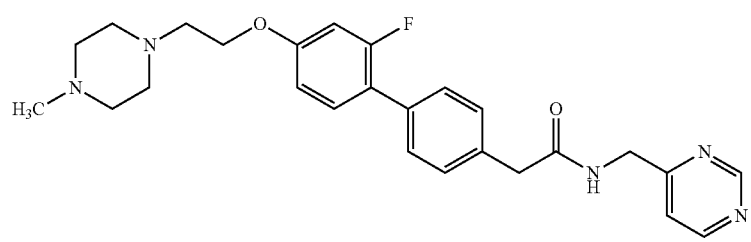 [SMILES: CN1CCN(CCOc2ccc(-c3ccc(CC(=O)NCc4ccncn4)cc3)c(F)c2)CC1]
243
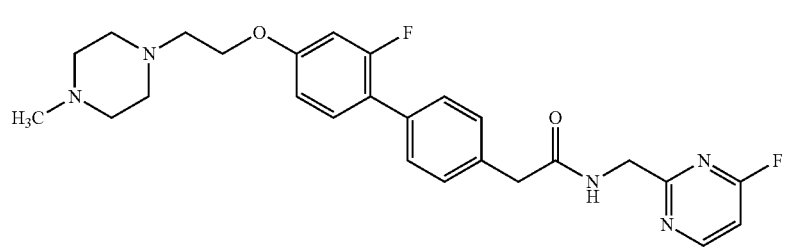
244
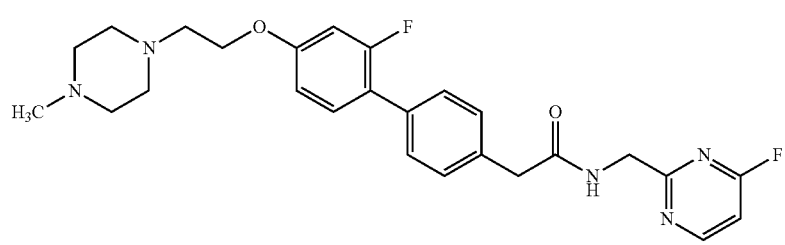 [SMILES: CN1CCN(CCOc2ccc(-c3ccc(CC(=O)NCc4nccc(F)n4)cc3)c(F)c2)CC1]
245
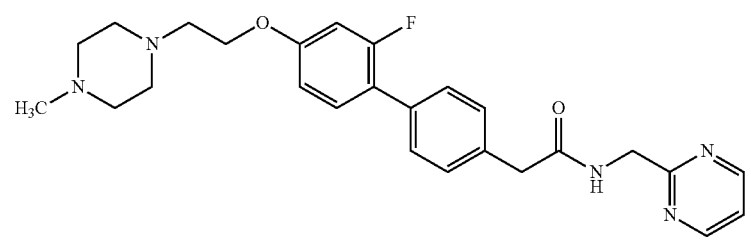 [SMILES: CN1CCN(CCOc2ccc(-c3ccc(CC(=O)NCc4ncccn4)cc3)c(F)c2)CC1]
246

TABLE 2-continued

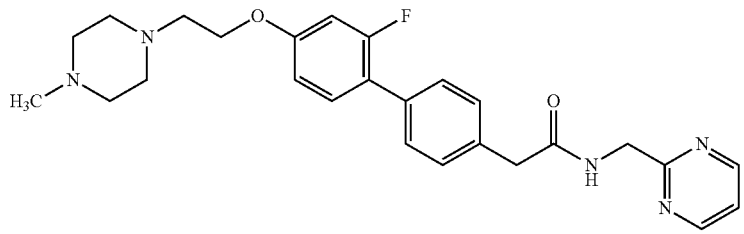 [SMILES: CN1CCN(CCOc2ccc(-c3ccc(CC(=O)NCc4ncccn4)cc3)c(F)c2)CC1]

247

Compounds of the invention include compounds of Formula IA, and pharmaceutically acceptable salts, solvates, hydrates, or prodrugs thereof:

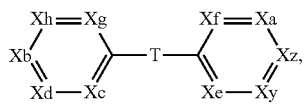

(Formula IA)

wherein: T is absent (i.e., the rings are connected by a bond), $CR_{12}R_{13}$, C(O), O, S, S(O), S(O)$_2$, $NR_{14}$, $C(R_{15}R_{16})C(R_{17}R_{18})$, $CH_2O$, or $OCH_2$;

$X_y$ is CZ, CY, N, or N—O;

$X_z$ is CZ, CY, N, or N—O;

at least one of $X_y$ and $X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$X_f$ is $CR_4$, N, or N—O;

$X_g$ is $CR_5$, N, or N—O;

$X_h$ is $CR_6$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, SO$_2$H, SO$_2$-lower ($C_1$, $C_2$, $C_3$, $C_4$, $C_5$, or $C_6$) alkyl,

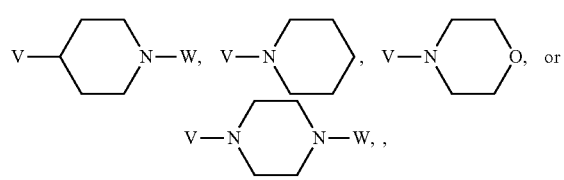

wherein W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is SO$_3$H, OSO$_3$H, PO$_3$H$_2$, OPO$_3$H$_2$, NH$_2$, NHR$_{19}$, NR$_{20}$R$_{21}$,

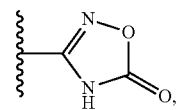 [SMILES: *c1noc(=O)[nH]1]

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is aryl, heteroaryl, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower $C_1$, $C_2$, $C_3$, $C_4$, $C_5$, $C_6$ alkoxy, tetrazole, or

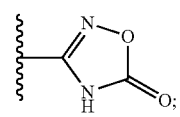 [SMILES: *c1noc(=O)[nH]1]

L is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{49}$R$_{20}$, SO$_2$R$_{21}$, glycoside, lower $C_1$, $C_2$, $C_3$, $C_4$, $C_5$, $C_6$ alkoxy, tetrazole, or

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower $C_1$, $C_2$, $C_3$, $C_4$, $C_5$, $C_6$ alkoxy, tetrazole, or Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower $C_1$, $C_2$, $C_3$, $C_4$, $C_5$, $C_6$ alkoxy, tetrazole, or $R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

V is a bond, $-CH_2-$, $-CH_2CH_2-$, $-CH_2CH_2CH_2-$, $-O-CH_2-$, $-OCH_2CH_2-$ or $-OCH_2CH_2CH_2-$;

$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl; and Z is $(CHR_1)_n-C(O)-NR_2(CHR_3)_m-Ar$, where Ar is a substituted or unsubstituted aryl or nitrogen-containing heteroaryl group, $R_1$, $R_2$, and $R_3$ are independently H or $C_1$, $C_2$, $C_3$, $C_4$, $C_5$, or $C_6$ alkyl; and n and m are, independently 0, 1, or 2;

provided that at least one of $R_a$, $R_b$, $R_c$, $R_d$, $R_e$, $R_4$, $R_5$, and $R_6$ is P.

In one embodiment, only one of $R_a$, $R_b$, $R_c$, $R_d$, $R_e$, $R_4$, $R_5$ and $R_6$ is P.

In one embodiment of the invention, at least one of $X_a$, $X_b$, $X_c$, $X_d$, $X_e$, $X_f$, $X_g$, $X_h$, $X_y$, and $X_z$ is N. In another embodiment, at least two of $X_a$, $X_b$, $X_c$, $X_d$, $X_e$, $X_f$, $X_g$, $X_h$, $X_y$, and $X_z$ are N. In another embodiment, at least one of $X_a$ and $X_y$ is N. For example, both $X_a$ and $X_y$ are N. In another embodiment, $X_a$, $X_b$, $X_c$, $X_d$, $X_e$, $X_f$, $X_g$ and $X_h$ are not each N or N—O. In another embodiment, $X_c$, $X_d$, and $X_e$ are not each N or N—O.

In one embodiment, $X_a$ is N. In one embodiment, $X_b$ is N. In one embodiment, $X_c$ is N. In one embodiment, $X_d$ is N. In one embodiment, $X_e$ is N. In one embodiment, $X_f$ is N. In one embodiment, $X_g$ is N. In one embodiment, $X_h$ is N.

In one embodiment, $X_a$ and $X_y$ are each N. In one embodiment, $X_e$ and $X_f$ are each N. In one embodiment, $X_c$ and $X_g$ are each N. In one embodiment, $X_d$ and $X_h$ are each N.

In one embodiment, $X_e$, $X_f$, $X_c$ and $X_g$ are each N.

In one embodiment, T is absent e.g., a bond. In another embodiment, $X_b$ is $CR_b$. In another embodiment, $R_b$ is P. For example, in one embodiment, P is O-lower ($C_1$, $C_2$, $C_3$, $C_4$, $C_5$, or $C_6$) alkyl-K: In one embodiment, lower ($C_1$, $C_2$, $C_3$, $C_4$, $C_5$, or $C_6$) alkyl is $CH_2CH_2CH_2$. In one embodiment, lower ($C_1$, $C_2$, $C_3$, $C_4$, $C_5$, or $C_6$) alkyl is branched alkyl. For example, branched alkyl is

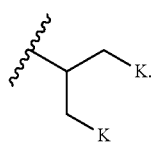

In another embodiment, K, L, M, or Q, if present, is lower $C_1$, $C_2$, $C_3$, $C_4$, $C_5$ or $C_6$ alkoxy. For example, K is methoxy. In one embodiment, branched alkyl is

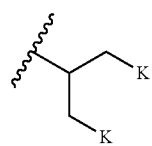

and K is methoxy. In another embodiment, K, L, M, or Q, if present, is COOH. For example, in one embodiment, K is COOH. In another embodiment, K, L, M, or Q, if present, is aryl or heteroaryl. For example, heteroaryl is tetrazole.

In one embodiment, $R_b$ is

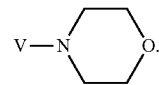

In another embodiment, $R_b$ is

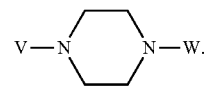

In one embodiment, V is $-OCH_2CH_2$. In another embodiment, V is a bond. In one embodiment, W is $C_1$, $C_2$, $C_3$, $C_4$, $C_5$, or $C_6$ alkyl. For example, W is methyl or ethyl.

In one embodiment, $X$, is CZ, further wherein Z is

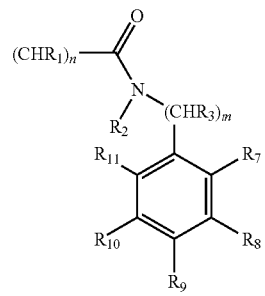

and $R_7$, $R_8$, $R_9$, $R_{10}$, and $R_{11}$ are selected from hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$ alkyl-O—$C_1$, $C_2$, $C_3$, $C_4$, $C_5$, or $C_6$ alkyl, where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl. In another embodiment, at least one of $R_7$, $R_8$, $R_9$, $R_{10}$, and $R_{11}$ is halogen, $C_1$, $C_2$, $C_3$, $C_4$, $C_5$, or $C_6$ alkoxy, or O-benzyl. In another embodiment, at least one of $R_8$ or $R_{10}$ is halogen. For example, halogen is fluorine. In another embodiment, at least one of $R_7$ or $R_{11}$ is $C_1$, $C_2$, $C_3$, $C_4$, $C_5$, or $C_6$ alkoxy or O-benzyl. For example, at least one of $R_7$ or $R_{11}$ is ethoxy or at least one of $R_7$ or $R_{11}$ is O-benzyl. In one embodiment, $R_1$ is H. In one embodiment, n is 1. In one embodiment, $R_2$ is H. In one embodiment, $R_3$ is H. In one embodiment, m is 1. In another embodiment, m and n are each 1 and $R_2$ and $R_3$ are each H.

In one embodiment, $R_4$ and $R_6$ are each H. In another embodiment $R_5$ is selected from halogen and $C_1$, $C_2$, $C_3$, $C_4$, $C_5$, or $C_6$ alkyl. In one embodiment, $R_5$ is halogen. For example, $R_5$ is Cl or F. In another embodiment, $R_5$ is $C_1$, $C_2$, $C_3$, $C_4$, $C_5$, or $C_6$ alkyl. For example, $R_5$ is methyl or ethyl.

In another embodiment, $R_b$ is not hydrogen.

The invention includes a solvate of a compound according to Formula IA. The invention includes a hydrate of compound according to Formula IA. The invention includes an acid addition salt of a compound according to Formula IA. For example, a hydrochloride salt. In another embodiment, the invention includes a pharmaceutically acceptable salt. The invention includes a composition comprising a compound of Formula IA and at least one pharmaceutically acceptable excipient.

Certain compounds of the invention include compounds selected from Table 3.

TABLE 3

| Compound # | Structure |
|---|---|
| 248 | 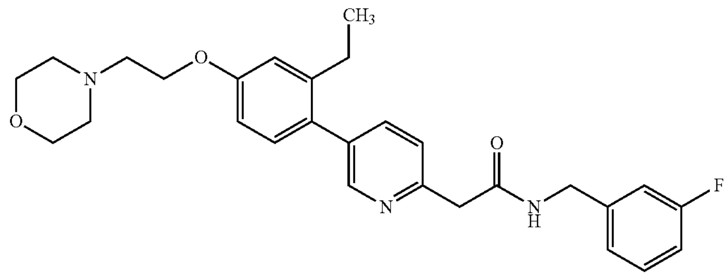 [SMILES: CCc1cc(OCCN2CCOCC2)ccc1-c1ccc(CC(=O)NCc2cccc(F)c2)nc1] |
| 249 | 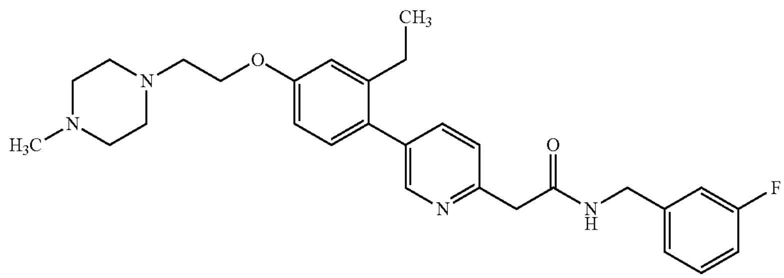 [SMILES: CCc1cc(OCCN2CCN(C)CC2)ccc1-c1ccc(CC(=O)NCc2cccc(F)c2)nc1] |
| 250 | 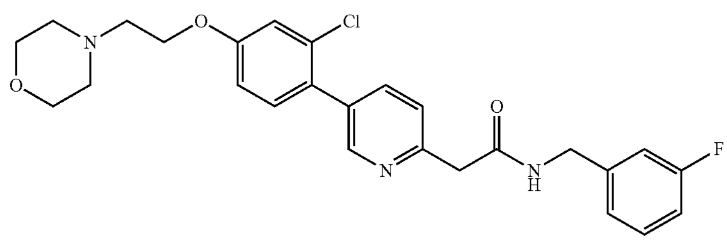 [SMILES: O=C(Cc1ccc(-c2ccc(OCCN3CCOCC3)cc2Cl)cn1)NCc1cccc(F)c1] |
| 251 | 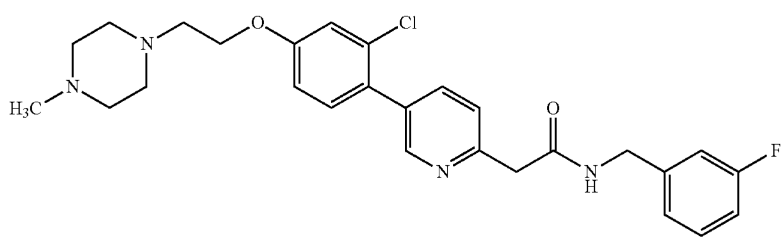 [SMILES: CN1CCN(CCOc2ccc(-c3ccc(CC(=O)NCc4cccc(F)c4)nc3)c(Cl)c2)CC1] |
| 252 | 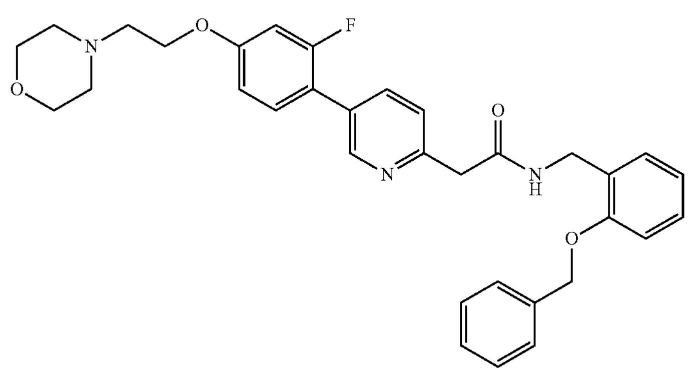 [SMILES: O=C(Cc1ccc(-c2ccc(OCCN3CCOCC3)cc2F)cn1)NCc1ccccc1OCc1ccccc1] |

TABLE 3-continued

| Compound # | Structure |
|---|---|
| 253 | 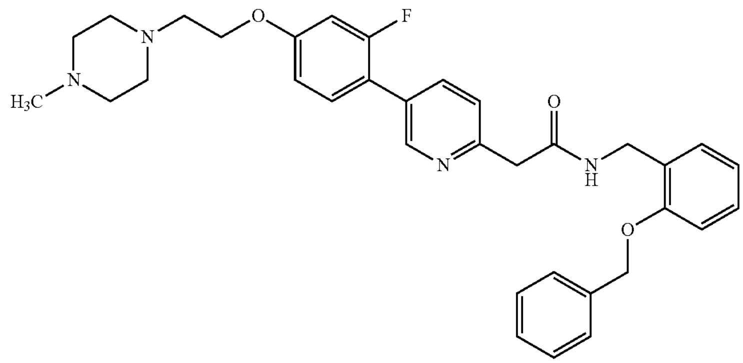 [SMILES: CN1CCN(CCOc2ccc(-c3ccc(CC(=O)NCc4ccccc4OCc4ccccc4)nc3)c(F)c2)CC1] |
| 254 | 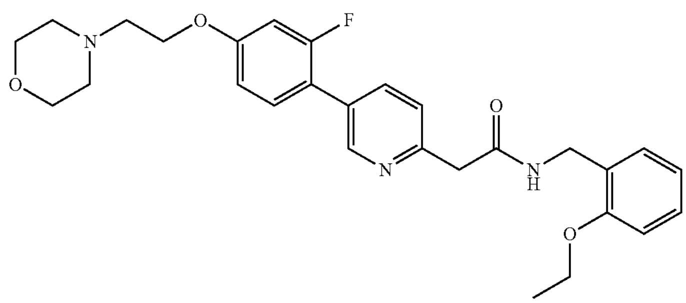 [SMILES: CCOc1ccccc1CNC(=O)Cc1ccc(-c2ccc(OCCN3CCOCC3)cc2F)cn1] |
| 255 | 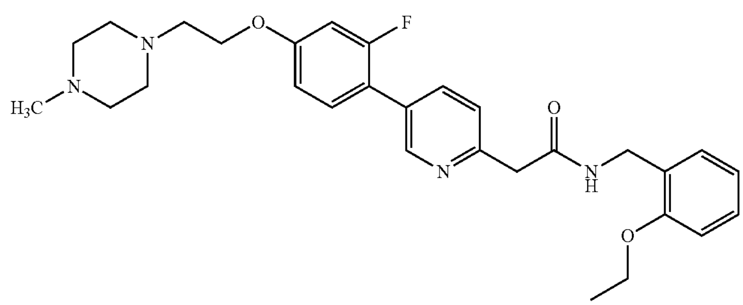 [SMILES: CCOc1ccccc1CNC(=O)Cc1ccc(-c2ccc(OCCN3CCN(C)CC3)cc2F)cn1] |
| 256 | 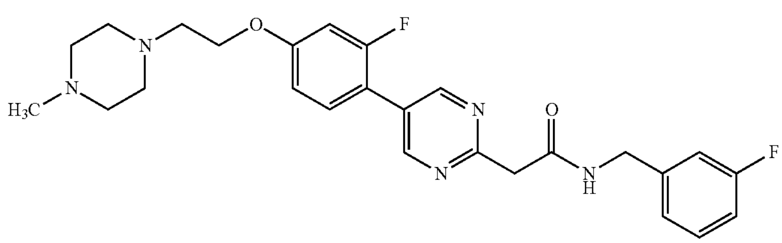 |
| 257 | 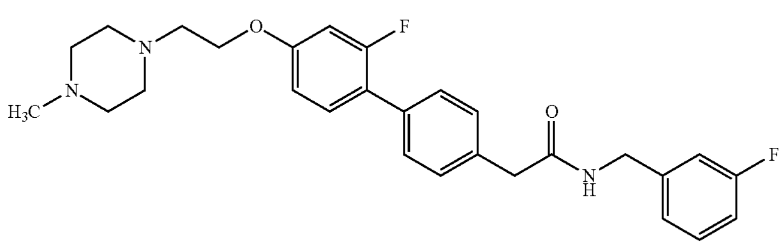 [SMILES: CN1CCN(CCOc2ccc(-c3ccc(CC(=O)NCc4cccc(F)c4)cc3)c(F)c2)CC1] |

TABLE 3-continued

| Compound # | Structure |
|---|---|
| 258 | HO₂C-(CH₂)₃-O-[2-F-phenyl]-5-(pyridin-2-yl)-CH₂-C(O)-NH-CH₂-(3-F-phenyl) |
| 259 | (CH₃OCH₂)₂CH-O-[2-F-phenyl]-5-(pyridin-2-yl)-CH₂-C(O)-NH-CH₂-(3-F-phenyl) |
| 260 | 4-ethylpiperazin-1-yl-CH₂CH₂-O-[2-F-phenyl]-5-(pyridin-2-yl)-CH₂-C(O)-NH-CH₂-(3-F-phenyl) |
| 261 | morpholin-4-yl-[2-F-phenyl]-5-(pyridin-2-yl)-CH₂-C(O)-NH-CH₂-(3-F-phenyl) |
| 262 | (1H-tetrazol-5-yl)-CH₂CH₂-O-[2-F-phenyl]-5-(pyridin-2-yl)-CH₂-C(O)-NH-CH₂-(3-F-phenyl) |
| 263 | 4-methylpiperazin-1-yl-CH₂CH₂-O-[2-CH₃-phenyl]-5-(pyridin-2-yl)-CH₂-C(O)-NH-CH₂-(3-F-phenyl) |

TABLE 3-continued

| Compound # | Structure |
|---|---|
| 264 | 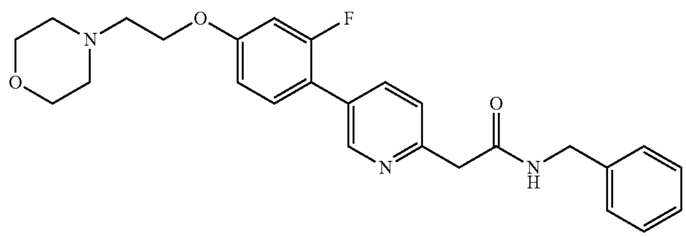 [SMILES: O=C(Cc1ccc(-c2ccc(OCCN3CCOCC3)cc2F)cn1)NCc1ccccc1] |
| 265 | 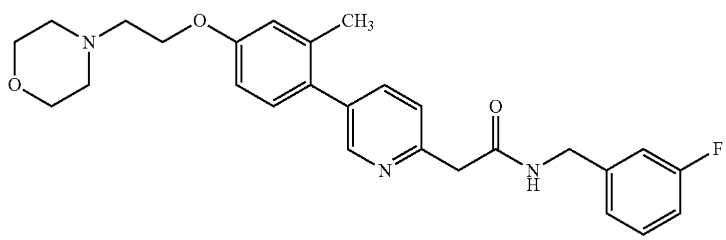 [SMILES: Cc1cc(OCCN2CCOCC2)ccc1-c1ccc(CC(=O)NCc2cccc(F)c2)nc1] |
| 266 | 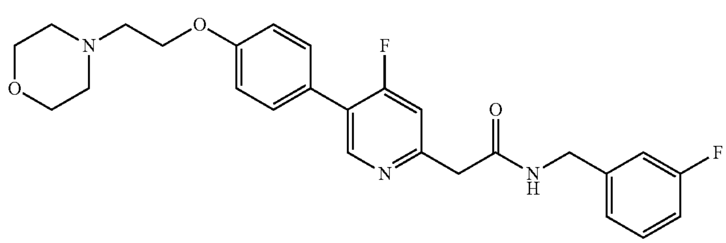 [SMILES: O=C(Cc1cc(F)c(-c2ccc(OCCN3CCOCC3)cc2)cn1)NCc1cccc(F)c1] |
| 267 | 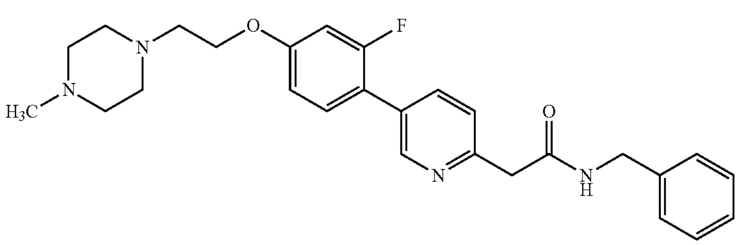 [SMILES: CN1CCN(CCOc2ccc(-c3ccc(CC(=O)NCc4ccccc4)nc3)c(F)c2)CC1] |
| 268 | 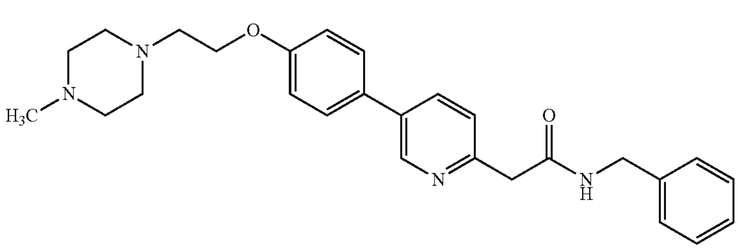 [SMILES: CN1CCN(CCOc2ccc(-c3ccc(CC(=O)NCc4ccccc4)nc3)cc2)CC1] |
| 269 | 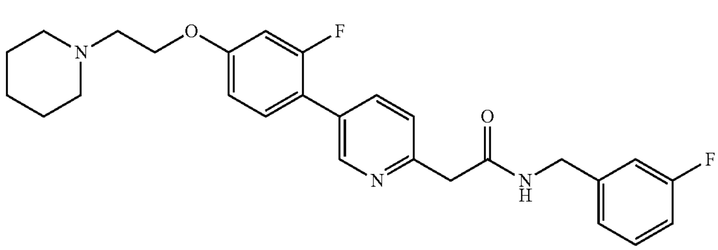 [SMILES: O=C(Cc1ccc(-c2ccc(OCCN3CCCCC3)cc2F)cn1)NCc1cccc(F)c1] |

TABLE 3-continued

| Compound # | Structure |
|---|---|
| 270 | 2-(5-(2-chloro-4-morpholinophenyl)pyridin-2-yl)-N-(3-fluorobenzyl)acetamide |
| 271 | 2-(5-(2-ethyl-4-morpholinophenyl)pyridin-2-yl)-N-(3-fluorobenzyl)acetamide |
| 272 | N-(3-fluorobenzyl)-2-(5-(4-morpholinophenyl)pyrimidin-2-yl)acetamide |
| 273 | N-(2-ethoxybenzyl)-2-(5-(4-morpholinophenyl)pyridin-2-yl)acetamide |

TABLE 3-continued

| Compound # | Structure |
|---|---|
| 274 | 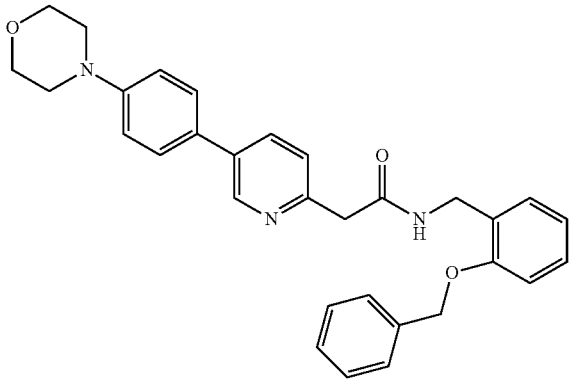 [SMILES: O=C(Cc1ccc(-c2ccc(N3CCOCC3)cc2)cn1)NCc1ccccc1OCc1ccccc1] |

With respect to the chemical compounds disclosed in the present invention, the terms used herein, where applicable, are described in U.S. Pat. No. 7,300,931 and PCT publication no. WO 2008/144045. Methods of preparing compounds disclosed herein are described in U.S. Pat. No. 7,300,931 and in PCT publication no. WO 2008/144045 A1. These patents and publications are incorporated herein by reference in their entireties for all purposes.

For example, Compound 134 and its salts can be prepared as follows.

The synthesis of 4-(2-(4-(6-fluoropyridin-3-yl)phenoxy)ethyl)morpholine is shown in the scheme below:

4-(2-(4-(6-fluoropyridin-3-yl)phenoxy)ethyl)morpholine (5) was synthesized in 3 steps. Intermediate 2 was synthesized using an ether coupling reaction e.g., using Williamson ether synthesis. Ether formation between 4-(2-chloroethyl)morpholine (1) and 4-bromophenol was carried out in the presence of potassium carbonate and DMF to afford 4-(2-(4-bromophenoxy)ethyl)morpholine (2). Rigorously dry conditions were not essential for this reaction and a basic wash with sodium hydroxide was used to remove any remaining 4-bromophenol. In another aspect of the invention, intermediate 2 is synthesized using any ether formation reaction. Intermediate 2 is synthesized starting from compound 1 containing any leaving group. For example, the skilled chemist would start with compounds of the general formula:

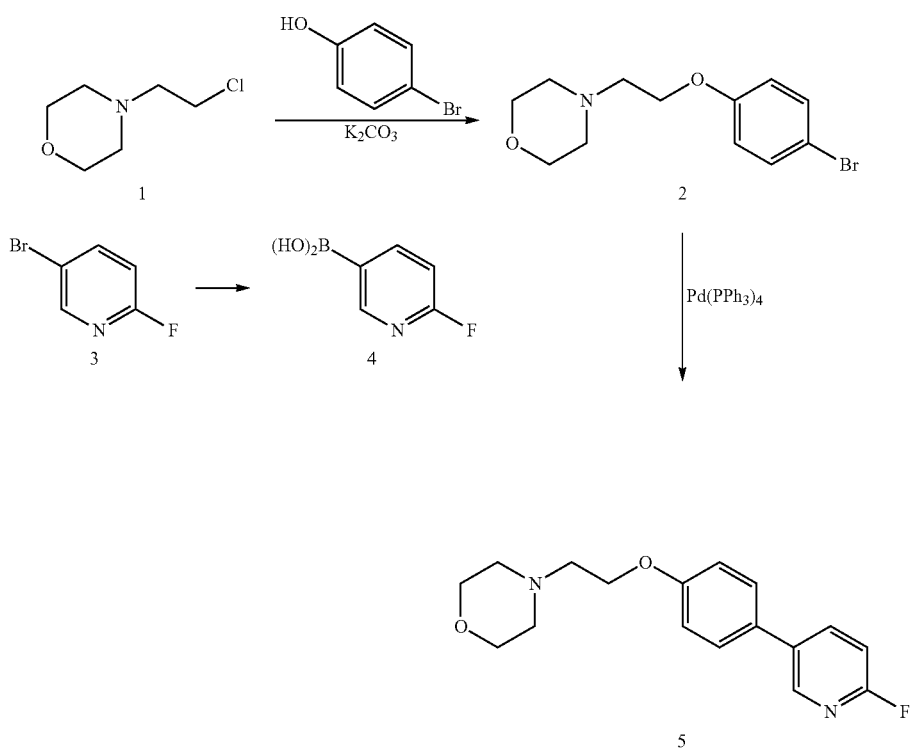

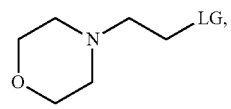

wherein the leaving group "LG" includes but is not limited to halogen, tosylate, mesylate, trifluate, etc.

Compound 5 was formed using a Suzuki reaction. Formation of the aryl borate, 6-fluoropyridin-3-yl-3-boronic acid (4), was carried out by forming the aryl anion using n-BuLi followed by in situ quenching with triisopropylborate (Li, et al., *J. Org. Chem.* 2002, 67, 5394-5397). The resulting 6-fluoropyridin-3-yl-3-boronic acid (4) was coupled to 4-(2-(4-bromophenoxy)ethyl)morpholine (2) in a solution of DME and aqueous sodium carbonate using tetrakis(triphenylphosphine)palladium to afford 4-(2-(4-(6-fluoropyridin-3-yl)phenoxy)ethyl)morpholine (5), which was purified using silica gel chromatography. The skilled chemist would know that other transition metal coupling reaction are used to prepare compound 5.

The synthesis of 2-(5-(4-(2-morpholinoethoxy)phenyl)pyridin-2-yl)-N-benzylacetamide dihydrochloride is shown below:

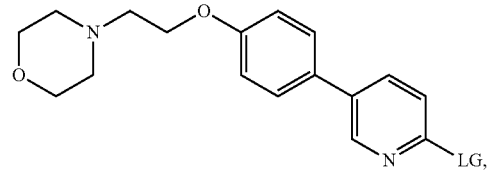

would be pursued where LG includes other leaving groups known to the skilled chemist.

Acid catalyzed methanolysis of 2-(5-(4-(2-morpholinoethoxy)phenyl)pyridin-2-yl)acetonitrile (6) was carried out using a mixture of concentrated sulfuric and fuming sulfuric acid. The use of fuming sulfuric acid removed residual water from the reaction mixture and reduced the amount of carboxylic acid by-product formed. The reaction mixture was quenched by adding the reaction mixture to a solution of saturated sodium bicarbonate and dichloromethane while maintaining the temperature below 20° C. Any carboxylic acid contaminant was readily removed with aqueous work-up. In another aspect of the invention, other acid catalyzed conditions are used by the skilled artisan for alcoholysis of the nitrile of compound 6 to produce compound 7.

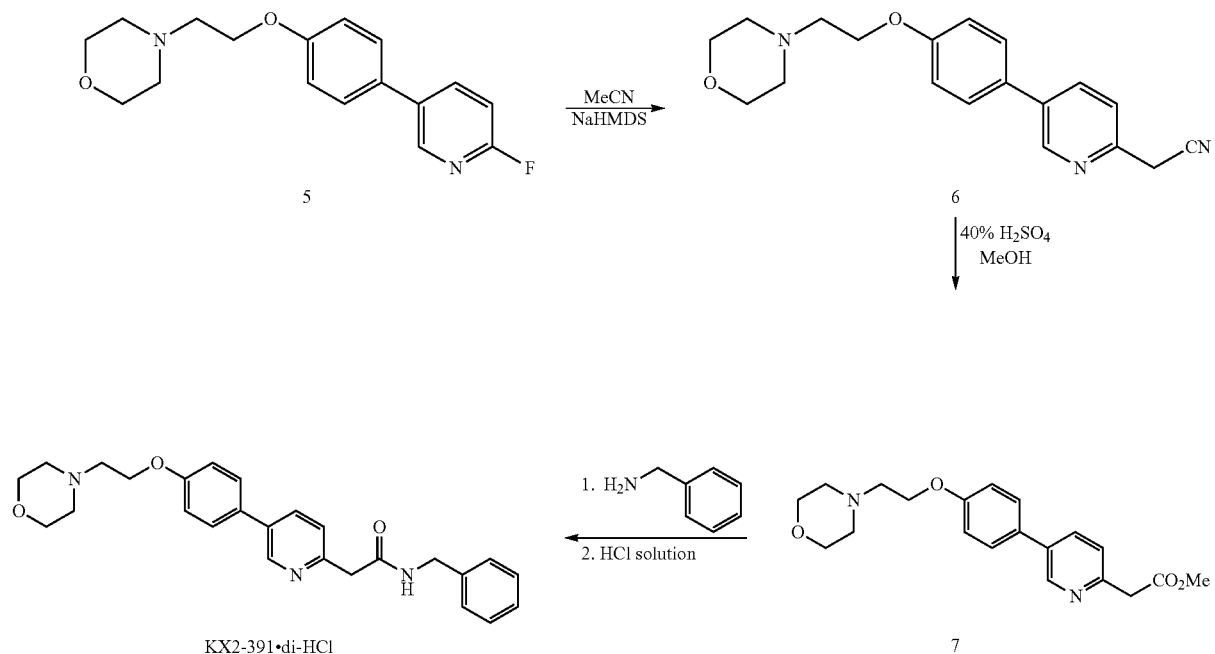

2-(5-(4-(2-morpholinoethoxy)phenyl)pyridin-2-yl)-N-benzylacetamide dihydrochloride (Compound 134•HCl) was synthesized in four linear steps. The fluoride of 4-(2-(4-(6-fluoropyridin-3-yl)phenoxy)ethyl)morpholine (5) was displaced by the anion of acetonitrile formed using commercially available NaHMDS. Acetonitrile was added slowly to a cooled mixture of compound 5 and base to form 2-(5-(4-(2-morpholinoethoxy)phenyl)pyridin-2-yl)acetonitrile (6). In another aspect of the invention, intermediate 5 may have a leaving group other than fluorine. Thus, compounds of the general formula:

The resulting methyl 2-(5-(4-(2-morpholinoethoxy)phenyl)pyridin-2-yl)acetate (7) and benzyl amine were coupled in anisole at high temperature to afford 2-(5-(4-(2-morpholinoethoxy)phenyl)pyridin-2-yl)-N-benzylacetamide (Compound 134). An HCl solution formed by adding acetyl chloride to absolute ethanol was added to Compound 134 to form the bis-HCl salt, 2-(5-(4-(2-morpholinoethoxy)phenyl)pyridin-2-yl)-N-benzylacetamide dihydrochloride, (KX2-di-HCl).

The synthesis of the mesylate salt of Compound 134 (Compound 134•MSA) is depicted in the scheme below:

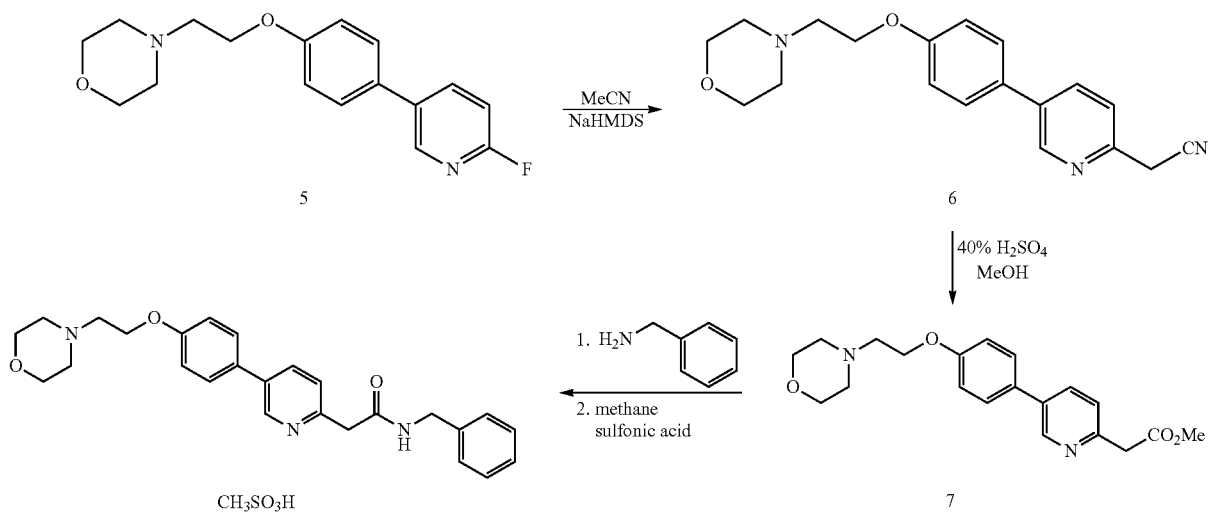

2-(5-(4-(2-morpholinoethoxy)phenyl)pyridin-2-yl)-N-benzylacetamide mesylate (Compound 134•MSA) was synthesized in four linear steps starting from compound 5. The first 3 steps were carried out similar to the procedure discussed above for Compound 134•2HCl to afford methyl 2-(5-(4-(2-morpholinoethoxy)phenyl)pyridin-2-yl)acetate (Compound 134). Compound 134 was converted to the methanesulfonate salt by treatment with methanesulfonic acid (MSA) in acetone at 50° C. to afford 2-(5-(4-(2-morpholinoethoxy)phenyl)pyridin-2-yl)-N-benzylacetamide mesylate (Compound 134•MSA).

In another aspect of the invention, intermediate 7 can be synthesized having a group other than —C(O)OMe. The skilled chemist would pursue intermediate compounds of the general formula:

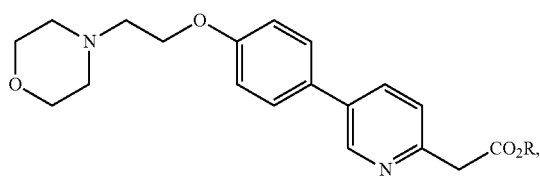

wherein the group "R" includes but is not limited to hydrogen and alkyl.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages described herein can be provided in single, divided, or continuous doses (which dose may be adjusted for the patient's weight in kg, body surface area in $m^2$, and age in years). Dosage can be provided in an effective amount of a pharmaceutical agent that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in pro-drug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject.

Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples, The provided examples illustrate different components and methodology useful in practicing the present invention. The examples do not limit the claimed invention. Based on the present disclosure the skilled artisan can identify and employ other components and methodology useful for practicing the present invention.

2. Methods of Treatment

The present invention provides a method of treating a cell proliferative disorder comprising administering to a subject in need thereof a compound of the present invention.

The present invention provides a method of treating a cell proliferative disorder comprising administering to a subject in need thereof, a therapeutically effective amount of a compound according to formula IB:

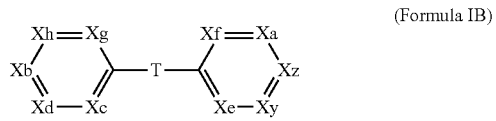

(Formula IB)

or a pharmaceutically acceptable salt, solvate, hydrate, or prodrug thereof, wherein:

T is a bond;

$X_y$ is CY, N, or N—O;

$X_z$ is CZ;

Y is selected from hydrogen, hydroxyl, halogen, lower ($C_1$, $C_2$, $C_3$, $C_4$, $C_5$, or $C_6$) alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, and O-benzyl;

$X_a$ is $CR_a$, N, or N—O;

$X_b$ is $CR_b$, N, or N—O;

$X_c$ is $CR_c$, N, or N—O;

$X_d$ is $CR_d$, N, or N—O;

$X_e$ is $CR_e$, N, or N—O;

$X_f$ is $CR_4$, N, or N—O;

$X_g$ is $CR_5$, N, or N—O;

$X_h$ is $CR_6$, N, or N—O;

$R_a$, $R_b$, $R_c$, $R_d$, $R_e$, $R_4$, $R_5$, and $R_6$ are, independently, hydrogen, hydroxyl, halogen, P, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

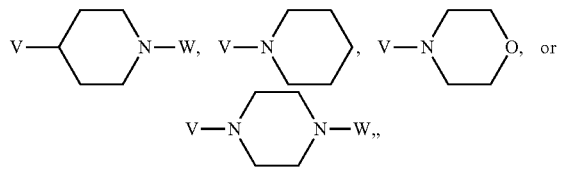

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;

P is $SO_3H$, $OSO_3H$, $PO_3H_2$, $OPO_3H_2$, $NH_2$, $NHR_{19}$, $NR_{20}R_{21}$,

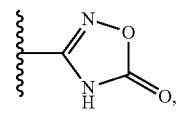

tetrazole, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower alkyl is linear or branched alkyl;

K is aryl, heteroaryl, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, tetrazole, or

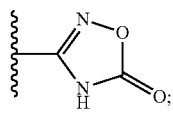

L is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

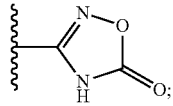 [SMILES: *c1noc(=O)[nH]1]

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

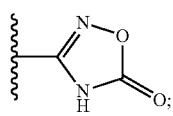 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

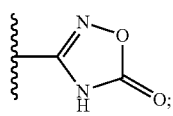 [SMILES: *c1noc(=O)[nH]1]

R$_{19}$, R$_{20}$ and R$_{21}$ are C$_1$, C$_2$, C$_3$, C$_4$, C$_5$, or C$_6$ alkyl or R$_{19}$ and R$_{20}$ taken together with the attached nitrogen atom form a five membered ring;

V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

Z is (CHR$_1$)$_n$—C(O)—NR$_2$(CHR$_3$)$_m$—Ar, where Ar is a substituted or unsubstituted aryl or nitrogen-containing heteroaryl group, R$_1$, R$_2$, and R$_3$ are independently H or C$_1$, C$_2$, C$_3$, C$_4$, C$_5$, or C$_6$ alkyl; and n and m are independently 0, 1, or 2, wherein the therapeutically effective amount is between about 50 mg to about 500 mg (or any integer within said range and wherein the compound is administered once per 24 hour period.

The present invention provides a method of preventing reoccurrence of a cell proliferative disorder in a subject previously diagnosed with a cell proliferative disorder comprising administering to the subject a therapeutically effective amount of a compound of the present invention.

The present invention provides a method of preventing reoccurrence of a cell proliferative disorder in a subject previously diagnosed with a cell proliferative disorder comprising administering to the subject a therapeutically effective amount of a compound according to formula IB:

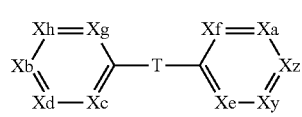

(Formula IB)

or a pharmaceutically acceptable salt, solvate, hydrate, or prodrug thereof, wherein:
T is a bond;
X$_y$ is CY, N, or N—O;
X$_z$ is CZ;
Y is selected from hydrogen, hydroxyl, halogen, lower (C$_1$, C$_2$, C$_3$, C$_4$, C$_5$, or C$_6$) alkyl, C$_1$, C$_2$, C$_3$, C$_4$, C$_5$, or C$_6$ alkoxy, O-lower (C$_1$, C$_2$, C$_3$, C$_4$, C$_5$, or C$_6$) alkyl-aryl, and O-benzyl;
X$_a$ is CR$_a$, N, or N—O;
X$_b$ is CR$_b$, N, or N—O;
X$_c$ is CR$_c$, N, or N—O;
X$_d$ is CR$_d$, N, or N—O;
X$_e$ is CR$_C$, N, or N—O;
X$_f$ is CR$_4$, N, or N—O;
X$_g$ is CR$_5$, N, or N—O;
X$_h$ is CR$_6$, N, or N—O;
R$_a$, R$_b$, R$_c$, R$_d$, R$_e$, R$_4$, R$_5$, and R$_6$ are, independently, hydrogen, hydroxyl, halogen, P, C$_1$, C$_2$, C$_3$, C$_4$, C$_5$, or C$_6$ alkyl, C$_1$, C$_2$, C$_3$, C$_4$, C$_5$, or C$_6$ alkoxy, O-lower (C$_1$, C$_2$, C$_3$, C$_4$, C$_5$, or C$_6$) alkyl-aryl, O-benzyl, C$_1$, C$_2$, C$_3$, C$_4$, C$_5$, or C$_6$ alkyl-OH, COOH, COO-lower (C$_1$, C$_2$, C$_3$, C$_4$, C$_5$, or C$_6$) alkyl, SO$_2$H, SO$_2$-lower (C$_1$, C$_2$, C$_3$, C$_4$, C$_5$, or C$_6$) alkyl,

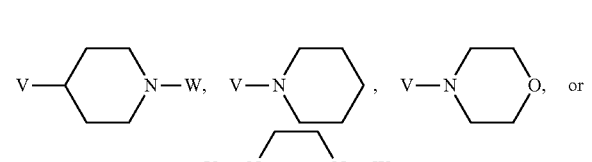

where W is H, or C$_1$, C$_2$, C$_3$, C$_4$, C$_5$, or C$_6$ alkyl, C$_1$, C$_2$, C$_3$, C$_4$, C$_5$, or C$_6$ alkyl-aryl;

P is SO$_3$H, OSO$_3$H, PO$_3$H$_2$, OPO$_3$H$_2$, NH$_2$, NHR$_{19}$, NR$_{20}$R$_{21}$,

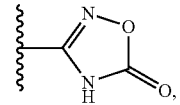

tetrazole, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q, further wherein lower alkyl is linear or branched alkyl;

K is aryl, heteroaryl, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

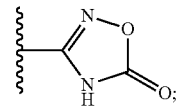 [SMILES: *c1noc(=O)[nH]1]

L is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

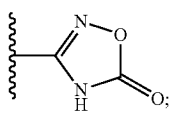 [SMILES: *c1noc(=O)[nH]1]

M is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

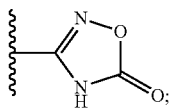 [SMILES: *c1noc(=O)[nH]1]

Q is aryl, heteroaryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, tetrazole, or

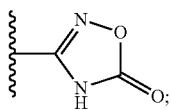

R$_{19}$, R$_{20}$ and R$_{21}$ are C$_1$, C$_2$, C$_3$, C$_4$, C$_5$, or C$_6$ alkyl or R$_{19}$ and R$_{20}$ taken together with the attached nitrogen atom form a five membered ring;

V is a bond, —CH$_2$—, —CH$_2$CH$_2$—, —CH$_2$CH$_2$CH$_2$—, —O—CH$_2$—, —OCH$_2$CH$_2$— or —OCH$_2$CH$_2$CH$_2$—;

Z is (CHR$_1$)$_n$—C(O)—NR$_2$(CHR$_3$)$_m$—Ar, where Ar is a substituted or unsubstituted aryl or nitrogen-containing heteroaryl group, R$_1$, R$_2$, and R$_3$ are independently H or C$_1$, C$_2$, C$_3$, C$_4$, C$_5$, or C$_6$ alkyl; and n and m are independently 0, 1, or 2.

Preferably, the compound is

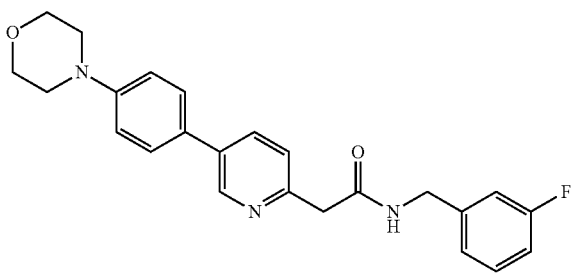 [SMILES: O=C(Cc1ccc(-c2ccc(N3CCOCC3)cc2)cn1)NCc1cccc(F)c1]

or a pharmaceutically acceptable salt, solvate, hydrate, or prodrug thereof.

The therapeutically effective amount can be between about 50 mg to about 500 mg (or any integer within said range (e.g., 50, 51, 52, 53 . . . )), between about 100 mg to about 400 mg, between about 200 mg to about 300 mg, about 250 mg or 250 mg.

The treatment, or the previous treatment, can produce immunological memory and/or produce in the subject. The treatment or previous treatment can produce memory B-cells and/or memory T-cells in the subject.

As used herein, "immune memory" or "immunological memory" refers to the ability of the immune system to respond more rapidly and effectively to pathogens such as tumor cells that have been encountered previously, and reflects the pre-existence of a clonally expanded population of antigen-specific lymphocytes. Memory responses, which may be call secondary, tertiary, and so on, depends on the number of exposures to antigen, also differ qualitatively from primary responses. "Immune memory" or "immunological memory" refers to when a subject develops a protective or defensive system against tumor cells after the subject has been treated with a pharmaceutical composition comprising a compound of the invention. "Immune memory" or "immunological memory" as used herein includes memory B cells and/or memory T cells activation and replication, where some of their offspring become long-lived memory cells. These memory cells may remember the specific cancer or proliferative disorder encountered and can mount a strong response if the cancer or proliferative disorder is detected again (Janeway, C. A. et al., *Immunobiology: The Immune System in Heath and Disease*, (Garland, 3$^{rd}$ ed. 1997)).

As used herein, "immune-competent" refers to subject whose immune system contains B and T cells. "Immune-compromised" refers to subject whose immune system lacks B and T cells. Preferably, the subject is immune-competent.

The subject can be previously treated for the cell proliferation disorder. Preferably, the subject was previously treated for the cell proliferation disorder with a compound of the invention. More preferably, the subject was previously treated for the cell proliferation disorder with the compound having the formula

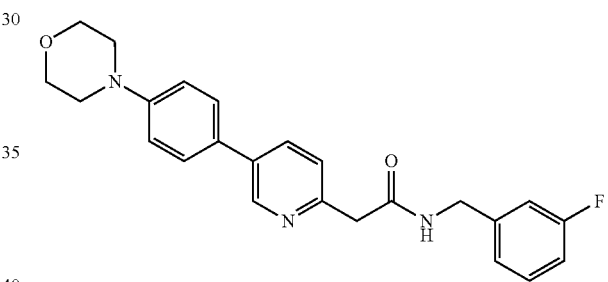

or a pharmaceutically acceptable salt, solvate, hydrate, or prodrug thereof.

The subject can be described to be in remission following treatment for the proliferation disorder. As used herein, "remission" refers to the state of absence of disease or disorder activity or absence of symptoms or signs of a disease or disorder in subject known to have the disease or disorder. A partial remission may be defined for cancer as reduction in tumor size by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater or greater reduction in the measurable parameters of tumor growth as may be found on physical examination, radiologic study, or by biomarker levels from a blood or urine test. Size of a tumor may be measured by any reproducible means of measurement. The size of a tumor may be measured as a diameter of the tumor. A complete remission is defined as complete disappearance of all such manifestations of disease. To be considered to be in remission a subject must not have reoccurrence of the disease or disorder within 30 days of the last treatment for said disease or disorder.

The cell proliferative disorder can be cancer or a precancerous condition. The present invention further provides the use of a compound of the present invention, or a pharmaceutically acceptable salt, prodrug, metabolite, polymorph, derivative, analog, or solvate thereof, for the preparation of a medicament useful for the treatment of a cell proliferative disorder.

The present invention also provides methods of protecting against a cell proliferative disorder in a subject in need thereof by administering a therapeutically effective amount of compound of the present invention, or a pharmaceutically acceptable salt, prodrug, metabolite, polymorph or solvate thereof, to a subject in need of such treatment. The cell proliferative disorder can be cancer or a precancerous condition. The present invention also provides the use of compound of the present invention, or a pharmaceutically acceptable salt, prodrug, metabolite, polymorph or solvate thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies.

A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

For example, the solid tumor (or tumors) is a glioblastoma, oligodendroglioma, astrocytoma or medulloblastoma. The solid tumor can be glioblastoma.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target kinase) but does not significantly modulate another molecular target (e.g., a non-target kinase). The invention also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be the to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target kinase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of the compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of the compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of the compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention, or a pharmaceutically acceptable salt, prodrug, metabolite, polymorph or solvate thereof, demonstrates a minimum of a four fold differential, preferably a ten fold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a kinase of interest.

The present invention provides methods to assess biological activity of a compound of the present invention, or a pharmaceutically acceptable salt, prodrug, metabolite, polymorph or solvate thereof. In one method, an assay based on enzymatic activity can be utilized. In one specific enzymatic activity assay, the enzymatic activity is from a kinase. As used herein, "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylates particular, protein/peptide substrates, they all bind the same second substrate ATP in a highly conserved pocket. About 50% of the known oncogene products are protein tyrosine kinases (PTKs), and their kinase activity has been shown to lead to cell transformation. Preferably, the kinase assayed is a tyrosine kinase.

A change in enzymatic activity caused by a compound of the present invention, or a pharmaceutically acceptable salt, prodrug, metabolite, polymorph or solvate thereof, can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules; and, plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, adaptor proteins such as Gab-1, Grb-2, Shc, SHP2 and c-Cbl, and signal transducers such as Ras, Src, PI3K, PLC-γ, STATs, ERK1 and 2 and FAK.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA.* 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SC10-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-$\beta$, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCID-469 (targets MAP/MEK), GW681323 (targets MAP/MEK), CC-401 (targets JNK), CEP-1347 (targets JNK), and PD 332991 (targets CDK).

Compound 76 is a synthetic, orally bioavailable, novel small molecule microtubule polymerization inhibitor with very high CNS penetration. Compound 76 is shown in Table 1. The efficacy of Compound 76 as a novel anti-cancer agent is tested directly using mouse model of malignant glioma. Compound 76 is an orally administered tubulin polymerization inhibitor that binds to a novel site on heterodimeric tubulin, and to a novel conformation of the dimer. Compound 76 can inhibit Src signaling in tumors. Compound 76 has been evaluated in various brain tumor cell lines. In all cases, Compound 76 inhibited proliferation with GI50's<55 nM. When administered orally to mice at a dose of 10 mg/kg, the ratio of drug levels in the brain compared to plasma levels was 0.76, indicating excellent BBB penetration as in Example 1.

Compound 76 was evaluated in various human and mouse brain tumor cells derived from glioblastoma multiforme, astrocytoma and medulloblastoma. Compound 76 potently inhibited the growth of these brain tumor cells. When administered to mice Compound 76 penetrated the brain by 76%, thereby successfully addressing the first major challenge in brain cancer drug discovery. Drugs which are used to treat brain tumors often penetrate only 20% or less. In mice with aggressive brain tumors Compound 76 not only very significantly slows the rate of tumor growth, but also up to 60% of the drug treated mice experience complete tumor regression and no reoccurrence within their normal full life span (about 2 years for mice). Temodar has also been evaluated in this mouse model for comparison, and it does not cause complete tumor regression, but rather only slows the growth rate of the tumors. In addition, it was observed that Compound 76 treated mice had much less brain edema than placebo or Temodar treated mice.

Compound 76 was also evaluated in the orthotropic GL261 glioma model in immune-competent, syngeneic C57BL/6 mice. Mice implanted intracerebrally with $1 \times 10^5$ GL261 cells treated with vehicle alone (saline) have a median survival time (MeST) of 21 days (range 18-28). Mice treated by oral Compound 76 (30 mg/kg, b.i.d.) have a MeST of 30.5 days ranging 23-32 days. In contrast, when Compound 76 is given orally at (30 mg/kg, s.i.d.) the MeST increases to over 120 days, with more than 60% of the treatment group still alive 12 months later (p<0.0001). Specimens from these mice also showed lymphocytic infiltration of the tumor site. Further experiments were performed using a SCID version of C57BL/6 mice (B6.CB17-Prkdc$^{scid}$/SzJ), a mouse model of B6 background, but is immune-compromised. In this SCID model, mice bearing GL261 intracerebral tumors and treated with vehicle alone had a similar survival as the immune-competent C57BL/6 counterpart, however mice treated with Compound 76 now only had a MeST of 40 days (range 29-75). SCID mice surviving greater than 45 days all proceeded to develop lethal GL261 gliomas (observed by MRI) shortly after drug was discontinued. C57BL/6 mice "cured" in the previous group (immune-competent) also subsequently rejected a second GL261 tumor implant challenge. Additional molecular studies show that Compound 76 increased expression and altered the localization of intracellular survivin, a molecule that can be targeted by immunotherapy.

The results of five independent studies indicate that Compound 76 slows the growth rate of intracerebral GL261 glioma relative to control groups. When given as a single dose per day (s.i.d.) Compound 76 led to complete tumor regression in up to 60% of treated mice without further progression. The subsequent rejection of a second tumor in these mice is indicative of immune memory. This magnitude of anti-tumor effect was not observed in SCID models leading to the possibility that Compound 76 may be involved in an anti-tumor immune response.

Compound 76 slows the growth rate of intracerebral GL261 glioma relative to control groups. When given single dose per day (s.i.d.) Compound 76 led to complete tumor regression in up to 60% of treated mice without further progression. Long term survivor C57BL/6 mice subsequently rejected a second GL261 tumor implant challenge, consistent with generation of productive immune memory. This magnitude of anti-tumor effect was not observed in the immuno-compromised mice, suggesting that the once daily dosing regimen with Compound 76 permits the generation of an effective immune response that contributes to long-term cures.

3. Examples

Example 1

Penetration into Brain Tissue

Compound 76 displays penetration into brain tissue, as is reported in Table 4.

TABLE 4

Brain and Plasma Pharmacokinetic Parameters of Compound 76 in Male CD-1 Mice after a Single Oral Dose of 10 mg/kg

| Sample ID | Tmax (hr) | Cmax (ng/mL) | AUClast (ng · hr/mL) |
|---|---|---|---|
| Brain | 1.00 | 279 | 656 |
| Plasma | 1.00 | 426 | 863 |

Brain Cmax and AUClast are ng/g and ng·hr/g, respectively. Compound 76 has 76% brain penetration from plasma In order to determine the ability of Compound 76 to penetrate into brain tissue, mice received a single oral dose of 10 mg/kg. The concentration of Compound 76 was measured in plasma and in brain tissue homogenates. This analysis indicates that 76% of the drug that gets into plasma, partitions into brain tissue.

Example 2

Cell Growth Inhibition

The drug concentration required to block net cell growth by 50% relative to a control sample is measured as the $GI_{50}$. The $GI_{50}$s for several of the compounds of the invention were assayed as described herein.

The HT29 cell line is a NCI standard human colon carcinoma cell line. HT-29 cells were obtained from ATCC at passage 125 and were used for inhibition studies between passage 126-151. HT29 cells were routinely cultured in McCoy's 5A medium supplemented with Fetal Bovine Serum (1.5% v/v) and L-glutamine (2 mM).

The c-Src 3T3 is a mouse fibroblast NIH 3T3 normal cell line that has been transfected with a point-mutant of human c-Src wherein tyrosine 527 has been converted to a phenylalanine. This mutation results in "constitutively active" c-Src because phosphorylation on tyrosine 527 results in auto-inhibition of Src by having it fold back on its own SH2 domain. With a Phe there, this phosphorylation can't occur and therefore auto-inhibition can't occur. Thus, the always fully active mutant Src then converts the normal mouse fibroblasts into rapidly growing tumor cells. Since the hyperactive Src is the main factor driving growth in these cells (particularly when cultured under low growth serum conditions), compounds active in blocking this growth are thought to work by blocking Src signaling (e.g. as a direct Src kinase inhibitor or as an inhibitor acting somewhere else in the Src signaling cascade). The cells were routinely cultured in DMEM supplemented with Fetal Bovine Serum (2.0% v/V), L-glutamine (2 mM) and Sodium Pyruvate (1 mM).

In the BrdU Assay for cell growth inhibition, quantitation of cell proliferation was based on the measurement of BrdU incorporation during DNA synthesis. The Cell Proliferation ELISA BrdU assay kit (colorimetric) was obtained from Roche Applied Science and performed as per vendor instructions.

Growth inhibition was expressed as a $GI_{50}$ where the $GI_{50}$ is the sample dose that inhibits 50% of cell growth. The growth inhibition (GI) is determined from the formula GI= $(T_0-T_n\times100/T_0-CON_n)$ where $T_0$ is the BrdU growth of untreated cells at time "0", $T_n$ is the BrdU growth of treated cells at day "n" and $CON_n$ is the control BrdU growth of control cells at day "n". The $GI_{50}$ was extrapolated and the data plotted using XL-Fit 4.0 software.

Actively growing cultures were trypsinized and cells were resuspended in 190ℓ of appropriate culture medium supplemented with 1.05% FBS in each well of a 96-well culture plate (1000 HT-29 cells; 2500 c-Src 3T3 cells). For 96 well culture plate experiments, c-Src 3T3 medium was supplemented with 10 mM HEPES buffer. HT-29 cells were seeded in standard tissue culture 96-well plates and c-Src 3T3 cells were seeded in 96-well plates coated with Poly-D-lysine (BIOCOAT™). To increase $CO_2$ diffusion, c-Src 3T3 96-well plates were incubated with their lids raised by ~2 mm using sterile rubber caps.

Seeded 96 well plates were allowed to attach overnight for 18-24 hours, either at 37° C. and 5% $CO_2$ for HT-29 or at 37° C. and 10% $CO_2$ for c-Src 3T3. Approx 18-24 hours after seeding, the initial growth of cells ($T_0$) was determined for untreated cells using the BrdU assay. Samples were reconstituted in DMSO at 20 mM and intermediate dilutions made using DMEM containing 10% FBS. The final assay concentrations were 1.5% for FBS and 0.05% for DMSO. Samples were added as 10 μL aliquots in triplicate and plates were incubated as above for ~72 hours. Negative (vehicle) and positive controls (e.g., AZ (KX2-328)) were included. Plates were assayed for BrdU and the data analyzed as above for $GI_{50}$.

The results are shown in Table 5. In this table, the data is listed as Growth % of Control, such that a lower number at an indicated concentration indicates a greater potency of the compound in blocking growth of that tumor cell line. All compounds were initially prepared as 20 mM DMSO stock solutions and then diluted into buffer for the in vitro tumor growth assays. NG means no cell growth beyond the control and T means the number of cells in the drug treated wells was less than in the control (i.e. net cell loss). NT indicates that the test was not performed. Compound AZ (KX2-328) is an ATP-competitive tyrosine kinase inhibitor, as described in Plé et al., J. Med. Chem., 47:871-887 (2004).

As shown in Table 5, $GI_{50}$s were obtained for a number of the compounds in other cell lines. These GI50's were determined using the standard tumor growth inhibition assays, similar to that described in detail for the HT29 cell line above, and the following cell lines: colon tumor cell lines KM12, lung cancer cell line H460 and lung cancer cell line A549 (all are NCI standard tumor cell lines).

TABLE 5

| | HT-29 Growth, % of Control Mean, n = 3 | | | | c-Src 3T3 Growth, % of Control Mean, n = 3 | | |
|---|---|---|---|---|---|---|---|
| CMPD | 5 uM | 500 nM | 50 nM | $GI_{50}$ | 10 uM | 1.0 uM | 100 nM |
| AZ | T | 10.0 | 73.0 | 99 nM (c-Src 3T3), 794 nM (HT29) | T | T | 13.0 |
| 1 | T | T | 83.1 | 53 nM (c-Src 3T3), 484 nM (HT29) 105 nM (KM12) 280 nM (H460) 330 nM (A549) | T | T | 46.3 |
| 2 | T | T | 107.7 | 349 nM (c-Src 3T3), 877 nM (HT29), 410 nM (KM12) 890 nM (H460) 1.03 uM (A549) | T | T | 35.0 |
| 4 | 39.4 | 93.8 | 85.9 | | 4.2 | 45.3 | 65.7 |
| 5 | 32.3 | 76.1 | 87.9 | | 67.1 | 77.7 | 94.5 |
| 9 | 33.7 | 67.6 | 93.7 | | 12.1 | 94.5 | 98.5 |
| 3 | T | T | 124.4 | | T | T | 47.0 |
| 10 | T | T | 80.2 | | T | T | 91.6 |
| 16 | T | T | 101.2 | | T | T | 88.2 |
| 6 | T | T | 29.5 | | T | T | T |
| 7 | T | T | 93.3 | | T | T | 101.8 |
| 8 | T | T | 60.4 | | T | T | 81.3 |
| 24 | T | T | 31.6 | >200 nM (c-Src 3T3), 680 nM (HT29) | T | T | 81.3 |
| 13 | T | 45.1 | 77.8 | >200 nM (c-Src 3T3) | T | T | 88.2 |
| 12 | T | 50.3 | 66.0 | | T | 88.1 | 89.3 |
| 11 | 14.4 | 83.7 | 53.21 | | 39.3 | 88.4 | 93.6 |
| 14 | T | 64.0 | 83.5 | | T | 85.6 | 94.2 |
| 15 | T | 93.2 | 164.7 | | T | 71.0 | 91.4 |
| 17 | 86.2 | 132.0 | 111.2 | | 73.1 | 86.5 | 90.4 |
| 18 | 23.7 | 118.1 | 127.2 | | 55.8 | 96.2 | 95.5 |
| 19 | T | 87.2 | 114.1 | 3,730 nM (Src 3T3) | T | T | 94.6 |
| 20 | 60.8 | 106.9 | 105.6 | | 93.2 | 97.3 | 96.6 |
| 21 | NG | 95.7 | 91.0 | | T | 90.0 | 96.0 |
| 22 | T | T | 85.0 | 207 nM (c-Src 3T3), 215 nM (HT29) | T | 54.2 | 97.6 |
| 23 | 43.7 | 73.2 | 65.4 | | 55.7 | 87.3 | 92.2 |
| 25 | T | T | 101 | 269 nM (c-Src 3T3), 338 nM (HT29) | T | T | 96.0 |
| 26 | NT | NT | NT | | 9.0 | 95.4 | 101.3 |
| 27 | NT | NT | NT | | 82.7 | 91.4 | 92.2 |
| 28 | T | T | T | 34 nM (c-Src 3T3), 45 nM (HT29) | T | T | T |
| 54 | T | T | 91 | | T | T | 106.0 |
| 76 | T | T | T | 11 nM (c-Src 3T3), 10 nM (HT29) | T | T | T |
| 78 | T | T | 86 | 56 nM (c-Src 3T3), 56 nM (HT29) | T | T | 101 |
| 79 | T | 67 | 92 | | 100 | 70 | 92 |
| 82 | T | 80 | 105 | | T | 81 | 92 |
| 40 | T | T | 88 | 133 nM (c-Src 3T3), 93 nM (HT29) | T | T | 88 |
| 75 | T | 54 | 89 | | T | 83 | 103 |
| 41 | T | 6 | 64 | | T | T | 102 |
| 29 | T | 70 | 107 | | 27 | 101 | 99 |
| 55 | T | 72 | 87 | | T | 101 | 100 |
| 77 | 81 | 93 | 112 | | 106 | 105 | 104 |
| 81 | 16 | 33 | 98 | | 16 | 72 | 75 |
| 80 | T | T | T | 58 nM (c-Src 3T3); 67nM (HT-29) | T | T | T |
| 72 | T | T | 64 | 96 nM (c-Src 3T3); 639 nM (HT-29) | T | T | 97 |
| 115 | T | 57 | 74 | | T | 84 | 110 |
| 36 | T | T | 99 | 206 nM (c-Src 3T3); 354 nM (HT-29) | T | T | T |
| 74 | T | 93 | 96 | >1,600 nM (c-Src 3T3); >400 nM (HT-29) | T | T | T |
| 38 | T | T | T | 118 nM (c-Src 3T3); 111 nM (HT-29) | T | T | T |
| 31 | T | 61 | 88 | | 48 | 107 | 122 |
| 70 | T | 88 | 89 | | T | 104 | 106 |

TABLE 5-continued

| | HT-29 Growth, % of Control Mean, n = 3 | | | | c-Src 3T3 Growth, % of Control Mean, n = 3 | | |
|---|---|---|---|---|---|---|---|
| CMPD | 5 uM | 500 nM | 50 nM | GI$_{50}$ | 10 uM | 1.0 uM | 100 nM |
| 30 | T | 50 | 100 | | T | 119 | 124 |
| 33 | T | T | 58 | 914 nM (c-Src 3T3); 375 nM (HT-29) | T | T | 116 |
| 68 | 50 | 97 | 80 | | 103 | 114 | 117 |
| 116 | | | | 327 nM (c-Src 3T3); 248 nM (HT-29) | | | |
| 64 | | | | 1,430 nM (c-Src 3T3); inactive (HT-29) | | | |
| 83 | | | | 232 nM (c-Src 3T3) | | | |
| 37 | | | | 897 nM (c-Src 3T3); inactive (HT-29) | | | |
| 38 | | | | inactive (c-Src 3T3); 1,860 nM (HT-29) | | | |
| 66 | | | | >1,600 nM (c-Src 3T3); 906 nM (HT-29) | | | |
| 60 | | | | Inactive (c-Src 3T3); inactive (HT-29) | | | |
| 135 | | | | inactive (c-Src 3T3); inactive (HT-29) | | | |
| 114 | | | | 797 nM (c-Src 3T3); 868 nM (HT-29) | | | |
| 134 | | | | 13 nM (c-Src 3T3); 23 nM (HT-29) | | | |
| 133 | | | | 13 nM (c-Src 3T3); 21 nM (HT-29) | | | |
| 136 | | | | 24 nM (c-Src 3T3); 52 nM (HT-29) | | | |
| 137 | | | | 13 nM (c-Src 3T3); 26 nM (HT-29) | | | |

NG = No growth, total growth inhibition;
T = Cytotoxic Effect on Cells, negative growth;
NT = Not tested Table 6 shows Compound 134 and Compound 76 inhibition in brain tumor cell lines. These GI50s were determined using standard tumor growth inhibition assays.

TABLE 6

GI50 of Compound 76, Compound 134 and Dasatinib in brain tumor cell lines:

| Cell Line | Compound 76 IC50 | Compound 134 IC50 | Dasatinib IC50 | Organism | Disease | Morphology | Tumorigenic |
|---|---|---|---|---|---|---|---|
| Daoy | 54.9 nM | 13.6 nM | 2927 nM | Human | Desmoplastic cerebellar medulloblastoma | Polygonal | Yes |
| SK-N-MC | 0.13 nM | 5.8 nM | 5114 nM | Human | Neuroepithelioma | Epithelial | Yes |
| SW1088 | 22.1 nM | 76.1 nM | 897.3 nM | Human | Astrocytoma | Fibroblast | Yes |
| LN-18 | 2.9 nM | 14.5 nM | 565.3 nM | Human | Glioblastoma; glioma | Epithelial | Yes |
| SK-N-FI | 0.46 nM | 1.7 nM | 12.6 nM | Human | Neuroblastoma | Epithelial | Yes |
| U87 | 9.7 nM | 33.1 nM | 1586 nM | Human | Glioblastoma; astrocytoma | Epithelial | Yes |
| GL261 | 8.8 nM | 13.7 nM | 17.7 nM | Mouse | Glioblastoma | Epithelial | Yes |

Example 3

Plasma and Brain Exposure

The compounds of the invention demonstrate good plasma/brain exposure. For example, the plasma and brain exposure of Compound 134 (also referred to as Compound 134 and compound 134) and compound 76 (also referred to as Compound 76) are described below. Plasma concentrations were measured in mice after oral administration. All doses were formulated in purified water. Four groups of male CD-1 mice were dosed after an overnight fast and fed 4 hours post-dose. Dosing was as follows:

| Group Number | Route | Compound | Dose (mg/kg)* | Dose Vol. (mL/kg) |
|---|---|---|---|---|
| 1 | PO | Compound 134 Mesylate | 10 | 10 |
| 2 | PO | Compound 134 Mesylate | 50 | 10 |
| 3 | PO | Compound 76 2HCl | 10 | 10 |
| 4 | PO | Compound 76 2HCl | 50 | 10 |

*Note:
Doses administered were mg free base/kg

Protein was precipitated with 0.25 mL acetonitrile for plasma, 0.25 mL for brain. After centrifugation, supernatant was directly injected into an LC/MS system. The limit of quantitation was 1 ng/mL using a 50 μL aliquot for plasma and a 50 μL aliquot for brain. The standard curve was 1 to 1,000 ng/mL for both plasma and brain.

HPLC conditions were as follows:

HPLC System: Shimadzu SCL-10 System
Analytical Column: Aquasil C18 5 μm 100×2 mm column.
Column Temperature: Ambient temperature
Autosampler Temperature: Ambient temperature
Mobile Phase
   A) 10 mM Ammonium formate in water (pH 4).
   B) Acetonitrile.
Flow Rate: 0.6 mL/min
Injection Volume: 2 μL
Gradient:

| Time (Minute) | | | | | | | | | |
|---|---|---|---|---|---|---|---|---|---|
| 0.0 | 1.6 | 2.6 | 3.8 | 3.9 | 4.1 | 4.4 | 4.6 | 4.65 | 7.0 |
| % B | | | | | | | | | |
| 20 | 20 | 65 | 65 | 20 | 20 | 95 | 95 | 20 | Stop |

Mass Spectrometry Conditions were as follows:
   Instrument: ABI Sciex API 4000
Mode: ESI+
Experiment: MRM (multiple reaction monitoring)
Transitions:
   Compound 134: m/z 432.4→114.2 (Rt=3.11 minute)
   Compound 76: m/z 406.1→253.2 (Rt=3.33 minute)
   Tables 7-10 below show plasma and brain concentrations following the administration of a single oral dose of Compound 76 at 10 mg/kg and 50 mg/kg.

TABLE 7

Compound 76 Plasma Concentrations (ng/mL) in Male CD-1 Mice After a Single PO Dose of 10 mg/kg (Group 3)

| Time (hr) | Group A | Group B | Group C | Mean | SD | % CV |
|---|---|---|---|---|---|---|
| 0 | BLQ | BLQ | BLQ | 0.00 | 0.00 | NA |
| 0.5 | 65.93 | 217.56 | 159.53 | 147.67 | 76.51 | 51.81 |
| 1 | 284.09 | 596.31 | 398.35 | 426.25 | 157.97 | 37.06 |
| 2 | 153.07 | 118.96 | 342.45 | 204.83 | 120.40 | 58.78 |
| 5 | 2.63 | 64.15 | 53.18 | 39.99 | 32.81 | 82.05 |

NA: Not Applicable.
BLQ: Below Limit of Quantitation (1 ng/mL)
BLQ = 0 when calculating mean, SD and % CV

TABLE 8

Compound 76 Brain Concentrations (ng/g) in Male CD-1 Mice After a Single PO Dose of 10 mg/kg (Group 3)

| Time (hr) | Group A | Group B | Group C | Mean | SD | % CV |
|---|---|---|---|---|---|---|
| 0 | BLQ | BLQ | BLQ | 0.00 | 0.00 | NA |
| 0.5 | 43.98 | 138.55 | 116.84 | 99.79 | 49.54 | 49.64 |
| 1 | 227.97 | 334.71 | 273.32 | 278.67 | 53.57 | 19.22 |
| 2 | 109.78 | 78.76 | 336.07 | 174.87 | 140.46 | 80.32 |
| 5 | BLQ | 47.45 | 47.85 | 31.77 | 27.51 | 86.59 |

TABLE 9

Compound 76 Plasma Concentrations (ng/mL) in Male CD-1 Mice After a Single PO Dose of 50 mg/kg (Group 4)

| Time (hr) | Group A | Group B | Group C | Mean | SD | % CV |
|---|---|---|---|---|---|---|
| 0 | BLQ | BLQ | BLQ | 0.00 | 0.00 | NA |
| 0.5 | 1488.55 | 2316.91 | 1587.18 | 1797.54 | 452.48 | 25.17 |
| 1 | 1805.19 | 969.48 | 3635.91 | 2136.86 | 1363.81 | 63.82 |
| 2 | 475.13 | 1710.13 | 1709.02 | 1298.09 | 712.70 | 54.90 |
| 5 | 138.53 | 252.81 | 298.99 | 230.11 | 82.60 | 35.90 |

TABLE 10

Compound 76 Brain Concentrations (ng/g) in Male CD-1 Mice After a Single PO Dose of 50 mg/kg (Group 4)

| Time (hr) | Group A | Group B | Group C | Mean | SD | % CV |
|---|---|---|---|---|---|---|
| 0 | BLQ | BLQ | BLQ | 0.00 | 0.00 | NA |
| 0.5 | 960.08 | 2124.87 | 1051.16 | 1378.70 | 647.80 | 46.99 |
| 1 | 850.96 | 1888.05 | 548.55 | 1095.85 | 702.53 | 64.11 |
| 2 | 413.89 | 985.90 | 874.17 | 757.99 | 303.19 | 40.00 |
| 5 | 121.56 | 260.41 | 238.66 | 206.88 | 74.68 | 36.10 |

The brain and plasma pharmacokinetic parameters of Compound 76 in mice after a single dose of 10 mg/kg (Group 3) are as follows:

| Sample ID | $T_{max}$ (hr) | $C_{max}$ (ng/mL) | AUClast (ng · hr/mL) |
|---|---|---|---|
| Brain | 1.00 | 279 | 656 |
| Plasma | 1.00 | 426 | 863 |

Note:
Brain Cmax and AUClast are ng/g and ng · hr/g, respectively.

The AUClast Brain/AUClast Plasma Ratio is 0.76.

The brain and plasma pharmacokinetic parameters of Compound 76 in mice after a single dose of 50 mg/kg (Group 4) are as follows:

| Sample ID | $T_{max}$ (hr) | $C_{max}$ (ng/mL) | AUClast (ng · hr/mL) |
|---|---|---|---|
| Brain | 0.50 | 1379 | 3338 |
| Plasma | 1.00 | 2137 | 5443 |

Note:
Brain Cmax and AUClast are ng/g and ng · hr/g, respectively.

The AUClast Brain/AUClast Plasma Ratio is 0.61.

Example 4

Glioma Survival Studies

A brain tumor mouse xenograft study was conducted comparing Compound 76 and Compound 134 (Compound 134) to Temodar®. The studies were conducted in C57BL/6 mice. GL261 glioma cells (1×10⁵ in 5 μl DMEM) were implanted intracranial coordinates: bregma, lateral 2.0 mm, anterior 1.2 mm, 3.0 mm depth dura. Treatment was initiated 3 days post implantation. The groups were as follows (all doses in 100 ml $H_2O$):
Vehicle ($H_2O$)
Compound 134 2.5 mg/kg bid oral
Compound 134 5 mg/kg bid oral Compound 76 15 mg/kg bid oral
Compound 76 30 mg/kg bid oral
Temodar® 5 mg/kg once weekly oral Table 11 below shows a summary of the results. The median survival range and the log-rank (Mantel-Cox) statistical test results comparing the survival distributions of the samples. Compound 76 exhibited the best results when administered orally at 15 mg/kg/dose bid 7 hours apart.

TABLE 11

|  | Vehicle | Compound 134 2.5 mg/kg bid oral | Compound 134 5 mg/kg bid oral | Compound 76 15 mg/kg bid oral | Compound 76 30 mg/kg bid oral | Temodar® 5 mg/kg weekly × 1 oral |
|---|---|---|---|---|---|---|
| Median survival Range: | 22 21-25 | 25 22-36 | 23 22-29 | 30.5 25-34 | 29 23-32 | 29 26-29 |
| Log-Rank (Mantel-Cox) Test | | | | | | |
| vs. Vehicle |  | P = 0.1062 | P = 0.1762 | P = 0.0106 | P = 0.0425 | P = 0.0017 |
| vs. Temodar | P = 0.0017 | P = 0.3649 | P = 0.1366 | P = 0.2396 | P = 0.5237 |  |
| vs. Compound 134 2.5 mg/kg |  |  |  | P = 0.7559 | P = 0.6530 | P = 0.8901 |
| vs. Compound 134 5 mg/kg |  |  |  | P = 0.0605 | P = 0.1166 | P = 0.1366 |

Figure 3:
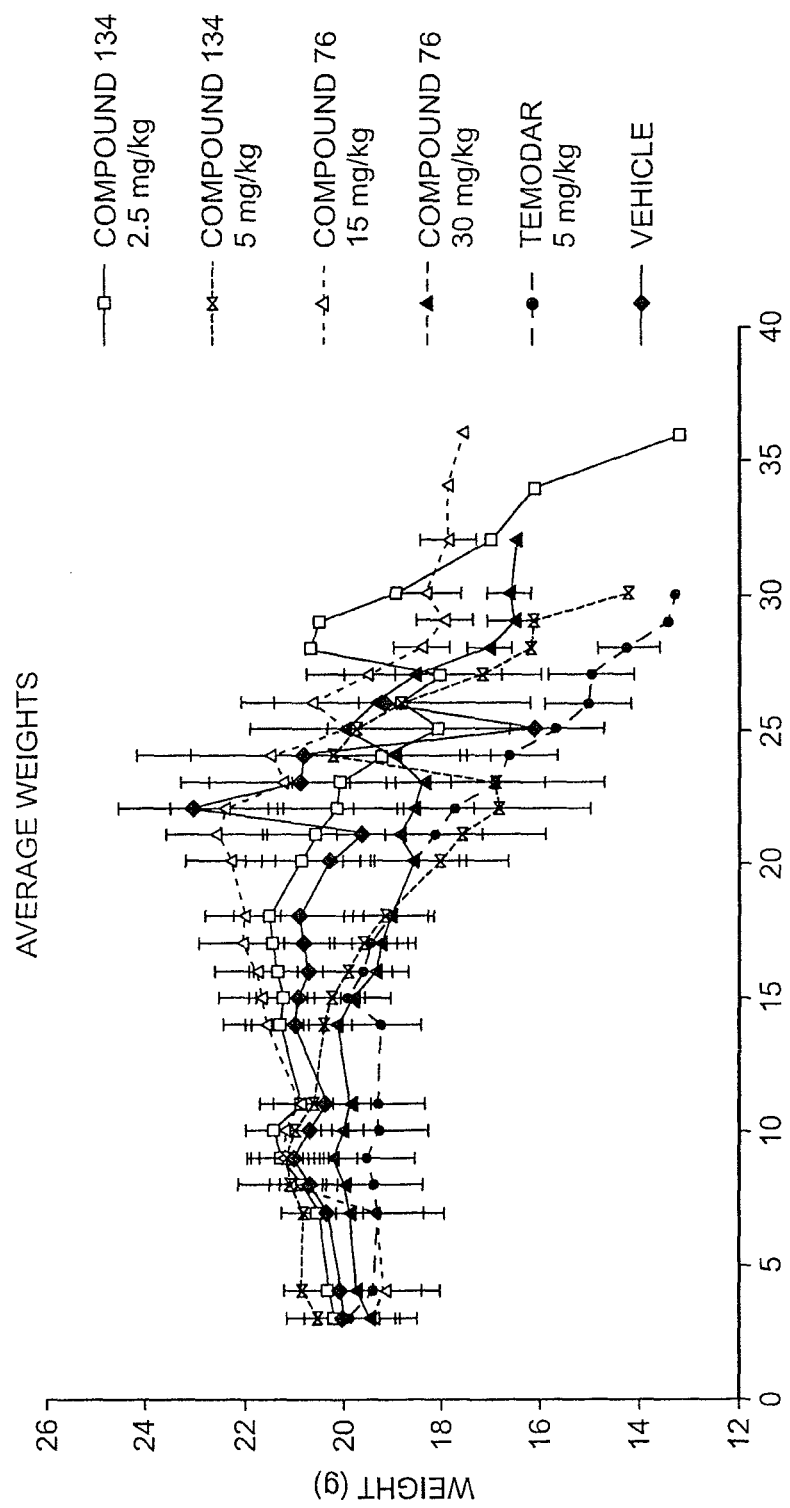
FIG. 3 is a graph showing the average weights over a 40-day period for each of the treatment groups in the intracranial GL261 glioma survival study.
Figure 4A:
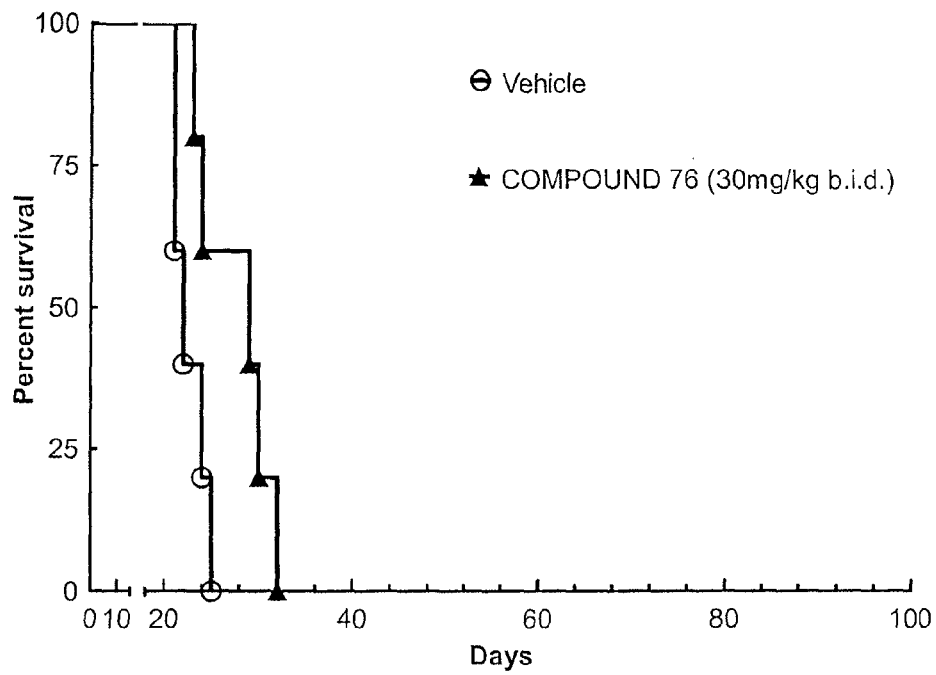
FIGS. 4A-C are a series of graphs showing the survival of C57BL6 mice with intracerebral GL261 glioma implants. Mice received intracerebral implants of 1×10$^5$ GL261 cells by stereotactic injection at 2 mm lateral, 1 mm anterior to bregma at 3 mm depth. After 4 days mice began indicated regimen of oral Compound 76. Panel (A) shows oral Compound 76 (30 mg/kg s.i.d.) began 4 days after tumor cell implantation and were repeated twice daily. Compound 76 extended median survival from 21 to 29 days (range). n=10. Panel (B) shows oral Compound 76 (30 mg/kg s.i.d.) began 4 days after tumor cell implantation and were repeated once daily. Compound 76 extended median survival >100 days (range), with up to 60% of drug treated mice experiencing complete tumor regression, n=10. Long term survivors were confirmed tumor free by high field MRI in FIG. 6. Panel (C) shows oral Compound 76 (30 mg/kg s.i.d.) began 4 days after tumor cell implantation into B6.CB17-Prkdc$^{scid}$/SzJ mice (C57BL/6-SCID verion) and were repeated once daily. Compound 76 extended median survival from 21-29 days (range), however there were no long term survivors, n=10. See high field MRI in FIG. 6
Figure 4B:
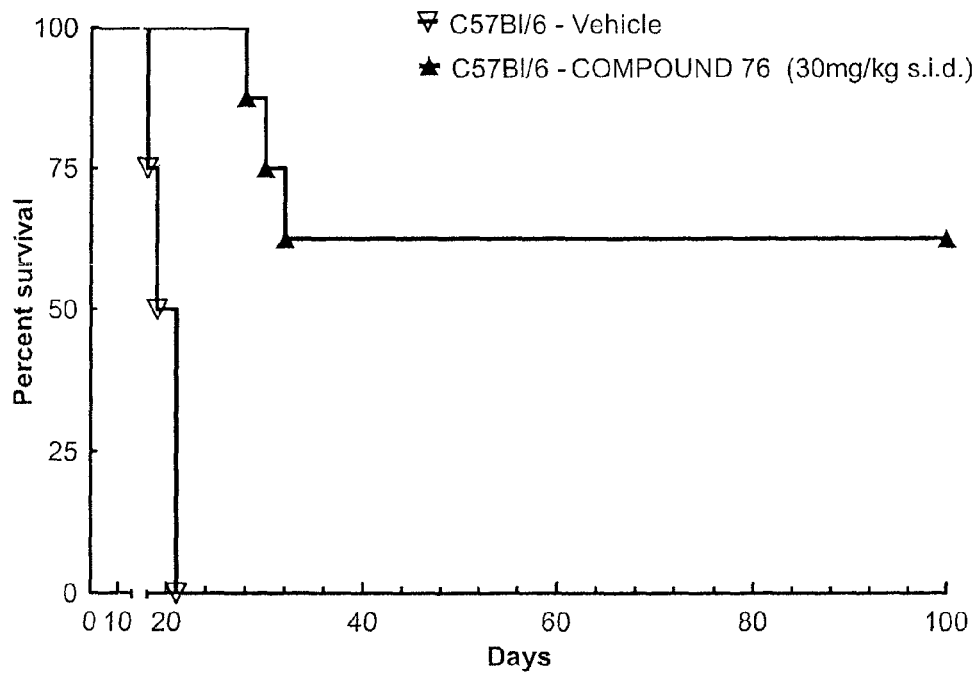
Figure 4C:
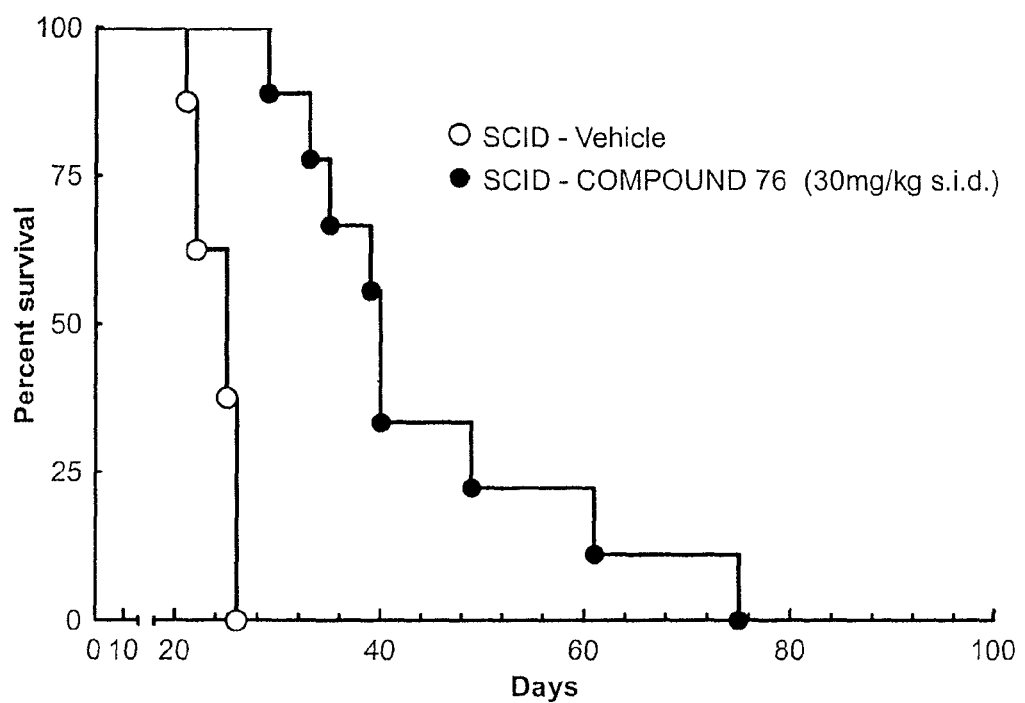
Figure 5:
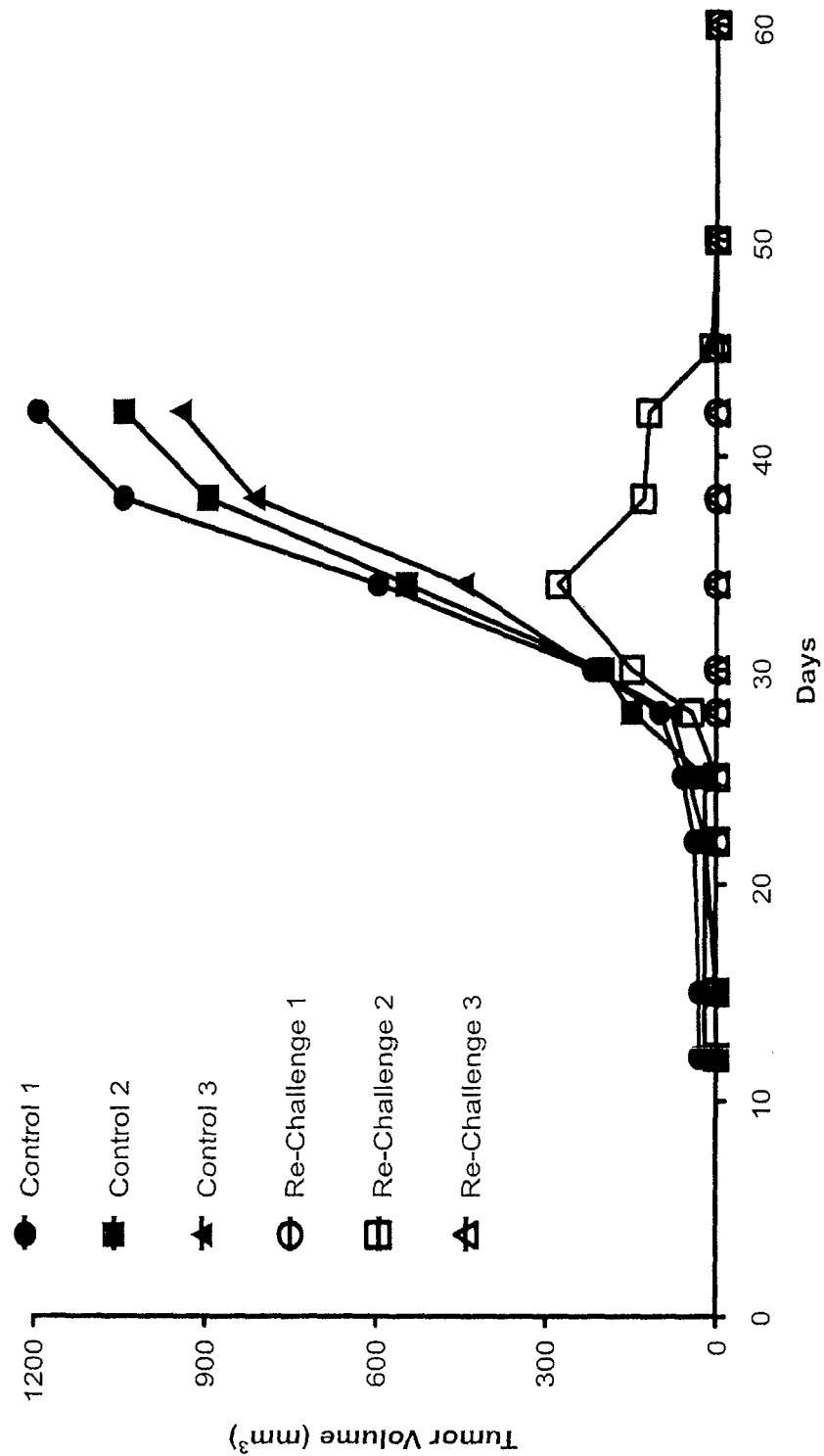
FIG. 5 is a graph of re-challenge of Compound 76 treated long term survivor mice from FIG. 4B with 1×10$^6$ s.c. GL261 glioa cells. Age and litter matched controls were implanted. Long term survivor C57BL/6 mice subsequently rejected the second GL261 tumor challenge.
Figure 6A:
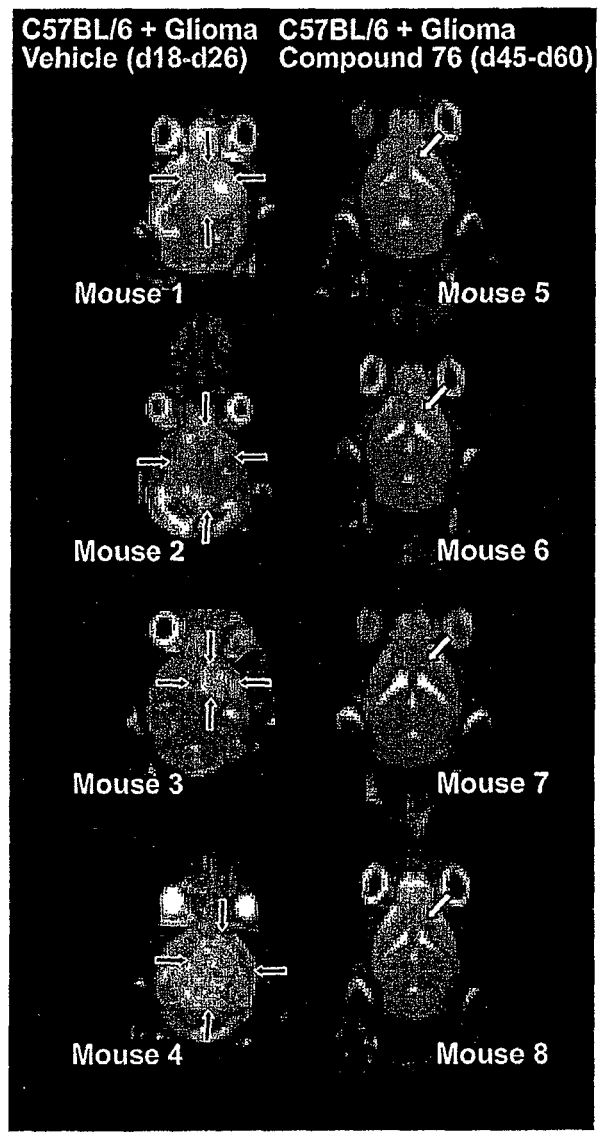
FIGS. 6A-B are representative MRI images (T2-weighted spin echo) of GL261 implanted, Compound 76 treated mice (30 mg/kg s.i.d.). Panel (A) shows arrows on mice 1-4 indicate tumor boundaries in C57BL/6 vehicle mice; arrows on mice 5-8 indicate the site of tumor cell injection in Compound 76 treated C57BL/6 mice, no residual tumor is observed. Panel (B) shows arrows on tumor forming d25 and tumor d32 indicate tumor reoccurrence in Compound 76 treated B6.CB17-Prkdc$^{scid}$/SzJ mice
Figure 6B:
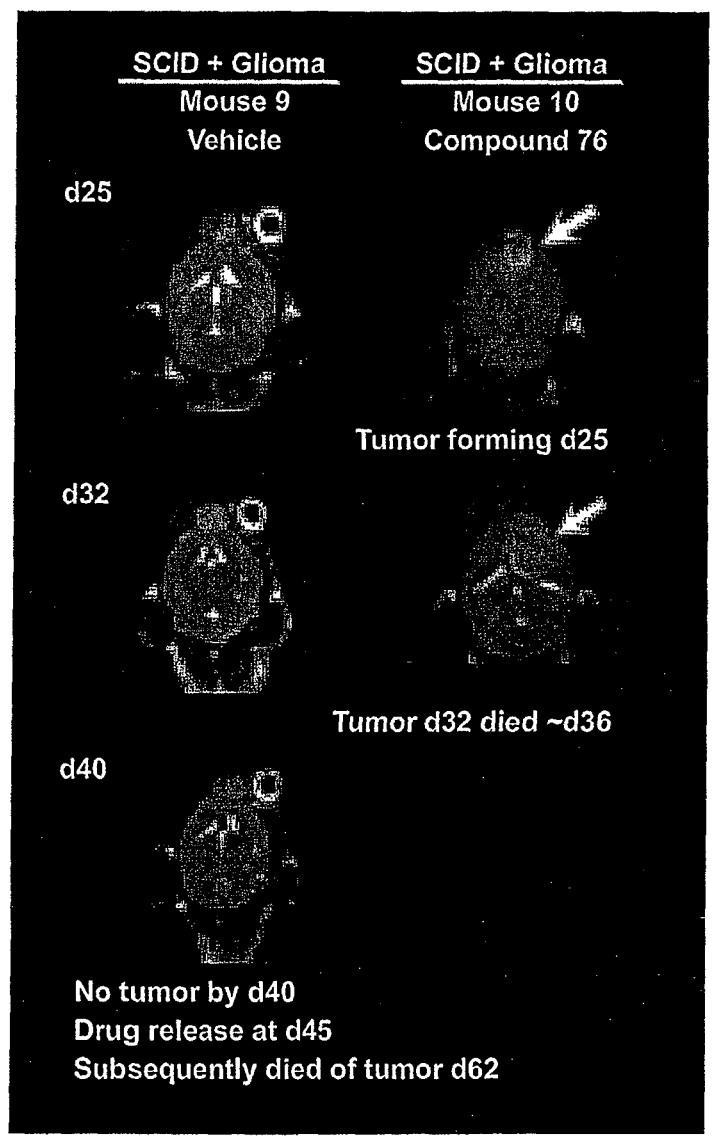

FIGS. 2A-F show the weight gain in each of the C57BL/6 mice in the different treatment groups. The average weight at endpoint for each of the treatment groups is shown below in Table 12. FIG. 3 is a graph showing the average weights over a 40-day period for each of the treatment groups.

TABLE 12

| Average weight at endpoint | | |
|---|---|---|
| Vehicle = |  | 19.2 g |
| Compound 76 | 15 mg/kg = | 16.9 g |
| Compound 76 | 30 mg/kg = | 15.0 g |
| Compound 134 | 2.5 mg/kg = | 16.0 g |
| Compound 134 | 5 mg/kg = | 14.3 g |
| Temodar® | 5 mg/kg = | 13.3 g |

Example 5

Evaluation in Orthotropic GL261 Glioma Model

Compound 76 was evaluated in the orthotropic GL261 glioma model in immune-competent, syngeneic C57BL/6 mice. Compound 76 is shown in Table 1. Mice implanted intracerebrally with $1\times10^5$ GL261 cells treated with vehicle alone (saline) have a median survival time (MeST) of 21 days (range 18-28). Mice treated by oral Compound 76 (30 mg/kg, b.i.d.) have a MeST of 30.5 days ranging 23-32 days. In contrast, when Compound 76 is given orally at (30 mg/kg, s.i.d.) the MeST increases to over 120 days, with more than 60% of the treatment group still alive 12 months later (p<0.0001). Specimens from these mice also showed lymphocytic infiltration of the tumor site. Further experiments were performed using a SCID version of C57BL/6 mice (B6.CB17-Prkdc$^{scid}$/SzJ), a mouse model of B6 background, but is immune-compromised. In this SCID model, mice bearing GL261 intracerebral tumors and treated with vehicle alone had a similar survival as the immune-competent C57BL/6 counterpart, however mice treated with Compound 76 now only had a MeST of 40 days (range 29-75). SCID mice surviving greater than 45 days all proceeded to develop lethal GL261 gliomas (observed by MRI) shortly after drug was discontinued. C57BL/6 mice "cured" in the previous group (immune-competent) also subsequently rejected a second GL261 tumor implant challenge. Additional molecular studies show that Compound 76 increased expression and altered the localization of intracellular survivin, a molecule that can be targeted by immunotherapy.

The results of five independent studies indicate that Compound 76 slows the growth rate of intracerebral GL261 glioma relative to control groups. When given as a single dose per day (s.i.d.) Compound 76 led to complete tumor regression in up to 60% of treated mice without further progression. The subsequent rejection of a second tumor in these mice is indicative of immune memory. This magnitude of anti-tumor effect was not observed in SCID models leading to the possibility that Compound 76 may be involved in an anti-tumor immune response.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed:

1. A pharmaceutical composition comprising a compound according to formula IB

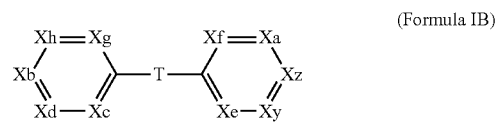

(Formula IB)

or a pharmaceutically acceptable salt, solvate, hydrate, or prodrug thereof, wherein the compound is present in an amount from about 50 to about 500 mg in the composition and wherein:

T is a bond;
$X_y$ is N or N—O;
$X_z$ is CZ;
$X_a$ is $CR_a$;
$X_b$ is $CR_b$;
$X_c$ is $CR_c$;
$X_d$ is $CR_d$;
$X_e$ is $CR_e$;
$X_f$ is $CR_4$;
$X_g$ is $CR_5$;
$X_h$ is $CR_6$;
$R_a$, $R_b$, $R_c$, $R_d$, $R_e$, $R_4$, $R_5$, and $R_6$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

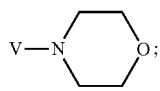

V is a bond;
Z is

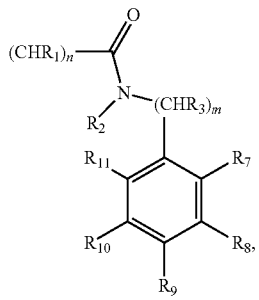

$R_1$, $R_2$, and $R_3$ are independently H or $C_1$, $C_2$, $C_3$, $C_4$, $C_5$, or $C_6$ alkyl; $R_7$, $R_8$, $R_9$, $R_{10}$, and $R_{11}$ are independently, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, or $SO_2$-lower ($C_1$, $C_2$, $C_3$, $C_4$, $C_5$, or $C_6$) alkyl; and n and m are independently 0, 1, or 2.

2. The pharmaceutical composition of claim 1, wherein $R_4$, $R_5$ and $R_6$ are each H.

3. The pharmaceutical composition of claim 1, wherein m and n are each 1 and $R_2$ and $R_3$ are each H.

4. The pharmaceutical composition of claim 1, wherein the compound is

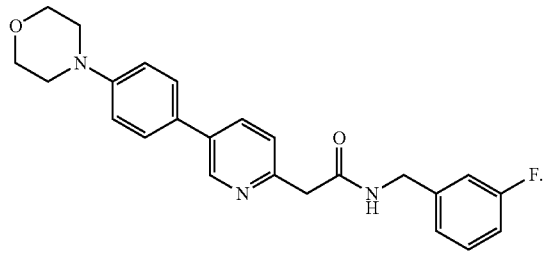 [SMILES: O=C(Cc1ccc(-c2ccc(N3CCOCC3)cc2)cn1)NCc1cccc(F)c1]

5. The pharmaceutical composition of claim 1, wherein the compound is present in an amount from about 100 mg to about 400 mg.

6. The pharmaceutical composition of claim 1, wherein the compound is present in an amount from about 200 mg to about 300 mg.

7. The pharmaceutical composition of claim 1, wherein the compound is present in an amount about 250 mg.

8. A method of treating a cell proliferative disorder comprising administering to a subject in need thereof, a therapeutically effective amount of a compound according to formula IB:

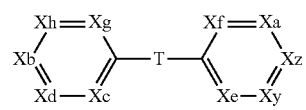

(Formula IB)

or a pharmaceutically acceptable salt, solvate, hydrate, or prodrug thereof, wherein:
T is a bond;
$X_y$ is N or N—O;
$X_z$ is CZ;
$X_a$ is $CR_a$;
$X_b$ is $CR_b$;
$X_c$ is $CR_c$;
$X_d$ is $CR_d$;
$X_e$ is $CR_e$;
$X_f$ is $CR_4$;
$X_g$ is $CR_5$;
$X_h$ is $CR_6$;
$R_a$, $R_b$, $R_c$, $R_d$, $R_e$, $R_4$, $R_5$, and $R_6$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

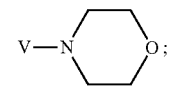

V is a bond;
Z is

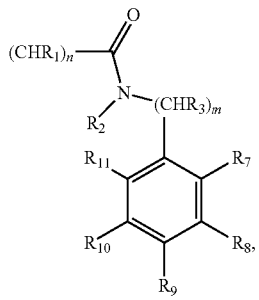

$R_1$, $R_2$, and $R_3$ are independently H or $C_1$, $C_2$, $C_3$, $C_4$, $C_5$, or $C_6$ alkyl; $R_7$, $R_8$, $R_9$, $R_{10}$, and $R_{11}$ are independently, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, or $SO_2$-lower ($C_1$, $C_2$, $C_3$, $C_4$, $C_5$, or $C_6$) alkyl; and n and m are independently 0, 1, or 2,
wherein the therapeutically effective amount is between about 50 mg to about 500 mg and
wherein the compound is administered once per 24 hour period.

9. The method of claim 8, wherein the therapeutically effective amount is between about 100 mg to about 400 mg.

10. The method of claim 8, wherein the therapeutically effective amount is between about 200 mg to about 300 mg.

11. The method of claim 8, wherein the therapeutically effective amount is about 250 mg.

12. The method of claim 8, wherein the treatment produces immunological memory in the subject.

13. The method of claim 8, wherein the treatment produces memory B-cells or T-cells in the subject.

14. The method of claim 8, wherein the cell proliferative disorder is a cancer and wherein the cancer is brain cancer.

15. A method of preventing reoccurrence of a cell proliferative disorder in a subject previously diagnosed with a cell proliferative disorder comprising administering to the subject a therapeutically effective amount of a compound according to formula IB:

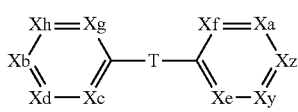

(Formula IB)

or a pharmaceutically acceptable salt, solvate, hydrate, or prodrug thereof, wherein:

T is a bond;
$X_y$ is N or N—O;
$X_z$ is CZ;
$X_a$ is $CR_a$;
$X_b$ is $CR_b$;
$X_c$ is $CR_c$;
$X_d$ is $CR_d$;
$X_e$ is $CR_e$;
$X_f$ is $CR_4$;
$X_g$ is $CR_5$;
$X_h$ is $CR_6$;
$R_a$, $R_b$, $R_c$, $R_d$, $R_e$, $R_4$, $R_5$, and $R_6$ are, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl,

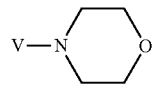

V is a bond;
Z is

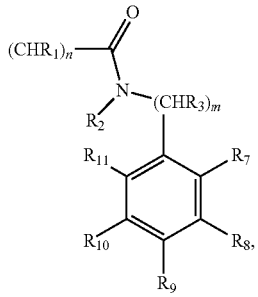

$R_1$, $R_2$, and $R_3$ are independently H or $C_1$, $C_2$, $C_3$, $C_4$, $C_5$, or $C_6$ alkyl; $R_7$, $R_8$, $R_9$, $R_{10}$, and $R_{11}$ are independently, independently, hydrogen, hydroxyl, halogen, $C_1$, $C_2$, $C_3$, $C_4$, $C_5$, or $C_6$ alkyl, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, COOH, COO-lower ($C_1$, $C_2$, $C_3$, $C_4$, $C_5$, or $C_6$) alkyl, $SO_2H$, $SO_2$-lower ($C_1$, $C_2$, $C_3$, $C_4$, $C_5$, or $C_6$) alkyl; and
n and m are independently 0, 1, or 2.

16. The method of claim 15, wherein the therapeutically effective amount is between about 50 mg to about 500 mg.

17. The method of claim 15, wherein the compound is administered once per 24 hour period.

18. The method of claim 15, wherein the compound of formula (IB) produces immunological memory in the subject.

19. The method of claim 18, wherein the compound of formula (IB) produces memory B-cells or T-cells in the subject.

* * * * *